(12) United States Patent
Skawinski et al.

(10) Patent No.: US 7,956,161 B2
(45) Date of Patent: Jun. 7, 2011

US007956161B2

(54) INTERFERONS OF RHESUS AND CYNOMOLGUS ORIGIN AND USES THEREOF

(75) Inventors: Michael A. Skawinski, Fanwood, NJ (US); Doranelly Koltchev, West Windsor, NJ (US); Ronald Jubin, Watchung, NJ (US); William A. Clark, Matawan, NJ (US); Thomas B. Lavoie, Califon, NJ (US); Sidney Pestka, North Caldwell, NJ (US)

(73) Assignee: Pestka Biomedical Laboratories, Inc., Piscataway, NJ (US)

( * ) Notice: Subject to any disclaimer, the term of this patent is extended or adjusted under 35 U.S.C. 154(b) by 157 days.

(21) Appl. No.: 12/082,815

(22) Filed: Apr. 11, 2008

(65) Prior Publication Data

US 2009/0092581 A1 Apr. 9, 2009

Related U.S. Application Data

(60) Provisional application No. 60/923,069, filed on Apr. 11, 2007, provisional application No. 60/925,281, filed on Apr. 18, 2007.

(51) Int. Cl.
*C07K 14/52* (2006.01)
*C07K 14/00* (2006.01)
*G01N 33/53* (2006.01)
*A61K 38/21* (2006.01)
*A61K 38/00* (2006.01)

(52) U.S. Cl. ....... 530/351; 530/350; 436/501; 424/85.4; 424/85.7; 514/12

(58) Field of Classification Search .......... None
See application file for complete search history.

(56) References Cited

U.S. PATENT DOCUMENTS

| 5,510,472 A | 4/1996 | Revel et al. |
| 6,482,613 B1 * | 11/2002 | Goeddel et al. ............ 435/69.51 |
| 2005/0023290 A1 | 2/2005 | Kon et al. |
| 2005/0276785 A1 | 12/2005 | Groetzbach et al. |

FOREIGN PATENT DOCUMENTS

| EP | 1236800 | 9/2002 |
| WO | WO0011151 | 3/2000 |
| WO | WO-02/36627 | 5/2002 |
| WO | WO-2005/023290 | 3/2005 |
| WO | WO2005035768 | 4/2005 |
| WO | WO-2006/099451 | 9/2006 |

OTHER PUBLICATIONS

Lawn et al., DNA sequence of two closely linked human leukocyte interferon genes. Science vol. 212, No. 4499, pp. 1159-1162 (1981).
Peskta et al., The Human Interferon Alpha Species and Receptors. Biopolymers vol. 55, No. 4, pp. 245-287 (2000).
Tatsumi et al., Molecular cloning and expression of cynomolgus monkey interferon-gamma DNA. International Archives of Allergy and Immunology. vol. 114, No. 3, pp. 229-236 (1997).
DATABASE EMBL [Online], "Maeaca mulatta chromosome 9 BAC CH250-17J24," XP002496133, EMBL:CT027655, Database accession No. CT027655 (2005).
DATABASE EMBL [Online], "Maeaca mulatta chromosome 9 BAC CH250-288D8," XP002506301, EMBL:CT027659, Database accession No. CT027659 (2005).
Gibbs et al., "Evolutionary and biomedical insights from the rhesus macaque genome," Science, 316(5822):222-234 (2007).
NCBI Reference Sequence [Online] XM_001107516.1, PREDICATED: Macaca mulatta similar to interferon, alpha 2 (LOC709948), mRNA, 2 pages (Jun. 14, 2006); http://www.ncbi.nlm.nih.gov/nuccore/XM_00110756.1?report=genbank.
Villinger et. at, "Comparative Sequence Analysis Of Cytokine Genes From Human And Nonhuman Primates," *Journal Of Immunology*, 155(1:5):3946-3954 (1995).

* cited by examiner

*Primary Examiner* — Christine J Saoud
*Assistant Examiner* — Jegatheesan Seharaseyon
(74) *Attorney, Agent, or Firm* — Ropes & Gray LLP; Barbara A. Ruskin; Brian M. Gummow

(57) ABSTRACT

Disclosed are interferons of Rhesus and Cynomolgus origin and methods of production and use thereof.

12 Claims, 3 Drawing Sheets

SEQUENCE LISTING

<160> NUMBER OF SEQ ID NOS: 69

<210> SEQ ID NO 1
<211> LENGTH: 570
<212> TYPE: DNA
<213> ORGANISM: Macaca mulatta

<400> SEQUENCE: 1
atggccctgt ccttttcttt actgatggcc gtggtggtgc tcagctacaa atccatctac     60
tctctgggct gtgatctgcc tcagatccac agcctgggtc ataggagggc cttgatactc    120

```
ctggcacaaa tgggaaggat ctctcctttc tcctgtctga aggacagaca tgactttgga      180
ttcccccagg aggagtttga tggcaaccag ttccagaagg ctcaagccat gtctgtcctc      240
catgagatga tccagcagac cttcaatctc ttcagcacaa aggactcatc tgctgcttgg      300
gaacagaacc tcctagaaaa attttccgct gagctttacc agcaactgaa tgacctgaaa      360
gcctgtgtga tagcagagcc tgggatggaa gacactccct tgatgaatga ggactccatc      420
ctggctgtga agaaatactt ccaaagaatc actctctatc tgacggagaa gaaatacagc      480
ccatgtgcct gggaggttgt cagaacagaa atcatgagat ctctctcttt ttcaacaaac      540
ttgcaaaaaa gattaaggag gaaggattga                                      570
```

<210> SEQ ID NO 2
<211> LENGTH: 189
<212> TYPE: PRT
<213> ORGANISM: Macaca mulatta

<400> SEQUENCE: 2

```
Met Ala Leu Ser Phe Ser Leu Leu Met Ala Val Val Leu Ser Tyr
 1               5                  10                  15

Lys Ser Ile Tyr Ser Leu Gly Cys Asp Leu Pro Gln Ile His Ser Leu
                20                  25                  30

Gly His Arg Arg Ala Leu Ile Leu Leu Ala Gln Met Gly Arg Ile Ser
            35                  40                  45

Pro Phe Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
    65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
                100                 105                 110

Tyr Gln Gln Leu Asn Asp Leu Lys Ala Cys Val Ile Ala Glu Pro Gly
            115                 120                 125

Met Glu Asp Thr Pro Leu Met Asn Glu Asp Ser Ile Leu Ala Val Lys
        130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Thr Glu Ile Met Arg Ser Leu Ser
                165                 170                 175

Phe Ser Thr Asn Leu Gln Lys Arg Leu Arg Arg Lys Asp
                180                 185
```

<210> SEQ ID NO 3
<211> LENGTH: 570
<212> TYPE: DNA
<213> ORGANISM: Macaca mulatta

<400> SEQUENCE: 3

```
atggccctgt cctttctttt actgatggcc gtggtggtgc tcagctacaa atccatctac       60
tctctgggct gtgatctgcc tcagatccac agcctgggtc ataggagggc cttgatactc      120
ctggcacaaa tgggaaggat ctctcctttc tcctgtctga aggacagaca tgactttgga      180
ttcccccagg aggagtttga tggcaaccag ttccagaagg ctcaagccat gtctgtcctc      240
catgagatga tccagcagac cttcaatccc ttcagcacaa aggactcatc tgctgcttgg      300
gaacagaacc tcctagaaaa attttccgct gagctttacc agcaactgaa tgacctgaaa      360
```

```
gcctgtgtga tagcagagcc tgggatggaa gacactccct tgatgaatga ggactccctc    420
ctggctgtga agaaatactt ccaaagaatc actctctatc tgacggagaa gaaatacagc    480
ccatgtgcct gggaggttgt cagaacagaa atcatgagat ctctctcttt ttcaacaaac    540
ttgcaaaaaa gattaaggag gaaggattga                                    570
```

```
<210> SEQ ID NO 4
<211> LENGTH: 189
<212> TYPE: PRT
<213> ORGANISM: Macaca mulatta

<400> SEQUENCE: 4
```

```
Met Ala Leu Ser Phe Ser Leu Leu Met Ala Val Val Leu Ser Tyr
 1               5                  10                  15

Lys Ser Ile Tyr Ser Leu Gly Cys Asp Leu Pro Gln Ile His Ser Leu
                20                  25                  30

Gly His Arg Arg Ala Leu Ile Leu Leu Ala Gln Met Gly Arg Ile Ser
            35                  40                  45

Pro Phe Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
65                  70                  75                  80

His Glu Met Ile Gln Gln Thr Phe Asn Pro Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Asp Leu Lys Ala Cys Val Ile Ala Glu Pro Gly
        115                 120                 125

Met Glu Asp Thr Pro Leu Met Asn Glu Asp Ser Leu Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Thr Glu Ile Met Arg Ser Leu Ser
                165                 170                 175

Phe Ser Thr Asn Leu Gln Lys Arg Leu Arg Arg Lys Asp
            180                 185
```

```
<210> SEQ ID NO 5
<211> LENGTH: 570
<212> TYPE: DNA
<213> ORGANISM: Macaca mulatta

<400> SEQUENCE: 5
atggccctgt ccttttcttt actgatggcc gtggtggtgc tcagctacaa atccatctgc     60
tctctgggct gtgatctgcc ccagacccac agcctgggtc ataggagggc cttgatactc    120
ctggaacaaa tgggaaggat ctctcctttc tcctgtctga aggacagacg tgactttgga    180
ttcccccagg aggagtttga tggcaaccag ttccagaagg ctcaagccat gtctgtcctc    240
catgagatga tccagcagac cttcaatctc ttcagcacaa aggactcatc tgctgcttgg    300
gaacagaacc tcctagaaaa attttccacc gaactttacc agcaactgaa tgacctgaaa    360
gcctgtgtga tagcagagcc tgggatggaa gacactccct tgatgaatga ggactccatc    420
ctggctgtga agaaatactt ccaaagaatc actctctatc tgacggagaa gaaatacagc    480
ccatgtgcct gggaggttgt cagaacagaa atcatgagat ccctctcttt ttcaacaaac    540
ttgccaaaaa gattaaggag gaaggattga                                    570
```

-continued

<210> SEQ ID NO 6
<211> LENGTH: 189
<212> TYPE: PRT
<213> ORGANISM: Macaca mulatta

<400> SEQUENCE: 6

```
Met Ala Leu Ser Phe Ser Leu Leu Met Ala Val Val Leu Ser Tyr
1               5                   10                  15

Lys Ser Ile Cys Ser Leu Gly Cys Asp Leu Pro Gln Thr His Ser Leu
            20                  25                  30

Gly His Arg Arg Ala Leu Ile Leu Leu Glu Gln Met Gly Arg Ile Ser
        35                  40                  45

Pro Phe Ser Cys Leu Lys Asp Arg Arg Asp Phe Gly Phe Pro Gln Glu
    50                  55                  60

Glu Phe Asp Gly Asn Gln Phe Gln Lys Ala Gln Ala Met Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Thr Glu Leu
            100                 105                 110

Tyr Gln Gln Leu Asn Asp Leu Lys Ala Cys Val Ile Ala Glu Pro Gly
        115                 120                 125

Met Glu Asp Thr Pro Leu Met Asn Glu Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Thr Glu Ile Met Arg Ser Leu Ser
                165                 170                 175

Phe Ser Thr Asn Leu Pro Lys Arg Leu Arg Arg Lys Asp
            180                 185
```

<210> SEQ ID NO 7
<211> LENGTH: 570
<212> TYPE: DNA
<213> ORGANISM: Macaca mulatta

<400> SEQUENCE: 7

```
atggccctgt cctttctttt actgatggcc gtggtggtgc tcagctacaa atccatctgc      60
tctctgggct gtgatcttcc tcagacccac agcctgggtc ataggagggc cttgatactc     120
ctggcacaaa tggaaggat ctctccgttc tcctgtctga aggacagaca tgactttgga     180
ttcccccagg aggagtttga tggcaaccag ttccagaagg ctcaagccat gtctgtcctc     240
catgagatga tccagcagac cttcaatctc ttcagcacaa aggactcatc tgctgcttgg     300
gaacagaacc tcctagaaaa attttccgct gagctttacc agcaactgaa tgacctgaaa     360
gcctgtgtga tagcagagcc tgggatggaa gacactccct tgatgaatga ggactccatc     420
ctggctgtga agaaatactt ccaaagaatc actctctatc tgacggagaa gaaatacagc     480
ccttgtgcct gggaggttgt cagagcagaa atcatgagat ccctctcttt tcaacaaac     540
ttgcaaaaaa gattaaggag gaaggattga                                      570
```

<210> SEQ ID NO 8
<211> LENGTH: 189
<212> TYPE: PRT
<213> ORGANISM: Macaca mulatta

<400> SEQUENCE: 8

Met Ala Leu Ser Phe Ser Leu Leu Met Ala Val Val Leu Ser Tyr
1               5                   10                  15

Lys Ser Ile Cys Ser Leu Gly Cys Asp Leu Pro Gln Thr His Ser Leu
            20                  25                  30

Gly His Arg Arg Ala Leu Ile Leu Leu Ala Gln Met Gly Arg Ile Ser
                35                  40                  45

Pro Phe Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Asp Leu Lys Ala Cys Val Ile Ala Glu Pro Gly
                115                 120                 125

Met Glu Asp Thr Pro Leu Met Asn Glu Asp Ser Ile Leu Ala Val Lys
        130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 9
<211> LENGTH: 570
<212> TYPE: DNA
<213> ORGANISM: Macaca mulatta

<400> SEQUENCE: 9
atggccctgt cctttctttt actgatggcc gtggtggtgc tcaactacaa atccatctgc    60
tctctgggct gtgatcttcc tctgacccag agcctgggtc ataggagggc tttgatactc   120
ctagcacaaa tgggaagaat ctctcctta tcctgtctga aggacagaca tgactttgga    180
ttcccccagg aggagtttga tggcaaccag ttccagaagg ctcaagccat gtctgtcctc    240
catgagatga tccagcagac cttcaatctc ttcagcacaa aggactcatc tgctgcttgg    300
gaacagaacc tcctagaaaa atttccgct gagctttacc agcaacagaa tgacctgaaa    360
gcctgtgtga tagcagagcc tgggatggaa gagactctct tgatgaatga ggactccatc   420
ctggctgtga agaaatactt ccaaagaatc actctctatc tgacggagaa gaaatacagc   480
ccatgtgcct gggaggttgt cagagcagaa atcatgagat ccctctcttt ttcaacaaac   540
ttgcaaaaaa gattaaggag gaaggattga                                     570

<210> SEQ ID NO 10
<211> LENGTH: 189
<212> TYPE: PRT
<213> ORGANISM: Macaca mulatta

<400> SEQUENCE: 10

Met Ala Leu Ser Phe Ser Leu Leu Met Ala Val Val Val Leu Asn Tyr
1               5                   10                  15

Lys Ser Ile Cys Ser Leu Gly Cys Asp Leu Pro Leu Thr Gln Ser Leu
            20                  25                  30

Gly His Arg Arg Ala Leu Ile Leu Leu Ala Gln Met Gly Arg Ile Ser
                35                  40                  45

```
Pro Leu Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
 65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Gln Asn Asp Leu Lys Ala Cys Val Ile Ala Glu Pro Gly
            115                 120                 125

Met Glu Glu Thr Leu Leu Met Asn Glu Asp Ser Ile Leu Ala Val Lys
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185
```

<210> SEQ ID NO 11
<211> LENGTH: 570
<212> TYPE: DNA
<213> ORGANISM: Macaca mulatta

<400> SEQUENCE: 11

```
atggccctgt cctttctttt actgatggcc atggtggtgc tcagctacaa atccatctgc    60
tctctgggct gtgatctgcc ccaaacccac agcctgggtc ataggagggc cttgatactc   120
ctagcacaaa tgggaagaat ctctcctttc tcctgtctga aggacagaca tgactttgga   180
ttcccccagg aggagtttga tggcaaccag ttccagaagg ctcaagccat gtctgtcctc   240
catgagatga tccagcagac cttcaatctc ttcagcacaa aggactcatc tgctgcttgg   300
gaacagaacc tcctagaaaa attttccgct gagctttacc agcaactgaa tgacctgaaa   360
gcctgtgtga tagcagagcc tgggatggaa gacactccct tgatgaatga ggactccatc   420
ctggctgtga agaaatactt ccaaagaatc actctctatc tgacggagaa aaaatacagc   480
ccttgtgcct gggaggttgt cagagcagaa atcatgagat ccctctcttt ttcaacaaac   540
ttgcaaaaaa gattaaggag gaaggattga                                    570
```

<210> SEQ ID NO 12
<211> LENGTH: 189
<212> TYPE: PRT
<213> ORGANISM: Macaca mulatta

<400> SEQUENCE: 12

```
Met Ala Leu Ser Phe Ser Leu Leu Met Ala Met Val Val Leu Ser Tyr
  1               5                  10                  15

Lys Ser Ile Cys Ser Leu Gly Cys Asp Leu Pro Gln Thr His Ser Leu
                20                  25                  30

Gly His Arg Arg Ala Leu Ile Leu Leu Ala Gln Met Gly Arg Ile Ser
            35                  40                  45

Pro Phe Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
 65                  70                  75                  80

His Glu Met Ile Gln Gln Thr Phe Asn Leu Phe Ser Thr Lys Asp Ser
```

```
                    85                  90                  95
Ser Ala Ala Trp Glu Gln Asn Leu Leu Glu Lys Phe Ser Ala Glu Leu
                100                 105                 110

Tyr Gln Gln Leu Asn Asp Leu Lys Ala Cys Val Ile Ala Glu Pro Gly
            115                 120                 125

Met Glu Asp Thr Pro Leu Met Asn Glu Asp Ser Ile Leu Ala Val Lys
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 13
<211> LENGTH: 546
<212> TYPE: DNA
<213> ORGANISM: Macaca mulatta

<400> SEQUENCE: 13
atggccctgg tggtgctcag ctgcaagtca agttgctctc tgggctgtga tctgcctcag        60
acccacagcc tgggtcacag gaggaccatg atgctcctgg tacaaatgag aagaatctct       120
cttttctcct gtctgaagga cagacacgac ttcagatttc cccaggagga gtttgatggc       180
aaccagttcc agaaggctca agctatctct gtcctccatg aggtgattca gcagacctac       240
aacctcttca gcacaaagga ctcatctgct gcttgggatg aaatgcttct agacaaactc       300
tacactgaac tttaccagca gctgaatgac ctggaagcct gtgtgatgca ggaggcgtgg       360
gtgggagaga ctcccctgat gaatgaggac tccatcctgg ctgtgagaaa atacttccaa       420
agaatcactc tctacctgac agagaagaag tatagccctt gtgcatggga ggttgtcaga       480
gcagaaatca tgagatcctt ctcttcatca gaaacttgc aagaaagatt aaggaggaag       540
gaataa                                                                  546

<210> SEQ ID NO 14
<211> LENGTH: 181
<212> TYPE: PRT
<213> ORGANISM: Macaca mulatta

<400> SEQUENCE: 14

Met Ala Leu Val Val Leu Ser Cys Lys Ser Ser Cys Ser Leu Gly Cys
1               5                   10                  15

Asp Leu Pro Gln Thr His Ser Leu Gly His Arg Arg Thr Met Met Leu
            20                  25                  30

Leu Val Gln Met Arg Arg Ile Ser Leu Phe Ser Cys Leu Lys Asp Arg
        35                  40                  45

His Asp Phe Arg Phe Pro Gln Glu Glu Phe Asp Gly Asn Gln Phe Gln
    50                  55                  60

Lys Ala Gln Ala Ile Ser Val Leu His Glu Val Ile Gln Gln Thr Tyr
65                  70                  75                  80

Asn Leu Phe Ser Thr Lys Asp Ser Ser Ala Ala Trp Asp Glu Met Leu
                85                  90                  95

Leu Asp Lys Leu Tyr Thr Glu Leu Tyr Gln Gln Leu Asn Asp Leu Glu
            100                 105                 110

Ala Cys Val Met Gln Glu Ala Trp Val Gly Glu Thr Pro Leu Met Asn
        115                 120                 125
```

Glu Asp Ser Ile Leu Ala Val Arg Lys Tyr Phe Gln Arg Ile Thr Leu
            130                 135                 140

Tyr Leu Thr Glu Lys Lys Tyr Ser Pro Cys Ala Trp Glu Val Val Arg
145                 150                 155                 160

Ala Glu Ile Met Arg Ser Phe Ser Ser Arg Asn Leu Gln Glu Arg
                165                 170                 175

Leu Arg Arg Lys Glu
            180

<210> SEQ ID NO 15
<211> LENGTH: 570
<212> TYPE: DNA
<213> ORGANISM: Macaca mulatta

<400> SEQUENCE: 15
atggccttgc cttttgcttt actcatggcc ctggtggtgc tcagctgcaa gtcaagttgc      60
tctctgggct gtgatctgcc tcagacccac agcctgggtc acaggaggac catgatgctc     120
ctggtacaaa tgagaagaat ctctcttttc tcctgtctga aggacagaca cgacttcaga     180
tttccccagg aggagtttga tggcaaccag ttccagaagg ctcaagctat ctctgtcctc     240
catgaggtga ttcagcagac ctacaacctc ttcagcacaa aggactcatc tgctgcttgg     300
gatgaaatgc ttctagacaa actctacact gaactttacc agcagctgaa tgacctggaa     360
gcctgtgtga tgcaggaggc gtgggtggga gagactcccc tgatgaatga ggactccatc     420
ctggctgtga gaaaatactt ccaaagaatc actctctacc tgacagagaa gaagtatagc     480
ccttgtgcat gggaggttgt cagagcagaa atcatgagat ccttctcttc atcaagaaac     540
ttgcaagaaa gattaaggag gaaggaataa                                      570

<210> SEQ ID NO 16
<211> LENGTH: 189
<212> TYPE: PRT
<213> ORGANISM: Macaca mulatta

<400> SEQUENCE: 16

Met Ala Leu Pro Phe Ala Leu Leu Met Ala Leu Val Val Leu Ser Cys
1               5                   10                  15

Lys Ser Ser Cys Ser Leu Gly Cys Asp Leu Pro Gln Thr His Ser Leu
            20                  25                  30

Gly His Arg Arg Thr Met Met Leu Leu Val Gln Met Arg Arg Ile Ser
        35                  40                  45

Leu Phe Ser Cys Leu Lys Asp Arg His Asp Phe Arg Phe Pro Gln Glu
    50                  55                  60

Glu Phe Asp Gly Asn Gln Phe Gln Lys Ala Gln Ala Ile Ser Val Leu
65                  70                  75                  80

His Glu Val Ile Gln Gln Thr Tyr Asn Leu Phe Ser Thr Lys Asp Ser
                85                  90                  95

Ser Ala Ala Trp Asp Glu Met Leu Leu Asp Lys Leu Tyr Thr Glu Leu
            100                 105                 110

Tyr Gln Gln Leu Asn Asp Leu Glu Ala Cys Val Met Gln Glu Ala Trp
        115                 120                 125

Val Gly Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Ser Ser Arg Asn Leu Gln Glu Arg Leu Arg Arg Lys Glu
            180                 185

<210> SEQ ID NO 17
<211> LENGTH: 570
<212> TYPE: DNA
<213> ORGANISM: Macaca mulatta

<400> SEQUENCE: 17

```
atggccttga ccttttattt actgatggcc ctagtggtgc tcagctacaa gccattcagc      60
tctctgggct gtgatctgcc tcagacccac agcctgggtt acaggaggcc cttggtgctc     120
ctggcacaaa tgagaagaat ctctcctttc tcctgcctga aggacagaca tgactttgaa     180
ttaccccagg aggagtttga tgacaaaaac ttccagaagg ctcaagccat ctctgtcctc     240
catgagataa tccagcagac cttcaacctc ttcaacacaa agaattcatc tgctgctttc     300
aatgagaccc ttctagatga attctacatc gaacttgacc agcagctgaa tgacctggag     360
tcctgtgtga tgcaggaagt gggggtgaca gagactcacc tgatgtacga ggactccatc     420
ctggctgtga agaaatactt ccgaagaatc actctctatc tgacagagaa gaaatacagc     480
ccttgtgcct gggaggttgt cagagcagaa atcatgagat ccttctcttt atcaatcaac     540
ttgcaaaaaa gattgaagag taaggaataa                                      570
```

<210> SEQ ID NO 18
<211> LENGTH: 189
<212> TYPE: PRT
<213> ORGANISM: Macaca mulatta

<400> SEQUENCE: 18

Met Ala Leu Thr Phe Tyr Leu Leu Met Ala Leu Val Val Leu Ser Tyr
 1               5                  10                  15

Lys Pro Phe Ser Ser Leu Gly Cys Asp Leu Pro Gln Thr His Ser Leu
            20                  25                  30

Gly Tyr Arg Arg Pro Leu Val Leu Leu Ala Gln Met Arg Arg Ile Ser
        35                  40                  45

Pro Phe Ser Cys Leu Lys Asp Arg His Asp Phe Glu Leu Pro Gln Glu
    50                  55                  60

Glu Phe Asp Asp Lys Asn Phe Gln Lys Ala Gln Ala Ile Ser Val Leu
65                  70                  75                  80

His Glu Ile Ile Gln Gln Thr Phe Asn Leu Phe Asn Thr Lys Asn Ser
                85                  90                  95

Ser Ala Ala Phe Asn Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Thr Glu Thr His Leu Met Tyr Glu Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 19
<211> LENGTH: 570
<212> TYPE: DNA

<213> ORGANISM: Macaca mulatta

<400> SEQUENCE: 19

```
atggcattgc cttttgcttt actgatggcc ctggtggtgc tcagctgcaa gtcaagctgc     60
tctctgggct gtgatctgcc tgagacccac agcctggata acagaaggac catgatgctc    120
ctgaaacaaa tgagcagaat ctctccttcc tcctgtctga tggacagaca tgactttgga    180
tttccccagc aggagtttga tggcaaccag ttccagaagg ctccagccat ctctgtcctc    240
catgagctga tccagcagac cttcaacctc tttaccacaa aagactcatc tgctgcttgg    300
gatgaggacc tcctagacaa attctgcact gaactctacc agcagctgaa tgacttggaa    360
gcctgtgtca tgcagcagga gagggtggga gaaactcccc tgatgaatgc ggactccacc    420
ttggctgtga agaaatactt ccgaagaatc actctctatc tgacagagaa gaaatacagc    480
ccttgtgcct gggaggttgt cagagcagaa atcatgagat ctttctcttt atcaacaaac    540
ttgcaagaaa gattaaggag gaaggaataa                                     570
```

<210> SEQ ID NO 20
<211> LENGTH: 189
<212> TYPE: PRT
<213> ORGANISM: Macaca mulatta

<400> SEQUENCE: 20

```
Met Ala Leu Pro Phe Ala Leu Leu Met Ala Leu Val Val Leu Ser Cys
  1               5                  10                  15
Lys Ser Ser Cys Ser Leu Gly Cys Asp Leu Pro Glu Thr His Ser Leu
             20                  25                  30
Asp Asn Arg Arg Thr Met Met Leu Leu Lys Gln Met Ser Arg Ile Ser
         35                  40                  45
Pro Ser Ser Cys Leu Met Asp Arg His Asp Phe Gly Phe Pro Gln Gln
     50                  55                  60
Glu Phe Asp Gly Asn Gln Phe Gln Lys Ala Pro Ala Ile Ser Val Leu
 65                  70                  75                  80
His Glu Leu Ile Gln Gln Thr Phe Asn Leu Phe Thr Thr Lys Asp Ser
                 85                  90                  95
Ser Ala Ala Trp Asp Glu Asp Leu Leu Asp Lys Phe Cys Thr Glu Leu
            100                 105                 110
Tyr Gln Gln Leu Asn Asp Leu Glu Ala Cys Val Met Gln Gln Glu Arg
        115                 120                 125
Val Gly Glu Thr Pro Leu Met Asn Ala Asp Ser Thr Leu Ala Val Lys
    130                 135                 140
Lys Tyr Phe Arg Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Phe Ser
                165                 170                 175
Leu Ser Thr Asn Leu Gln Glu Arg Leu Arg Arg Lys Glu
            180                 185
```

<210> SEQ ID NO 21
<211> LENGTH: 570
<212> TYPE: DNA
<213> ORGANISM: Macaca mulatta

<400> SEQUENCE: 21

```
atggcattgc cttttgcttt actgatggcc ctggtggtgc tcagctgcaa gtcaagctgc     60
tctctgggct gtgatctgcc tgagacccac agcctggata acagaaggac catgatgctc    120
```

```
ctgaaacaaa tgagcagaat ctctccttcc tcctgtctga tggacagaca tgactttgga    180
tttccccagc aggagtttga tggcaaccag ttccagaagg ctcaagccat ctctgtcctc    240
catgagctga tccagcagac cttcaacctc tttaccacaa aagactcatc tgctgcttgg    300
gatgaggacc tcctagacaa attctgcact gaactctacc agcagctgaa tgacttggaa    360
gcctgtgtca tgcagcagga gagggtggga gaaactcccc tgatgaatgc ggactccacc    420
ttggctgtga agaaatactt ccgaagaatc actctctatc tgacagagaa gaaatacagc    480
ccttgtgcct gggaggttgt cagagcagaa atcatgagat ccttctcttt atcaacaaac    540
ttgcaagaaa gattaaggag gaaggaataa                                     570
```

<210> SEQ ID NO 22
<211> LENGTH: 189
<212> TYPE: PRT
<213> ORGANISM: Macaca mulatta

<400> SEQUENCE: 22

```
Met Ala Leu Pro Phe Ala Leu Leu Met Ala Leu Val Val Leu Ser Cys
 1               5                  10                  15

Lys Ser Ser Cys Ser Leu Gly Cys Asp Leu Pro Glu Thr His Ser Leu
            20                  25                  30

Asp Asn Arg Arg Thr Met Met Leu Leu Lys Gln Met Ser Arg Ile Ser
        35                  40                  45

Pro Ser Ser Cys Leu Met Asp Arg His Asp Phe Gly Phe Pro Gln Gln
    50                  55                  60

Glu Phe Asp Gly Asn Gln Phe Gln Lys Ala Gln Ala Ile Ser Val Leu
65                  70                  75                  80

His Glu Leu Ile Gln Gln Thr Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Gln Glu Arg
        115                 120                 125

Val Gly Glu Thr Pro Leu Met Asn Ala Asp Ser Thr Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Thr Asn Leu Gln Glu Arg Leu Arg Arg Lys Glu
            180                 185
```

<210> SEQ ID NO 23
<211> LENGTH: 570
<212> TYPE: DNA
<213> ORGANISM: Macaca mulatta

<400> SEQUENCE: 23

```
atggccttgc cctttgcttt actgatggcc ctggtggtgc tcagcagcaa gtcaagttgc     60
tctctgggct gtgatctgcc tgagacccac agcctggata caggaagac catgatgctc    120 ctggcacaga tgagcagaat ctctccttcc tcctgtctga tggacagaca tgactttgga    180
tttccccagc aggagtttga tggcaaccag ttccagaagg ctcaagccat ctctgtcctc    240
catgagctga tccagcagac cttcaacctc tttaccacaa aagactcatc tgctgcttgg    300
gatgaggacc tcctagacaa attctgcact gaactctacc agcagctgaa tgacttggaa    360
```

```
gcctgtgtca tgcagcagga gagggtggga gaaactcccc tgatgaatgc ggactccacc    420
ttggctgtga agaaatactt ccgaagaatc actctctatc tgacagagaa gaaatacagc    480
ccttgtgcct gggaggttat cagagcagaa atcatgagat ccttctcttt atcaacaaac    540
ttgcaagaaa gattaaggag gaaggaataa                                      570
```

<210> SEQ ID NO 24
<211> LENGTH: 189
<212> TYPE: PRT
<213> ORGANISM: Macaca mulatta

<400> SEQUENCE: 24

```
Met Ala Leu Pro Phe Ala Leu Leu Met Ala Leu Val Val Leu Ser Ser
 1               5                  10                  15

Lys Ser Ser Cys Ser Leu Gly Cys Asp Leu Pro Glu Thr His Ser Leu
            20                  25                  30

Asp Asn Arg Lys Thr Met Met Leu Leu Ala Gln Met Ser Arg Ile Ser
        35                  40                  45

Pro Ser Ser Cys Leu Met Asp Arg His Asp Phe Gly Phe Pro Gln Gln
    50                  55                  60

Glu Phe Asp Gly Asn Gln Phe Gln Lys Ala Gln Ala Ile Ser Val Leu
65                  70                  75                  80

His Glu Leu Ile Gln Gln Thr Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Gln Glu Arg
        115                 120                 125

Val Gly Glu Thr Pro Leu Met Asn Ala Asp Ser Thr Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Ile Arg Ala Glu Ile Met Arg Ser Phe Ser
                165                 170                 175

Leu Ser Thr Asn Leu Gln Glu Arg Leu Arg Arg Lys Glu
            180                 185
```

<210> SEQ ID NO 25
<211> LENGTH: 570
<212> TYPE: DNA
<213> ORGANISM: Macaca mulatta

<400> SEQUENCE: 25

```
atggcattgc cctttgcttt aatgatggcc ctgctggtgc ttagctacaa gtcaagctgc     60
tctctgggct gtaatccatc tcaaacccac aacatgaata acaggaggac tttgatgctc    120
atggcacaaa tgaggagaat ctctcctttt tcatgcctga aggacagaaa tgactttgaa    180
tttccccagg aggagtttga tggcaaccag ttccagaata ctcaagccat ctctctcctc    240
catgagatga tccagcagac cttcaatctc ttcagcacaa aggactcatc tgctgcttgg    300
gatgagaccc tcctagacaa attctacatt gaacttttcc agcaactgaa tgacctggaa    360
gcctgtgtga tacaggaggc tggggtagaa gagactcccc tgatgaatga ggactccatc    420
ctggctgtga agaaatactt ccaaagaatc actctctatc tgatggagaa gaaatacagc    480
ccatgtgcct gggaggttgt cagagcagaa atcatgagat ccctctcttt ttcaacaaac    540
ttgcaaaaaa gattaaggag gaaggattga                                      570
```

<210> SEQ ID NO 26
<211> LENGTH: 189
<212> TYPE: PRT
<213> ORGANISM: Macaca mulatta

<400> SEQUENCE: 26

```
Met Ala Leu Pro Phe Ala Leu Met Met Ala Leu Leu Val Leu Ser Tyr
 1               5                  10                  15

Lys Ser Ser Cys Ser Leu Gly Cys Asn Pro Ser Gln Thr His Asn Met
            20                  25                  30

Asn Asn Arg Arg Thr Leu Met Leu Met Ala Gln Met Arg Arg Ile Ser
        35                  40                  45

Pro Phe Ser Cys Leu Lys Asp Arg Asn Asp Phe Glu Phe Pro Gln Glu
    50                  55                  60

Glu Phe Asp Gly Asn Gln Phe Gln Asn Thr Gln Ala Ile Ser Leu Leu
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Ile Gln Glu Ala Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 27
<211> LENGTH: 570
<212> TYPE: DNA
<213> ORGANISM: Macaca mulatta

<400> SEQUENCE: 27

```
atggcattgc cctttgcttt aatgatggcc ctgctggtgc ttagctacaa gtcaagctgc      60
tctctgggct gtaatccatc tcaaacccac aacatgaata acaggaggac tttgatgctc     120
atggcacaaa tgaggagaat ctctcctttt tcatgcctga aggacagaaa tgactttgaa     180
tttccccagg aggagtttga tggcaaccag ttccagaata ctcaagccat ctctctcctc     240
catgagatga tccagcagac cttcaatctc ttcagcacaa aggactcatc tgctgcttgg     300
gatgagaccc tcctagacaa attctacatt gaacttttcc agcaactgaa tgacctggaa     360
gcctgtgtga tacaggaggc tggggtagaa gagactcccc tgatgaatga ggactccatc     420
ctggctgtga ggaaatactt ccaaagaatc actctctatc tgatggagaa gaaatacagc     480
ccatgtgcct gggaggttgt cagagcagaa atcatgagat ccctctcttt ttcaacaaac     540
ttgcaaaaaa gattaaggag gaaggattga                                      570
```

<210> SEQ ID NO 28
<211> LENGTH: 189
<212> TYPE: PRT
<213> ORGANISM: Macaca mulatta

<400> SEQUENCE: 28

```
Met Ala Leu Pro Phe Ala Leu Met Met Ala Leu Leu Val Leu Ser Tyr
 1               5                  10                  15

Lys Ser Ser Cys Ser Leu Gly Cys Asn Pro Ser Gln Thr His Asn Met
             20                  25                  30

Asn Asn Arg Arg Thr Leu Met Leu Met Ala Gln Met Arg Arg Ile Ser
         35                  40                  45

Pro Phe Ser Cys Leu Lys Asp Arg Asn Asp Phe Glu Phe Pro Gln Glu
     50                  55                  60

Glu Phe Asp Gly Asn Gln Phe Gln Asn Thr Gln Ala Ile Ser Leu Leu
 65                  70                  75                  80

His Glu Met Ile Gln Gln Thr Phe Asn Leu Phe Ser Thr Lys Asp Ser
                 85                  90                  95

Ser Ala Ala Trp Asp Glu Thr Leu Leu Asp Lys Phe Tyr Ile Glu Leu
             100                 105                 110

Phe Gln Gln Leu Asn Asp Leu Glu Ala Cys Val Ile Gln Glu Ala Gly
         115                 120                 125

Val Glu Glu Thr Pro Leu Met Asn Glu Asp Ser Ile Leu Ala Val Arg
     130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                 165                 170                 175

Phe Ser Thr Asn Leu Gln Lys Arg Leu Arg Arg Lys Asp
                 180                 185

<210> SEQ ID NO 29
<211> LENGTH: 570
<212> TYPE: DNA
<213> ORGANISM: Macaca mulatta

<400> SEQUENCE: 29
atggccctgt cctttctttt actgatggcc atggtggtgc tcagctacaa atccatctgc    60
tctctgggct gtgatctgcc ccaaacccac agcctgggtc ataggagggc cttgatactc   120
ctagcacaaa tgggaagaat ctctcctttc tcctgtctga aggacagaca tgactttgga   180
ttcccccagg aggagtttga tggcaaccag ttccagaagg ctcaagccat gtctgtcctc   240
catgagatga tccagcagac cttcaatctc ttcagcacaa aggactcatc tgctgcttgg   300
gatgagaccc tcctagacaa attctacatt gaacttttcc agcaactgaa tgacctggaa   360
gcctgtgtga tacaggaggc tggggtagaa gagactcccc tgatgaatga ggactccatc   420
ctggctgtga ggaaatactt ccaaagaatc actctctatc tgacggagaa gaaatacagc   480
ccttgtgcct gggaggttgt cagagcagaa atcatgagat ccctctcttt ttcaacaaac   540
ttgcaaaaaa gattaaggag gaaggattga                                     570

<210> SEQ ID NO 30
<211> LENGTH: 189
<212> TYPE: PRT
<213> ORGANISM: Macaca mulatta

<400> SEQUENCE: 30

Met Ala Leu Ser Phe Ser Leu Leu Met Ala Met Val Val Leu Ser Tyr
 1               5                  10                  15

Lys Ser Ile Cys Ser Leu Gly Cys Asp Leu Pro Gln Thr His Ser Leu
             20                  25                  30

Gly His Arg Arg Ala Leu Ile Leu Leu Ala Gln Met Gly Arg Ile Ser
         35                  40                  45
```

Pro Phe Ser Cys Leu Lys Asp Arg His Asp Phe Gly Phe Pro Gln Glu
        50                  55                  60

Glu Phe Asp Gly Asn Gln Phe Gln Lys Ala Gln Ala Met Ser Val Leu
 65                  70                  75                  80

His Glu Met Ile Gln Gln Thr Phe Asn Leu Phe Ser Thr Lys Asp Ser
             85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Ile Gln Glu Ala Gly
        115                 120                 125

Val Glu Glu Thr Pro Leu Met Asn Glu Asp Ser Ile Leu Ala Val Arg
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 31
<211> LENGTH: 570
<212> TYPE: DNA
<213> ORGANISM: Macaca mulatta

<400> SEQUENCE: 31
atggccctgt cctttctttt actgatggcc gtggtggtgc tcagctacaa atccatctgc      60
tctctgggct gtgatctgcc tcagacccac agcctgggtc ataggagggc cttgatactc     120
ctggcacaaa tgcaaagaat ctctcttccc tcctgcctga aggacaggca tgactttgca     180 ttccccagg aggagtttga tggcaaccag ttccagaagg ctcaagccat ctctgtcctc      240
catgagatga tccagcagac cttcaatctc ttcagcacaa aggactcatc tgctgcttgg     300
gatgagaccc tcctagacaa attctacatt gaacttttcc agcaactgaa tgacctggaa     360
gcctgtgtga tacaggaggc tggggtagaa gagactcccc tgatgaatga ggactccatc     420
ctggctgtga ggaaatactt ccaaagaatc actctctatc tgatggagaa gaaatacagc     480
ccttgtgcct gggaggttgt cagagcagaa atgatgagat ccttctcttt ttcaacaacc     540
ttacaagaaa gattaaggag gaagtaatga                                      570

<210> SEQ ID NO 32
<211> LENGTH: 188
<212> TYPE: PRT
<213> ORGANISM: Macaca mulatta

<400> SEQUENCE: 32

Met Ala Leu Ser Phe Ser Leu Leu Met Ala Val Val Val Leu Ser Tyr
  1               5                  10                  15

Lys Ser Ile Cys Ser Leu Gly Cys Asp Leu Pro Gln Thr His Ser Leu
             20                  25                  30

Gly His Arg Arg Ala Leu Ile Leu Leu Ala Gln Met Gln Arg Ile Ser
         35                  40                  45

Leu Pro Ser Cys Leu Lys Asp Arg His Asp Phe Ala Phe Pro Gln Glu
     50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser

```
                        85                  90                  95
Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Ile Gln Glu Ala Gly
            115                 120                 125

Val Glu Glu Thr Pro Leu Met Asn Glu Asp Ser Ile Leu Ala Val Arg
            130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Thr Leu Gln Glu Arg Leu Arg Arg Lys
                180                 185

<210> SEQ ID NO 33
<211> LENGTH: 570
<212> TYPE: DNA
<213> ORGANISM: Macaca mulatta

<400> SEQUENCE: 33
atggccctgt cctttctttt actgatggcc gtggtggtgc tcaactacaa atccatctgc      60
tctctgggct gtgatctgcc tcagacccac agcctgggtc ataggagggc cttgatactc     120
ctggcacaaa tgcaaagaat ctctcttccc tcctgcctga aggacaggca tgactttgca     180
ttcccccagg aggagtttga tggcaaccag ttccagaagg ctcaagccat ctctgtcctc     240
catgagatga tccagcagac cttcaatctc ttcagcacaa aggactcatc tgctgcttgg     300
gatgagaccc tcctagacaa atttacatt gaacttttcc agcaactgaa tgacctggaa      360
gcctgtgtga tacaggaggc tggggtagaa gagactcccc tgatgaatga ggactccatc     420
ctggctgtga ggaaatactt ccaaagaatc actctctatc tgacggagaa gaaatacagc     480
ccatgtgcct gggaggttgt cagagcagaa atcatgagat ccctctcttt ttcaacaaac     540
ttgcaaaaaa gattaaggag gaaggattga                                     570

<210> SEQ ID NO 34
<211> LENGTH: 189
<212> TYPE: PRT
<213> ORGANISM: Macaca mulatta

<400> SEQUENCE: 34

Met Ala Leu Ser Phe Ser Leu Leu Met Ala Val Val Val Leu Asn Tyr
1               5                   10                  15

Lys Ser Ile Cys Ser Leu Gly Cys Asp Leu Pro Gln Thr His Ser Leu
                20                  25                  30

Gly His Arg Arg Ala Leu Ile Leu Leu Ala Gln Met Gln Arg Ile Ser
            35                  40                  45

Leu Pro Ser Cys Leu Lys Asp Arg His Asp Phe Ala Phe Pro Gln Glu
        50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Ile Gln Glu Ala Gly
            115                 120                 125
```

```
Val Glu Glu Thr Pro Leu Met Asn Glu Asp Ser Ile Leu Ala Val Arg
            130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 35
<211> LENGTH: 570
<212> TYPE: DNA
<213> ORGANISM: Macaca mulatta

<400> SEQUENCE: 35

```
atggccctgt cctttcttt actgatggcc gtggtggtgc tcaactacaa atccatctgc      60
tctctgggct gtgatcctcc ccagacccac agcctgggtc ataggagggc cttgatactc     120
ctggcacaaa tgggaagaat ctctcctttc cctgtctga aggacagacg tgactttgga     180
ttcccccagg aggagtttga tgcaaccag ttccagaagg ctcaagccat gtctgtcctc     240
catgagatga tccagcagac cttcaatctc ttcagcacaa aggactcatc tgctgcttgg     300
gaacagaacc tcctagaaaa attttccgct gagctttacc agcaactgaa tgccttggaa     360
gcctgtgtga tagcagagcc tgggatggaa gagactctct tgatgaatga ggactccatc     420
ctggctatga gaaaatactt ccaaagaatc actctctatc taacggagaa gaagtacagc     480
ccttgtgcct gggaggttgt cagagcagaa atcatgagat ccctctcttt ttcaacaaac     540
ttgcaaagaa aattaaggag gaaggattga                                     570
```

<210> SEQ ID NO 36
<211> LENGTH: 189
<212> TYPE: PRT
<213> ORGANISM: Macaca mulatta

<400> SEQUENCE: 36

```
Met Ala Leu Ser Phe Ser Leu Leu Met Ala Val Val Val Leu Asn Tyr
1               5                   10                  15

Lys Ser Ile Cys Ser Leu Gly Cys Asp Pro Pro Gln Thr His Ser Leu
            20                  25                  30

Gly His Arg Arg Ala Leu Ile Leu Leu Ala Gln Met Gly Arg Ile Ser
        35                  40                  45

Pro Phe Ser Cys Leu Lys Asp Arg Arg Asp Phe Gly Phe Pro Gln Glu
    50                  55                  60

Glu Phe Asp Gly Asn Gln Phe Gln Lys Ala Gln Ala Met Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Ala Leu Glu Ala Cys Val Ile Ala Glu Pro Gly
        115                 120                 125

Met Glu Glu Thr Leu Leu Met Asn Glu Asp Ser Ile Leu Ala Met Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175
```

Phe Ser Thr Asn Leu Gln Arg Lys Leu Arg Arg Lys Asp
        180                 185

<210> SEQ ID NO 37
<211> LENGTH: 570
<212> TYPE: DNA
<213> ORGANISM: Macaca mulatta

<400> SEQUENCE: 37
atggccctgt cctttctttt actggtggcc gtggtggtgc tcagctacaa atccatctgc      60
tctctgggct gtgatctgcc tcggacccac agcctgggtc ataggaggtc cttgatactc     120
ctggcacaaa tgggaagaat ctctcctttc tcctgtctga aggacagaca tgactttgga     180
ttcccccagg aggagtttga tggcaaccag ttccacaagg ctcaagccat ctctgtcctc     240
catgagatga tccagcagac cttcaatctc ttcagcacaa aggactcatc tgctgcttgg     300
gaacacagcc tcctagaaaa attttccact ggactttacc agcaactgaa tgacctggaa     360
gcctgtgtga tacaggaggt tggagtggaa gagactccac tgacgaatgt ggactgcatc     420
ctggctgtga ggaaatactt ccaaagaatc accctctatc tgatggagaa gaaatacagc     480
ccttgtgcct gggaggttgt cagagcagaa atcatgagat ccttctcttt tttcacaacc     540
ttacaagaaa gattaaggag gaagtaatga                                      570

<210> SEQ ID NO 38
<211> LENGTH: 188
<212> TYPE: PRT
<213> ORGANISM: Macaca mulatta

<400> SEQUENCE: 38

Met Ala Leu Ser Phe Ser Leu Leu Val Ala Val Val Leu Ser Tyr
 1               5                  10                  15

Lys Ser Ile Cys Ser Leu Gly Cys Asp Leu Pro Arg Thr His Ser Leu
                20                  25                  30

Gly His Arg Arg Ser Leu Ile Leu Leu Ala Gln Met Gly Arg Ile Ser
            35                  40                  45

Pro Phe Ser Cys Leu Lys Asp Arg His Asp Phe Gly Phe Pro Gln Glu
        50                  55                  60

Glu Phe Asp Gly Asn Gln Phe His Lys Ala Gln Ala Ile Ser Val Leu
    65                  70                  75                  80

His Glu Met Ile Gln Gln Thr Phe Asn Leu Phe Ser Thr Lys Asp Ser
                85                  90                  95

Ser Ala Ala Trp Glu His Ser Leu Leu Glu Lys Phe Ser Thr Gly Leu
            100                 105                 110

Tyr Gln Gln Leu Asn Asp Leu Glu Ala Cys Val Ile Gln Glu Val Gly
        115                 120                 125

Val Glu Glu Thr Pro Leu Thr Asn Val Asp Cys Ile Leu Ala Val Arg
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Phe Thr Thr Leu Gln Glu Arg Leu Arg Arg Lys
            180                 185

<210> SEQ ID NO 39
<211> LENGTH: 570
<212> TYPE: DNA

-continued

<213> ORGANISM: Macaca mulatta

<400> SEQUENCE: 39

```
atggccctgt cctttctctt actggtggcc gtggtggtgc tcagctacaa atccatctgc    60
tctctgggct gtgatctgcc tcggacccac agcctgggtc ataggagggc cttgatactc   120
ctggcacaaa tgggaaggat ctctcctttc tcctgtctga aggacagaca tgactttgga   180
ttcccccagg aggagtttga tggcaaccag ttccagaagg ctcaagccat ctctgtcctc   240
catgagatga tccagcagac cttcaatctc ttcagcacaa aggactcatc tgctgcttgg   300
gaacagaacc tcctagaaaa attttccact ggactttacc agcaactgaa tgacctggaa   360
gcctgtgtga tacaggaggt tggagtggaa agagactcca ctgacgaatgt ggactgcatc   420
ctggctgtga ggaaatactt ccaaagaatc accctctatc tgatggagaa gaaatacagc   480
ccttgtgcct gggaggttgt cagagcagaa atcatgagat ccttctcttt ttcaacaacc   540
ttacaagaaa gattaaggag gaagtaatga                                    570
```

<210> SEQ ID NO 40
<211> LENGTH: 188
<212> TYPE: PRT
<213> ORGANISM: Macaca mulatta

<400> SEQUENCE: 40

```
Met Ala Leu Ser Phe Ser Leu Leu Val Ala Val Val Val Leu Ser Tyr
  1               5                  10                  15

Lys Ser Ile Cys Ser Leu Gly Cys Asp Leu Pro Arg Thr His Ser Leu
             20                  25                  30

Gly His Arg Arg Ala Leu Ile Leu Leu Ala Gln Met Gly Arg Ile Ser
         35                  40                  45

Pro Phe Ser Cys Leu Lys Asp Arg His Asp Phe Gly Phe Pro Gln Glu
     50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Trp Glu Gln Asn Leu Leu Glu Lys Phe Ser Thr Gly Leu
            100                 105                 110

Tyr Gln Gln Leu Asn Asp Leu Glu Ala Cys Val Ile Gln Glu Val Gly
        115                 120                 125

Val Glu Glu Thr Pro Leu Thr Asn Val Asp Cys Ile Leu Ala Val Arg
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Thr Leu Gln Glu Arg Leu Arg Arg Lys
            180                 185
```

<210> SEQ ID NO 41
<211> LENGTH: 752
<212> TYPE: DNA
<213> ORGANISM: Macaca fascicularis

<400> SEQUENCE: 41

```
agcaaagtct tcagaaaacc tagaggccaa ggttcaaggt tacccacctc agtagcctag    60
caatatttgc aacatcccaa tggccctgtc ctttctctta ctgatggccg tggtggtgct   120
```

```
cagctacaaa tccatctgct ctctgggctg tgatcctccc cagacccaca gcctgggtca    180
taggagggcc ttgatactcc tggcacaaat gggaagaatc tctcctttct cctgtctgaa    240
ggacagacat gactttggat tcccccagga ggagtttgat ggcaaccagt tccagaaggc    300
tcaagccatc tctgtcctcc atgagatgat ccagcagacc ttcaatctct tcagcacaaa    360
ggactcatct gctgcttggg aacagaacct cctagaaaaa ttttccgctg agctttacca    420
gcaactgaat gccttggaag cctgtgtgat agcagagcct gggatggaag agactctctt    480
gatgaatgag gattccatcc tggctgtgaa gaaatacttc aaagaatca ctctctatct     540 gacggagaag aagtacagcc cctgtgcctg ggaggttgtc agagcagaaa tcatgagatc    600
cctctctttt tcaacaaact tgcaaagaaa attaaggagg aaggattgaa aactggttca    660
acatggaaat gatcctcatt gacggacatg tcatctcaca ctttcatgag ttcttccatt    720
tcaaagactc atgactctta taaccacgaa tc                                  752
```

<210> SEQ ID NO 42
<211> LENGTH: 189
<212> TYPE: PRT
<213> ORGANISM: Macaca fascicularis
<400> SEQUENCE: 42

```
Met Ala Leu Ser Phe Ser Leu Leu Met Ala Val Val Leu Ser Tyr
1               5                   10                  15

Lys Ser Ile Cys Ser Leu Gly Cys Asp Pro Pro Gln Thr His Ser Leu
            20                  25                  30

Gly His Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Ala Leu Glu Ala Cys Val Ile Ala Glu Pro Gly
        115                 120                 125

Met Glu Glu Thr Leu Leu Met Asn Glu Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Arg Lys Leu Arg Arg Lys Asp
            180                 185
```

<210> SEQ ID NO 43
<211> LENGTH: 731
<212> TYPE: DNA
<213> ORGANISM: Macaca fascicularis
<400> SEQUENCE: 43

```
cactatttaa gatccatgca cagagcaagg tcttcaggaa acctagaggc caaggttcaa     60
ggttacccac ctcacgtagc ctagcaatat tgacaacatc ccaatggccc tgtccttttc    120
tttactgatg gccgtggtgg tgctcagcta caaatccatc tgctctctgg gctgtgatct    180
```

```
tcctcagacc cacagcctgg gtcataggag ggccttgata ctcctggcac aaatgggaag    240
gatctctccg ttctcctgtc tgaaggacag acgtgacttt gcattccccc aggaggagtt    300
tgatggcaac cagttccaga aggctcaagc catgtctgtc ctccatgaga tgatccagca    360
gaccttcaat ctcttcagca caaaggactc atctgctgct gggaacagaa acctcctaga    420
aaaattttcc gctgagcttt accagcaact gaatgacctg aaagcctgtg tgatagcaga    480
gcctgggatg gaagacactc ccttgatgaa tgaggactcc atcctggctg tgaagaaata    540
cttccaaaga atcactctct atctgacgga aagaaatac agcccttgtg cctgggaggt    600
tgtcagaaca gaaatcatga gatccctctc tttttcaaca aacttgcaaa aaagattaag    660
gaggaaggat tgaaaactgg ttcaacatgg aaatgatccg aattctgcag atatccatca    720
cactggcggc c                                                         731

<210> SEQ ID NO 44
<211> LENGTH: 189
<212> TYPE: PRT
<213> ORGANISM: Macaca fascicularis

<400> SEQUENCE: 44

Met Ala Leu Ser Phe Ser Leu Leu Met Ala Val Val Leu Ser Tyr
 1               5                  10                  15

Lys Ser Ile Cys Ser Leu Gly Cys Asp Leu Pro Gln Thr His Ser Leu
                20                  25                  30

Gly His Arg Arg Ala Leu Ile Leu Leu Ala Gln Met Gly Arg Ile Ser
            35                  40                  45

Pro Phe Ser Cys Leu Lys Asp Arg Arg Asp Phe Ala Phe Pro Gln Glu
        50                  55                  60

Glu Phe Asp Gly Asn Gln Phe Gln Lys Ala Gln Ala Met Ser Val Leu
    65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Asp Leu Lys Ala Cys Val Ile Ala Glu Pro Gly
        115                 120                 125

Met Glu Asp Thr Pro Leu Met Asn Glu Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Thr Glu Ile Met Arg Ser Leu Ser
                165                 170                 175

Phe Ser Thr Asn Leu Gln Lys Arg Leu Arg Arg Lys Asp
            180                 185

<210> SEQ ID NO 45
<211> LENGTH: 846
<212> TYPE: DNA
<213> ORGANISM: Macaca fascicularis
<220> FEATURE:
<221> NAME/KEY: modified_base
<222> LOCATION: (844)..(844)
<223> OTHER INFORMATION: a, c, g, t, unknown or other

<400> SEQUENCE: 45
gatccatgca cggagcaaag tcttcagaaa acctagaggc caagtttcaa ggttacccac    60
ctcaagtagc ctagcaatat tgacaacatc ccaatggccc tgtccttttc tttactgatg   120
```

```
gccgtggtgg tgctcaacta caaatccatc tgctctctgg gctgtgatct gcctcggacc        180
cacagcctgg gtcataggag ggccttgata ctcctggcac aaatgggaag aatctctcct        240
ttctcctgtc tgaaggacag acatgacttt ggattccccc aggaggagtt tgatggcaac        300
cagttccaga aggctcaagc catctctgtc tccatgaga tgatccagca gaccttcaat         360
ctcttcagca caaaggactc atctgctgct tgggaacaga acctcctaga aaaattttcc        420
gctgagcttt accagcaact gaatgacctg aaagcctgtg tgatagcaga gcctgggatg        480
gaagacactc ccttgatgaa tgaggactcc atcctggctg tgaagaaata cttccaaaga        540
atcactctct atctgacgga gaagaaatac agcccatgtg cctgggaggt tgtcagaaca        600
gaaatcatga gatccctctc tttttcaaca aacttgcaaa aaagattaag gaggaaggat        660
tgaaaactgg ttcaacatgg aaatgatccg aattctgcag atatccatca cactggcggc        720
cgctcgagca tgcatctaga gggcccctat tctatagtgt cacctaaatg ctagagctcg        780
ctgatcagcc tcgactgggc cttctaattg ccagccatct gttgtttgcc cctcccccgt        840
gccntc                                                                   846

<210> SEQ ID NO 46
<211> LENGTH: 189
<212> TYPE: PRT
<213> ORGANISM: Macaca fascicularis

<400> SEQUENCE: 46

Met Ala Leu Ser Phe Ser Leu Leu Met Ala Val Val Leu Asn Tyr
1               5                   10                  15

Lys Ser Ile Cys Ser Leu Gly Cys Asp Leu Pro Arg Thr His Ser Leu
            20                  25                  30

Gly His Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

Tyr Gln Gln Leu Asn Asp Leu Lys Ala Cys Val Ile Ala Glu Pro Gly
        115                 120                 125

Met Glu Asp Thr Pro Leu Met Asn Glu Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Thr Glu Ile Met Arg Ser Leu Ser
                165                 170                 175

Phe Ser Thr Asn Leu Gln Lys Arg Leu Arg Arg Lys Asp
            180                 185

<210> SEQ ID NO 47
<211> LENGTH: 658
<212> TYPE: DNA
<213> ORGANISM: Macaca fascicularis

<400> SEQUENCE: 47
taggaattag cttggtaccc tagaggccaa ggttcaaggt tacccacctc aagtagccta        60
```

-continued

```
gcaatatttg caacatccca atggccctgt ccttttcttt actgatggcc gtggtggtgc    120
tcagctacaa atccatctgc tctctgggct gtgatcctcc ccggacccac agcctgggtc    180
ataggagggc cttgatactc ctggcacaaa tggaagaat ctctcctttc tcctgtctga     240
aggacagatg tgactttgca ttcccccagg aggagtttga tggcaaccag ttccagaagg    300
ctcaagccat gtctgtcctc catgagatga tccagcagac cttcaatctc ttcagcacaa    360
aggactcatc tgctgcttgg aacagaaacc tcctagaaaa attttccgct gagctttacc    420
agcaactgaa tgacctgaaa gctgtgtgta tagcagagcc tgggatggaa gagactctct    480
tgatgaatga ggactccatc ctggctgtga agaaatactt ccaaagaatc actctctatc    540
tgacggagaa aagtacagc ccctgtgcct gggaggttgt cagagcagaa atcatgagat     600
ccctctcttt ttcaacaaac ttgcaaaaaa gattaaggag aaggattga aagaattc       658
```

<210> SEQ ID NO 48
<211> LENGTH: 189
<212> TYPE: PRT
<213> ORGANISM: Macaca fascicularis

<400> SEQUENCE: 48

```
Met Ala Leu Ser Phe Ser Leu Leu Met Ala Val Val Leu Ser Tyr
  1               5                  10                  15
Lys Ser Ile Cys Ser Leu Gly Cys Asp Pro Arg Thr His Ser Leu
             20                  25                  30
Gly His Arg Arg Ala Leu Ile Leu Leu Ala Gln Met Glu Arg Ile Ser
         35                  40                  45
Pro Phe Ser Cys Leu Lys Asp Arg Cys Asp Phe Ala Phe Pro Gln Glu
     50                  55                  60
Glu Phe Asp Gly Asn Gln Phe Gln Lys Ala Gln Ala Met Ser Val Leu
 65                  70                  75                  80
His Glu Met Ile Gln Gln Thr Phe Asn Leu Phe Ser Thr Lys Asp Ser
                 85                  90                  95
Ser Ala Ala Trp Glu Gln Asn Leu Leu Glu Lys Phe Ser Ala Glu Leu
            100                 105                 110
Tyr Gln Gln Leu Asn Asp Leu Lys Ala Cys Val Ile Ala Glu Pro Gly
        115                 120                 125
Met Glu Glu Thr Leu Leu Met Asn Glu Asp Ser Ile Leu Ala Val Lys
    130                 135                 140
Lys Tyr Phe Gln Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Leu Ser
                165                 170                 175
Phe Ser Thr Asn Leu Gln Lys Arg Leu Arg Arg Lys Asp
            180                 185
```

<210> SEQ ID NO 49
<211> LENGTH: 841
<212> TYPE: DNA
<213> ORGANISM: Macaca fascicularis
<220> FEATURE:
<221> NAME/KEY: modified_base
<222> LOCATION: (13)..(13)
<223> OTHER INFORMATION: a, c, g, t, unknown or other

<400> SEQUENCE: 49

```
tcagacgtgg ttnaagtttt tttcttccat ttcaggtgtc gtgaggcagt atgttcacta    60 tttaacaccct atgcacagag caaggtcttc agaaaactta cagcccaggg ttcagggtta   120
```

```
ctcctcatca accagcccag cagcatcttc aggattccca atggcattgc cctttgcttt      180
aatgatggcc ctgctggtgc ttagctacaa gtcaagctgc tctctgggct gtaatccatc      240
tcaaacccac aacatgaata acaggaggac tttgatgctc atggcacaaa tgaggagaat      300
ctctcctttt tcatgcctga aggacagaaa tgactttgaa tttccccagg aggagtttga      360
tggcaaccag ttccagaata ctcaagccat ctctgtcctc catgagatga tgcagcagac      420
cttcaatctc ttcagcacaa aggactcatc tgctgcttgg gatgagaccc tcctagacaa      480
attctacatt gaacttttcc agcaactgaa tgacctggaa gcctgtgtga tacaggaggc      540
tggggtagaa gagactcccc tgatgaatga ggactccatc ctggctgtga ggaaatactt      600
ccaaagaatc actctctatc tgatggagaa gaaatacagc ccttgtgcct gggaggttgt      660
cagagcagaa atcatgagat ccctctcttt tcaacaaac ttgcaaaaaa gattaaggag      720
gaaggattga aaactggttc aacatggaaa tgatcctcat tgactataca tcatctcaca      780
ctttcatgag ttcttccatt tcaaagactc atgtctctta taaccaccac gagtggaatt      840
c                                                                    841
```

<210> SEQ ID NO 50
<211> LENGTH: 189
<212> TYPE: PRT
<213> ORGANISM: Macaca fascicularis

<400> SEQUENCE: 50

```
Met Ala Leu Pro Phe Ala Leu Met Met Ala Leu Leu Val Leu Ser Tyr
  1               5                  10                  15

Lys Ser Ser Cys Ser Leu Gly Cys Asn Pro Ser Gln Thr His Asn Met
                 20                  25                  30

Asn Asn Arg Arg Thr Leu Met Leu Met Ala Gln Met Arg Arg Ile Ser
             35                  40                  45

Pro Phe Ser Cys Leu Lys Asp Arg Asn Asp Phe Glu Phe Pro Gln Glu
         50                  55                  60

Glu Phe Asp Gly Asn Gln Phe Gln Asn Thr Gln Ala Ile Ser Val Leu
 65                  70                  75                  80

His Glu Met Met Gln Gln Thr Phe Asn Leu Phe Ser Thr Lys Asp Ser
                 85                  90                  95

Ser Ala Ala Trp Asp Glu Thr Leu Leu Asp Lys Phe Tyr Ile Glu Leu
                100                 105                 110

Phe Gln Gln Leu Asn Asp Leu Glu Ala Cys Val Ile Gln Glu Ala Gly
            115                 120                 125

Val Glu Glu Thr Pro Leu Met Asn Glu Asp Ser Ile Leu Ala Val Arg
        130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185
```

<210> SEQ ID NO 51
<211> LENGTH: 756
<212> TYPE: DNA
<213> ORGANISM: Macaca fascicularis

<400> SEQUENCE: 51

```
gtacccagag atagaaagta aaaactaggg catttagaaa atggaaatta ttatgttcac       60
```

```
tatttaagac ccatgcacag agcaaagtct tcagaaaacc tagaggccaa ggttcaaggt      120
tacccacctc acgtagccta gcaatatttg caacatccca atggccctgt ccttttcttt      180
actgatggcc gtggtggtgc tcagctacaa atccatctgc tctctgggct gtgatctgcc      240
tcagacccac agcctgggtc ataggagggc cttgatactc ctggcacaaa tgcaaagaat      300
ctctcttccc tcctgcctga aggacaggca tgactttgca ttcctccagg agtttgatgg      360
caaccagttc cagaaggctc aagccatgtc tgtcctccat gagatgatcc agcagacctt      420
caatctcttg agcacaaagg actcatctgc tgcttgggat gagaccctcc tagacaaatt      480
ctacattgaa cttttccagc aactgaatga cttggaagcc tgtgtgatac aggaggctgg      540
ggtagaagag actcccctga tgaatgagga ctccatcctg gctgtgagga aatacttcca      600
aagaatcact ctctatctga cggagaagaa atacagccct tgtgcctggg aggttgtcag      660
agcagaaatc atgagatccc tctcttttc aacaaacttg caaaaagat tagggaggaa       720 ggattgaaaa ctggttcaac acggaaatga gaattc                                756
```

<210> SEQ ID NO 52  
<211> LENGTH: 188  
<212> TYPE: PRT  
<213> ORGANISM: Macaca fascicularis

<400> SEQUENCE: 52

```
Met Ala Leu Ser Phe Ser Leu Leu Met Ala Val Val Leu Ser Tyr
 1               5                  10                  15

Lys Ser Ile Cys Ser Leu Gly Cys Asp Leu Pro Gln Thr His Ser Leu
                20                  25                  30

Gly His Arg Arg Ala Leu Ile Leu Leu Ala Gln Met Gln Arg Ile Ser
            35                  40                  45

Leu Pro Ser Cys Leu Lys Asp Arg His Asp Phe Ala Phe Leu Gln Glu
        50                  55                  60

Phe Asp Gly Asn Gln Phe Gln Lys Ala Gln Ala Met Ser Val Leu His
    65                  70                  75                  80

Glu Met Ile Gln Gln Thr Phe Asn Leu Leu Ser Thr Lys Asp Ser Ser
                85                  90                  95

Ala Ala Trp Asp Glu Thr Leu Leu Asp Lys Phe Tyr Ile Glu Leu Phe
            100                 105                 110

Gln Gln Leu Asn Asp Leu Glu Ala Cys Val Ile Gln Glu Ala Gly Val
        115                 120                 125

Glu Glu Thr Pro Leu Met Asn Glu Asp Ser Ile Leu Ala Val Arg Lys
    130                 135                 140

Tyr Phe Gln Arg Ile Thr Leu Tyr Leu Thr Glu Lys Lys Tyr Ser Pro
145                 150                 155                 160

Cys Ala Trp Glu Val Val Arg Ala Glu Ile Met Arg Ser Leu Ser Phe
                165                 170                 175

Ser Thr Asn Leu Gln Lys Arg Leu Gly Arg Lys Asp
            180                 185
```

<210> SEQ ID NO 53  
<211> LENGTH: 823  
<212> TYPE: DNA  
<213> ORGANISM: Macaca fascicularis  
<220> FEATURE:  
<221> NAME/KEY: modified_base  
<222> LOCATION: (13)..(13)  
<223> OTHER INFORMATION: a, c, g, t, unknown or other  
<220> FEATURE:  
<221> NAME/KEY: modified_base  
<222> LOCATION: (37)..(37)

<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (814)..(814)
<223> OTHER INFORMATION: a, c, g, t, unknown or other

<400> SEQUENCE: 53

```
agcctcagac agnggtcaaa gttttttct  tccattncag gngtcggtga ggaattagct    60
tggtacccag gagatagaaa agtaaaacta gagcctttag aaaatggaaa ttagtatgtt   120
cactatttaa gatccatgca cagagcaagg tcttcaggaa acctggaggc caaggttcaa   180
ggttacccac ctcagtagcc tagcaatatt tgcaacatcc caatggccct gtcctttct   240
ttactggtgg ccgtggtggt gctcagctac aaatccatct gctctctggg ctgtgatctg   300
cctcgaaccc acagcctggg tcataggagg gccttgatac tcctggcaca atgggaaga   360
atctctcctt tctcctgtct gaaggacaga catgactttg gattccccca ggaggagttt   420
gatggcaacc agttccagaa ggctcaagcc atctctgtcc tccatgagat gatccagcag   480
accttcaatc tcttcagcac aaaggactca tctgctgctt gggaacacag cctcctagaa   540
aaatttccg  ctgagcttta ccagcaactg aatgacctgg aagcctgtgt gatacaggag   600
gttggagtgg aagagactcc actgacgaat gtggactgca tcctggctgt gaagaaatac   660
ttccaaagaa tcaccctcta tctgatggag aagaaataca gcccttgtgc ctgggaggtt   720
gtcagagcag aaatcatgag atccttctct ttttcaacaa ccttacaaga aagattaagg   780
aggaagtaat gaaagctggt tcaacacgga aatnagaatt act                     823
```

<210> SEQ ID NO 54
<211> LENGTH: 188
<212> TYPE: PRT
<213> ORGANISM: Macaca fascicularis

<400> SEQUENCE: 54

```
Met Ala Leu Ser Phe Ser Leu Leu Val Ala Val Val Leu Ser Tyr
 1               5                  10                  15

Lys Ser Ile Cys Ser Leu Gly Cys Asp Leu Pro Arg Thr His Ser Leu
                20                  25                  30

Gly His Arg Arg Ala Leu Ile Leu Leu Ala Gln Met Gly Arg Ile Ser
             35                  40                  45

Pro Phe Ser Cys Leu Lys Asp Arg His Asp Phe Gly Phe Pro Gln Glu
         50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Trp Glu His Ser Leu Leu Glu Lys Phe Ser Ala Glu Leu
                100                 105                 110

Tyr Gln Gln Leu Asn Asp Leu Glu Ala Cys Val Ile Gln Glu Val Gly
            115                 120                 125

Val Glu Glu Thr Pro Leu Thr Asn Val Asp Cys Ile Leu Ala Val Lys
        130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175
```

Phe Ser Thr Thr Leu Gln Glu Arg Leu Arg Arg Lys
        180                 185

<210> SEQ ID NO 55
<211> LENGTH: 962
<212> TYPE: DNA
<213> ORGANISM: Macaca fascicularis
<220> FEATURE:
<221> NAME/KEY: modified_base
<222> LOCATION: (6)..(7)
<223> OTHER INFORMATION: a, c, g, t, unknown or other
<220> FEATURE:
<221> NAME/KEY: modified_base
<222> LOCATION: (741)..(741)
<223> OTHER INFORMATION: a, c, g, t, unknown or other
<220> FEATURE:
<221> NAME/KEY: modified_base
<222> LOCATION: (818)..(818)
<223> OTHER INFORMATION: a, c, g, t, unknown or other
<220> FEATURE:
<221> NAME/KEY: modified_base
<222> LOCATION: (835)..(835)
<223> OTHER INFORMATION: a, c, g, t, unknown or other
<220> FEATURE:
<221> NAME/KEY: modified_base
<222> LOCATION: (837)..(837)
<223> OTHER INFORMATION: a, c, g, t, unknown or other
<220> FEATURE:
<221> NAME/KEY: modified_base
<222> LOCATION: (845)..(845)
<223> OTHER INFORMATION: a, c, g, t, unknown or other
<220> FEATURE:
<221> NAME/KEY: modified_base
<222> LOCATION: (850)..(850)
<223> OTHER INFORMATION: a, c, g, t, unknown or other
<220> FEATURE:
<221> NAME/KEY: modified_base
<222> LOCATION: (878)..(878)
<223> OTHER INFORMATION: a, c, g, t, unknown or other
<220> FEATURE:
<221> NAME/KEY: modified_base
<222> LOCATION: (899)..(899)
<223> OTHER INFORMATION: a, c, g, t, unknown or other
<220> FEATURE:
<221> NAME/KEY: modified_base
<222> LOCATION: (906)..(906)
<223> OTHER INFORMATION: a, c, g, t, unknown or other
<220> FEATURE:
<221> NAME/KEY: modified_base
<222> LOCATION: (915)..(915)
<223> OTHER INFORMATION: a, c, g, t, unknown or other
<220> FEATURE:
<221> NAME/KEY: modified_base
<222> LOCATION: (918)..(918)
<223> OTHER INFORMATION: a, c, g, t, unknown or other
<220> FEATURE:
<221> NAME/KEY: modified_base
<222> LOCATION: (920)..(920)
<223> OTHER INFORMATION: a, c, g, t, unknown or other
<220> FEATURE:
<221> NAME/KEY: modified_base
<222> LOCATION: (928)..(928)
<223> OTHER INFORMATION: a, c, g, t, unknown or other
<220> FEATURE:
<221> NAME/KEY: modified_base
<222> LOCATION: (932)..(932)
<223> OTHER INFORMATION: a, c, g, t, unknown or other
<220> FEATURE:
<221> NAME/KEY: modified_base
<222> LOCATION: (935)..(935)
<223> OTHER INFORMATION: a, c, g, t, unknown or other
<220> FEATURE:
<221> NAME/KEY: modified_base
<222> LOCATION: (962)..(962)
<223> OTHER INFORMATION: a, c, g, t, unknown or other

<400> SEQUENCE: 55

```
cttcannaca agtaaaacta gagcctttag aaaatggaaa ttagtatgtt cactatttaa      60
gacccatgca cagagcaaag tcttcagaaa acctagaggc caaggttcaa ggttacccac     120
ctcacgtagc ctagcaatat tgacaacatc ccaatggccc tgtccttttc tttactgatg     180
gccgtggtgg tgctcagcta caaatccatc tgctctctgg gctgtgatct tcctcagacc     240
cacagcctgg gtcataggag ggccttgata ctcctggcac aaatgggaag gatctctccg     300
ttctcctgtc tgaaggacag acatgacttt ggattccccc aggaggagtt tgatggcaac     360
cagttccaga aggctcaagc catgtctgtc ctccatgaga tgatccagca gaccttcaat     420
ctcttcagca caaggactc atctgctgct tgggaacaga acctcctaga aaaattttcc      480
gctgagcttt accagcaact gaatgacctg aaagcctgtg tgatagcaga gcctgggatg     540
gaagacactc ccttgatgaa tgaggactcc atcctggctg tgaagaaata cttccaaaga     600
atcactctct atctgacgga gaagaagtac agccctgtg cctgggaggt tgtcagagca     660
gaaatcatga gatccctctc tttttcaaca aacttgcaaa aaagattaag gaggaaggat     720
tgaaaactgg ttcaacacgg naaatgaaaa ttctgcagat atccatcaca ctggcggccg     780
ctcgagcatg catctaaagg gccctattct taagtgtnac ctaaatgcta aagcncnctg     840
atcancctcn atgtgccttt taattgcccg ccatctgntg ttggcccctc cccgggccnt     900
tcttgnacct ggaanggncn ctcccatngt cnttnctaaa aaagaaaaa ttgcctccca     960 tn                                                                    962
```

<210> SEQ ID NO 56
<211> LENGTH: 189
<212> TYPE: PRT
<213> ORGANISM: Macaca fascicularis

<400> SEQUENCE: 56

```
Met Ala Leu Ser Phe Ser Leu Leu Met Ala Val Val Leu Ser Tyr
  1               5                  10                  15

Lys Ser Ile Cys Ser Leu Gly Cys Asp Leu Pro Gln Thr His Ser Leu
                 20                  25                  30

Gly His Arg Arg Ala Leu Ile Leu Leu Ala Gln Met Gly Arg Ile Ser
             35                  40                  45

Pro Phe Ser Cys Leu Lys Asp Arg His Asp Phe Gly Phe Pro Gln Glu
         50                  55                  60

Glu Phe Asp Gly Asn Gln Phe Gln Lys Ala Gln Ala Met Ser Val Leu
     65                  70                  75                  80

His Glu Met Ile Gln Gln Thr Phe Asn Leu Phe Ser Thr Lys Asp Ser
                 85                  90                  95

Ser Ala Ala Trp Glu Gln Asn Leu Leu Glu Lys Phe Ser Ala Glu Leu
            100                 105                 110

Tyr Gln Gln Leu Asn Asp Leu Lys Ala Cys Val Ile Ala Glu Pro Gly
        115                 120                 125

Met Glu Asp Thr Pro Leu Met Asn Glu Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 57

```
<211> LENGTH: 815
<212> TYPE: DNA
<213> ORGANISM: Macaca fascicularis
<220> FEATURE:
<221> NAME/KEY: modified_base
<222> LOCATION: (792)..(792)
<223> OTHER INFORMATION: a, c, g, t, unknown or other

<400> SEQUENCE: 57
aagacgttca gaaatggaa gctagtatgt tccctattta aaacctatgc acagagcaag      60
gtcttcagaa aacttacagc ccagggttca gggttactcc tcatcaacca gcccagcagc    120
atcttcagga ttcccaatgg cattgccctt tgctttaatg atggccctgc tggtgcttag    180
ctacaagtca agctgctctc tgggctgtaa tccgtctcaa acccacaaca tgaataacag    240
gaggactttg atgctcatgg cacaaatgag gagaatctct ccttttcat gcctgaagga     300 cagaaatgac tttgaattc cccaggagga gtttgatggc aaccagttcc agaatactca     360
agccatctct gtcctccatg agatgatcca gcagaccttc aatctcttca gcacaaagga    420
ctcatctgct gcttgggatg agaccctcct agacaaattc tacattgaac ttttccagca    480
actgaatgac ctggaagcct gtgtgataca ggaggctggg gtagaagaga ctcccctgat    540
gaatgaggac tccatcctgg ctgtgaagaa atacttccaa agaatcactc tctatctgat    600
ggagaagaaa tacagccctt gtgcctggga ggttgtcaga gcagaaatca tgagatccct    660
ctctttttca acaaacttgc aaaaaagatt aaggaggaag gattgaaaac tggttcaaca    720
tggaaatgat cctcattgac tatacatcat ctcacacttt aatgagttct tccatttcaa    780
agactcatgt cncttataac caccacgagt tgaga                               815

<210> SEQ ID NO 58
<211> LENGTH: 189
<212> TYPE: PRT
<213> ORGANISM: Macaca fascicularis

<400> SEQUENCE: 58

Met Ala Leu Pro Phe Ala Leu Met Met Ala Leu Leu Val Leu Ser Tyr
  1               5                  10                  15

Lys Ser Ser Cys Ser Leu Gly Cys Asn Pro Ser Gln Thr His Asn Met
             20                  25                  30

Asn Asn Arg Arg Thr Leu Met Leu Met Ala Gln Met Arg Arg Ile Ser
         35                  40                  45

Pro Phe Ser Cys Leu Lys Asp Arg Asn Asp Phe Glu Phe Pro Gln Glu
     50                  55                  60

Glu Phe Asp Gly Asn Gln Phe Gln Asn Thr Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Ile Gln Glu Ala Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

180             185

<210> SEQ ID NO 59
<211> LENGTH: 774
<212> TYPE: DNA
<213> ORGANISM: Macaca fascicularis
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (22)..(22)
<223> OTHER INFORMATION: a, c, g, t, unknown or other
<220> FEATURE:
<221> NAME/KEY: modified_base
<222> LOCATION: (750)..(750)
<223> OTHER INFORMATION: a, c, g, t, unknown or other

<400> SEQUENCE: 59
aggctaatna cagcaaaatg gnaagtgagt atgttcccta tataaggccg tgtacaaacc      60
aaagtcttca gagatcctgg agcccaaagt taagggtcat ccatctgaac cagctcagca     120
gcatccgcaa catctacaat ggccttgacc ttttatttac tgatggccct agtggtgctc     180
agctacaagc cattcagctc tctgggctgt gatctgcctc agacccacag cctgggttac     240
aggaggccct tggtgctcct ggcacaaatg agaagaatct ctcctttctc ctgcctgaag     300
gacagacatg actttgaatt accccaggag gagtttgatg acaaaaactt ccagaaggct     360
caagccatct ctgtcctcca tgagataatc cagcagacct tcaacctctt caacacaaag     420
aattcatctg ctgctttcaa tgagacccct ctagatgaat tctacatcga acttgaccag     480
cagctgaatg acctggagtc ctgtgtgatg caggaagtgg gggtgacaga gactcacctg     540
atgtacgagg actccatcct ggctgtgaag aaatacttcc gaagaatcac tctctatctg     600
acagagaaga aatacagccc ttgtgcctgg gaggttgtca gagcagaaat catgagatcc     660
ttctcttat caatcaactt gcaaaaaaga ttgaagagta aggaataaga cctggtgcaa     720
catggaaatg attcttatag actaatatgn cagctcacac tccaaagcaa aaat           774

<210> SEQ ID NO 60
<211> LENGTH: 189
<212> TYPE: PRT
<213> ORGANISM: Macaca fascicularis

<400> SEQUENCE: 60

Met Ala Leu Thr Phe Tyr Leu Leu Met Ala Leu Val Val Leu Ser Tyr
 1               5                  10                  15

Lys Pro Phe Ser Ser Leu Gly Cys Asp Leu Pro Gln Thr His Ser Leu
            20                  25                  30

Gly Tyr Arg Arg Pro Leu Val Leu Leu Ala Gln Met Arg Arg Ile Ser
        35                  40                  45

Pro Phe Ser Cys Leu Lys Asp Arg His Asp Phe Glu Leu Pro Gln Glu
    50                  55                  60

Glu Phe Asp Asp Lys Asn Phe Gln Lys Ala Gln Ala Ile Ser Val Leu
65                  70                  75                  80

His Glu Ile Ile Gln Gln Thr Phe Asn Leu Phe Asn Thr Lys Asn Ser
                85                  90                  95

Ser Ala Ala Phe Asn Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Thr Glu Thr His Leu Met Tyr Glu Asp Ser Ile Leu Ala Val Lys
130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 61
<211> LENGTH: 946
<212> TYPE: DNA
<213> ORGANISM: Macaca fascicularis

<400> SEQUENCE: 61
gtcgaacaaa gaaagcaaaa acagtagata gaaagtaaaa ctaggcattt agaaatgga      60
aattagtatg ttcactattt aagatccatg cacggagcaa agtcttcaga aaacctagag    120
gccaaggttc aaggttaccc acctcaagta gcctagcaat atttgcaaca tcccaatggc    180
cctgtccttt tctttactga tggccgtggt ggtgctcagc tacaaatcca tctgctctct    240
gggctgtgat cctccccgga cccacagcct gggtcatagg agggccttga tactcctggc    300
acaaatggaa agaatctctc ctttctcctg tctgaaggac agacatgact ttggattccc    360
ccaggaggag tttgatggca accagttcca gaaggctcaa gccatctctg tcctccatga    420
gatgatccag cagaccttca atctcttcag cacaaaggac tcatctgctg cttgggaaca    480
gaacctccta gaaaattttt ccgctgagct ttaccagcaa ctgaatgcct tggaagcctg    540
tgtgatagca gagcctggga tggaagagac tctcttgatg aatgaggatt ccatcctggc    600
tgtgaagaaa tacttccaaa gaatcactct ctatctgacg gagaagaagt acagcccctg    660
tgcctgggag gttgtcagag cagaaatcat gagatccctc tcttttttcaa caaacttgca    720
aaaaagatta aggaggaagg attgaaaact agttcaacat ggaaatgatc ctcattgacg    780
gacatgtcat ctcacacttt catgagttct tccatttcaa agactcatga ctcttataac    840
caccacgagt tgaatcaaaa tgttcaaaag ttttcaggag tgtaaagaag catcgtgttc    900
gcctgtgcag gcactagtcc tttacagatg accacgctga gaattc                    946

<210> SEQ ID NO 62
<211> LENGTH: 189
<212> TYPE: PRT
<213> ORGANISM: Macaca fascicularis

<400> SEQUENCE: 62

Met Ala Leu Ser Phe Ser Leu Leu Met Ala Val Val Val Leu Ser Tyr
1               5                   10                  15

Lys Ser Ile Cys Ser Leu Gly Cys Asp Pro Pro Arg Thr His Ser Leu
            20                  25                  30

Gly His Arg Arg Ala Leu Ile Leu Leu Ala Gln Met Glu Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Trp Glu Gln Asn Leu Leu Glu Lys Phe Ser Ala Glu Leu
            100                 105                 110

```
Tyr Gln Gln Leu Asn Ala Leu Glu Ala Cys Val Ile Ala Glu Pro Gly
        115                 120                 125

Met Glu Glu Thr Leu Leu Met Asn Glu Asp Ser Ile Leu Ala Val Lys
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185
```

<210> SEQ ID NO 63
<211> LENGTH: 792
<212> TYPE: DNA
<213> ORGANISM: Macaca fascicularis
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (14)..(14)
<223> OTHER INFORMATION: a, c, g, t, unknown or other
<220> FEATURE:
<221> NAME/KEY: modified_base
<222> LOCATION: (660)..(660)
<223> OTHER INFORMATION: a, c, g, t, unknown or other
<220> FEATURE:
<221> NAME/KEY: modified_base
<222> LOCATION: (672)..(672)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other
<220> FEATURE:
<221> NAME/KEY: modified_base
<222> LOCATION: (704)..(704)
<223> OTHER INFORMATION: a, c, g, t, unknown or other
<220> FEATURE:
<221> NAME/KEY: modified_base
<222> LOCATION: (712)..(712)
<223> OTHER INFORMATION: a, c, g, t, unknown or other
<220> FEATURE:
<221> NAME/KEY: modified_base
<222> LOCATION: (738)..(738)
<223> OTHER INFORMATION: a, c, g, t, unknown or other
<220> FEATURE:
<221> NAME/KEY: modified_base
<222> LOCATION: (743)..(743)
<223> OTHER INFORMATION: a, c, g, t, unknown or other
<220> FEATURE:
<221> NAME/KEY: modified_base
<222> LOCATION: (758)..(758)
<223> OTHER INFORMATION: a, c, g, t, unknown or other
<220> FEATURE:
<221> NAME/KEY: modified_base
<222> LOCATION: (779)..(779)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (785)..(785)
<223> OTHER INFORMATION: a, c, g, t, unknown or other

<400> SEQUENCE: 63

```
tncaataccc tagncaacat tgacaacatc ccaatggccc tgtcctttc tttactgatg     60 gccgtggtgg tgctcagcta caaatccatc tgctctctgg gctgtgatct tcctcagacc    120
```

```
cacagcctgg gtcataggag ggccttgata ctcctggcac aaatgggaag gatctctccg    180
ttctcctgtc tgaaggacag gcatgacttt gcattccccc aggaggagtt tgatggcaac    240
cagttccaga aggctcaagc catctctgtc ctccatgaga tgatccagca gaccttcaat    300
ctcttcagca caaaggactc atctgctgct tgggaacaga acctcctaga aaattttcc     360 gctgagcttt accagcaact gaatgacctg aaagcctgtg tgatagcaga gcctgggatg    420
gaagacactc ccttgatgaa tgaggactcc atcctggctg tgaagaaata cttccaaaga    480
atcactctct atctgacgga gaagaaatac agcccttgtg cctgggaggt tgtcagagca    540
gaaatcatga gatccctctc tttttcaaca aacttgcaaa aaagattaag gaggaaggat    600
tgaaaactgg ttcaacatgg aaatgatcct tcattgacgg acatgtcatc tcacactttn    660
catgagttct tncatttnca aagactcctt tgaattctgc aganatccat cncactgggc    720
ggccgctcga gcatgccntc tanagggccc tattctanag tggcaccota aatgctaana    780 ccncncctga tc                                                        792
```

<210> SEQ ID NO 64
<211> LENGTH: 189
<212> TYPE: PRT
<213> ORGANISM: Macaca fascicularis

<400> SEQUENCE: 64

```
Met Ala Leu Ser Phe Ser Leu Leu Met Ala Val Val Leu Ser Tyr
 1               5                  10                  15
Lys Ser Ile Cys Ser Leu Gly Cys Asp Leu Pro Gln Thr His Ser Leu
             20                  25                  30
Gly His Arg Arg Ala Leu Ile Leu Leu Ala Gln Met Gly Arg Ile Ser
         35                  40                  45
Pro Phe Ser Cys Leu Lys Asp Arg His Asp Phe Ala Phe Pro Gln Glu
     50                  55                  60
Glu Phe Asp Gly Asn Gln Phe Gln Lys Ala Gln Ala Ile Ser Val Leu
 65                  70                  75                  80
His Glu Met Ile Gln Gln Thr Phe Asn Leu Phe Ser Thr Lys Asp Ser
                 85                  90                  95
Ser Ala Ala Trp Glu Gln Asn Leu Leu Glu Lys Phe Ser Ala Glu Leu
            100                 105                 110
Tyr Gln Gln Leu Asn Asp Leu Lys Ala Cys Val Ile Ala Glu Pro Gly
        115                 120                 125
Met Glu Asp Thr Pro Leu Met Asn Glu Asp Ser Ile Leu Ala Val Lys
    130                 135                 140
Lys Tyr Phe Gln Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Leu Ser
                165                 170                 175
Phe Ser Thr Asn Leu Gln Lys Arg Leu Arg Arg Lys Asp
            180                 185
```

<210> SEQ ID NO 65
<211> LENGTH: 750
<212> TYPE: DNA
<213> ORGANISM: Macaca fascicularis
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (8)..(8)

-continued

```
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other

<400> SEQUENCE: 65
gnctaatngg naaaatgtaa atgaatatgt tccctattta aggctaggca caaagcaagg      60
tcttcagaga acctagagcc taacatttag gctcacccat ttcaaccagc ctagcagcat     120
ctgcaacatc tacaatggcc ttgacctttg ctttactggt ggccctggtg gtgctcagct     180
gcaagtcaag ctgctctctg gctgtgatc tacctcaaac ccacagcctg gtaacagga      240
ggaccttgat actcctggca caaatgagga gaatctctct tttcttctgc ctgaaggaca     300
gacatgactt tgaatttccc caggaggagt ttggcaacca gttccaaaag gctcaaacca     360
tccctgtcct ccatgagatg atccagcaga ccttcaatct cttcagcaca aaggactcat     420
ctgctgcttg ggatgagacc ctcctaaaca aattctacac tgaactctac cagcagctga     480
atgacctgga agcctgtgtg atgcaggaga tgggggtgac agagactccc ctgatgaaca     540
agaactccat cctggccgtg aggaaatact ccaaagaat cactctctat ctgaaagaga     600
agaaatacag tctttgtgcc tgggaggttg tcagagcaga aattatgaga tctttttctt     660
tgtcaacaaa cttgcaagaa agtttaagaa gtaaggaatg aaaactggtt caacatggaa     720
attatttca ttgactatac accagctcac                                       750

<210> SEQ ID NO 66
<211> LENGTH: 188
<212> TYPE: PRT
<213> ORGANISM: Macaca fascicularis

<400> SEQUENCE: 66

Met Ala Leu Thr Phe Ala Leu Leu Val Ala Leu Val Val Leu Ser Cys
  1               5                  10                  15

Lys Ser Ser Cys Ser Leu Gly Cys Asp Leu Pro Gln Thr His Ser Leu
             20                  25                  30

Gly Asn Arg Arg Thr Leu Ile Leu Leu Ala Gln Met Arg Arg Ile Ser
         35                  40                  45

Leu Phe Phe Cys Leu Lys Asp Arg His Asp Phe Glu Phe Pro Gln Glu
     50                  55                  60

Glu Phe Gly Asn Gln Phe Gln Lys Ala Gln Thr Ile Pro Val Leu His
 65                  70                  75                  80

Glu Met Ile Gln Gln Thr Phe Asn Leu Phe Ser Thr Lys Asp Ser Ser
                 85                  90                  95

Ala Ala Trp Asp Glu Thr Leu Leu Asn Lys Phe Tyr Thr Glu Leu Tyr
            100                 105                 110

Gln Gln Leu Asn Asp Leu Glu Ala Cys Val Met Gln Glu Met Gly Val
        115                 120                 125

Thr Glu Thr Pro Leu Met Asn Lys Asn Ser Ile Leu Ala Val Arg Lys
    130                 135                 140

Tyr Phe Gln Arg Ile Thr Leu Tyr Leu Lys Glu Lys Lys Tyr Ser Leu
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 67
```

```
<211> LENGTH: 777
<212> TYPE: DNA
<213> ORGANISM: Macaca fascicularis
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
<220> FEATURE:
<221> NAME/KEY: modified_base
<222> LOCATION: (17)..(17)
<223> OTHER INFORMATION: a, c, g, t, unknown or other
<220> FEATURE:
<221> NAME/KEY: modified_base
<222> LOCATION: (712)..(712)
<223> OTHER INFORMATION: a, c, g, t, unknown or other
<220> FEATURE:
<221> NAME/KEY: modified_base
<222> LOCATION: (721)..(721)
<223> OTHER INFORMATION: a, c, g, t, unknown or other
<220> FEATURE:
<221> NAME/KEY: modified_base
<222> LOCATION: (733)..(733)
<223> OTHER INFORMATION: a, c, g, t, unknown or other
<220> FEATURE:
<221> NAME/KEY: modified_base
<222> LOCATION: (744)..(744)
<223> OTHER INFORMATION: a, c, g, t, unknown or other
<220> FEATURE:
<221> NAME/KEY: modified_base
<222> LOCATION: (768)..(768)
<223> OTHER INFORMATION: a, c, g, t, unknown or other

<400> SEQUENCE: 67
ctgctantac ncctagncaa catttgcaac atcccaatgg ccctgtcctt ttctttactg      60
atggccgtgg tggtgctcag ctacaaatcc atctgctctc tgggctgtga tcctccccgg     120
acccacagcc tgggtcatag gagggccttg atactcctgg cacaaatgga agaatctct     180 cctttctcct gtctgaagga cagacatgac tttggattcc cccaggagga gtttgatggc     240
aaccagttcc agaaggctca agccatctct gtcctccatg agatgatcca gcagaccttc     300
aatctcttca gcacaaagga ctcatctgct gcttgggaac agaacctcct agaaaaattt     360
tccgctgagc tttaccagca actgaatgcc ttggaagcct gtgtgatagc agagcctggg     420
atggaagaga ctctcttgat gaatgaggat tccatcctgg ctgtgaagaa atacttccaa     480
agaatcactc tctatctgac ggagaagaag tacagcccct gtgcctggga ggttgtcaga     540
gcagaaatca tgagatccct ctcttttca acaaacttgc aaagaaaatt aaggaggaag     600
gattgaaaac tggttcaaca tggaaatgat cctcattgac ggacatgtca tctcacactt     660
tcatgagttc ttccattttc aaagactcac ttgaattctg cagatatcca tncacactgg     720
ncggccgctc gancatgcat ctanaagggc ccctattcta tagtgtcncc taaatgc        777

<210> SEQ ID NO 68
<211> LENGTH: 189
<212> TYPE: PRT
<213> ORGANISM: Macaca fascicularis

<400> SEQUENCE: 68

Met Ala Leu Ser Phe Ser Leu Leu Met Ala Val Val Leu Ser Tyr
 1               5                  10                  15

Lys Ser Ile Cys Ser Leu Gly Cys Asp Pro Pro Arg Thr His Ser Leu
                20                  25                  30

Gly His Arg Arg Ala Leu Ile Leu Leu Ala Gln Met Glu Arg Ile Ser
            35                  40                  45
```

```
Pro Phe Ser Cys Leu Lys Asp Arg His Asp Phe Gly Phe Pro Gln Glu
         50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Trp Glu Gln Asn Leu Leu Glu Lys Phe Ser Ala Glu Leu
            100                 105                 110

Tyr Gln Gln Leu Asn Ala Leu Glu Ala Cys Val Ile Ala Glu Pro Gly
        115                 120                 125

Met Glu Glu Thr Leu Leu Met Asn Glu Asp Ser Ile Leu Ala Val Lys
        130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Arg Lys Leu Arg Arg Lys Asp
                180                 185

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 69

His His His His His His
 1               5
```

INTERFERONS OF RHESUS AND CYNOMOLGUS ORIGIN AND USES THEREOF

CROSS-REFERENCE TO RELATED APPLICATIONS

This patent application claims under 35 U.S.C. 119(e) the benefit of the filing dates of U.S. Provisional Application Nos. 60/923,069, filed on Apr. 11, 2007, and 60/925,281, filed on Apr. 18, 2007. The entire contents (including specifications and drawings) of these applications are incorporated herein by reference in their entirety.

BACKGROUND OF THE INVENTION

The present invention relates to interferon sequences and methods of production and use.

Interferons (IFNs) are a family of cytokines secreted by a wide variety of eukaryotic cells upon exposure to various stimuli (Zoon K C: Human Interferons: Structure and Function. p. 1-12. In: Interferon 8. Academic Press, London, 1987; Walter et al., Cancer Biother. Radiopharm. 13, 143-54, 1998; Pestka, S., Biopolymers 55, 254-87, 2000). Interferons have been classified by their chemical and biological characteristics into four groups: IFN-α (leukocytes), IFN-β (fibroblasts), IFN-γ (lymphocytes), and IFN-ω (leukocytes). IFN-α and β are known as Type I interferons: IFN-γ is known as a Type-II or immune interferon. The IFNs exhibit anti-viral, immuno-regulatory, and antiproliferative activity. The clinical potential of interferons has been recognized.

Human leukocyte interferon was first discovered and prepared in the form of very crude fractions by Isaacs and Lindemann. Efforts to purify and characterize the material have led to the preparation of relatively homogeneous leukocyte interferons derived from normal or leukemic (chronic myelogenous leukemia or "CML") donor leukocytes. These interferons are a family of proteins characterized by a potent ability to confer a virus-resistant state in their target cells. In addition, interferon can inhibit cell proliferation, modulate immune responses and alter expression of proteins. These properties have prompted the clinical use of leukocyte interferon as a therapeutic agent for the treatment of viral infections and malignancies.

During the past several decades a large number of human and animal IFNs have been produced, identified, purified and cloned. Several of the IFN preparations have been prepared for clinical trial in crude form, for some of the original interferon preparations, as well as in purified form. Several individual recombinant IFN-α species have been cloned and expressed. The proteins have then been purified by various procedures and formulated for clinical use in a variety of formulations. Most of the IFNs in clinical use that have been approved by various regulatory agencies throughout the world are mixtures or individual species of human α interferon (Hu-IFN-α). In some countries Hu-IFN-β and -γ have also been approved for clinical trial and in some cases approved for therapeutic use. The major thesis underlying clinical use of these IFNs was that they were natural molecules produced by normal individuals. Indeed, the specific thesis was that all the interferons prepared for clinical use, be they natural- or recombinant-generated products, represented IFNs that were produced naturally by normal people. This is true for a large number of IFNs as well as specific growth factors, lymphokines, cytokines, hormones, clotting factors and other proteins that have been produced.

A need remains for the identification of additional IFNs, in human and other organisms, that may be used for the treatment or prevention of diseases such as viral infection and/or cancer. The present invention provides such interferons proteins and genes.

SUMMARY OF THE INVENTION

Provided herein may be polynucleotides encoding interferon polypeptides, and methods of interferon polypeptide production and use. Interferons or polynucleotides encoding interferons may be useful as research reagents; standards for bioactivity assays; biomarkers such as for interferon protein or gene induction or reduction in response to acute or chronic disease states such as viral infections, cancer, autoimmune states, immunocompromised states, other hyper- or hypoimmune conditions, and in pharmaceutical or biopharmaceutical intervention; pharmacodynamic markers such as for interferon protein or gene induction or reduction in response to pharmaceutical or biopharmaceutical intervention; toxicological markers such as for interferon protein or gene induction or reduction in response to acute or chronic exposure of a subject to toxins; medicaments for animal subjects; medicaments in combination with other agents; reagents or markers for study of neutralizing antibodies; a measure of immune competence/general immune function, and the like. Interferons or polynucleotides encoding interferons may be used to predict responses of higher primates to administration of interferons and agents to be used in combination with interferons; to quantify the responses of animal subjects to viral infections, immune response modifying agents, other pharmaceutical manipulation of immune responses, and the like. Interferons find application in antiviral, antitumor, anti-cancer, immune system or immune response stimulation, immune system or immune response inhibition, and the like.

For clarity, Rhesus interferon nucleic acid sequences are listed as SEQ ID NO: 1, 3, 5, 7, 9, 11, 13, 15, 17, 19, 21, 23, 25, 27, 29, 31, 33, 35, 37, or 39. Rhesus interferon polypeptide sequences are listed as SEQ ID NO: 2, 4, 6, 8, 10, 12, 14, 16, 18, 20, 22, 24, 26, 28, 30, 32, 34, 36, 38, or 40.

Cynomolgus interferon nucleic acid sequences are listed as SEQ ID NO: 41, 43, 45, 47, 49, 51, 53, 55, 57, 59, 61, 63, 65, or 67. Cynomolgus interferon polypeptide sequences are listed as SEQ ID NO: 42, 44, 46, 48, 50, 52, 54, 56, 58, 60, 62, 64, 66, or 68.

In an aspect of the invention, an isolated nucleic acid may comprise a polynucleotide encoding at least a portion of an interferon polypeptide, wherein the nucleic acid comprises a sequence identical to at least one of SEQ ID NO: 1, 3, 5, 7, 9, 11, 13, 15, 17, 19, 21, 23, 25, 27, 29, 31, 33, 35, 37, or 39. In another aspect of the invention, an isolated nucleic acid may comprise a polynucleotide encoding at least a portion of an interferon polypeptide, wherein nucleic acid comprises a sequence identical to at least one of SEQ ID NO: 41, 43, 45, 47, 49, 51, 53, 55, 57, 59, 61, 63, 65, or 67.

In an aspect of the invention, an isolated nucleic acid comprises a polynucleotide encoding at least a portion (preferably a functional portion) of an interferon polypeptide, wherein the interferon polypeptide comprises an amino acid sequence identical to at least one of SEQ ID NO: 2, 4, 6, 8, 10, 12, 14, 16, 18, 20, 22, 24, 26, 28, 30, 32, 34, 36, 38, or 40. In an aspect of the invention, an isolated nucleic acid comprises a polynucleotide encoding at least a portion (preferably a functional portion) of an interferon polypeptide, wherein the interferon polypeptide includes an amino acid sequence identical to at least one of SEQ ID NO: 42, 44, 46, 48, 50, 52, 54, 56, 58, 60, 62, 64, 66, or 68.

Preferably, the encoded portion is at least a functional fragment of (or identical to) the interferon polypeptide. The function of the encoded portion may be assayed using any of the methods (e.g., functional assays) described herein, or those known in the art.

In an embodiment, an expression vector capable of replicating in a prokaryotic cell, a eukaryotic cell, or both, may comprise the nucleic acid of any one of the SEQ ID NO's described herein. A host cell may comprise the expression vector. A method of producing a polypeptide may comprise culturing the host cell in a cell culture medium to express said polypeptide and isolating said polypeptide from said cell culture. In an embodiment, an isolated polypeptide may be encoded by the isolated nucleic acid of any one of the SEQ ID NO's described herein. In an embodiment, a plasmid may contain the nucleic acid of any one of the SEQ ID NO's described herein. In an embodiment, the nucleic acid molecule as described herein may additionally contain a sequence encoding the amino acid methionine attached to the N-terminus of the ordinarily first amino acid of said non-human mammalian interferon. In an embodiment, the nucleic acid molecule as described herein may additionally contain a sequence encoding a cleavable conjugate or signal protein attached to the N-terminus of the ordinarily first amino acid of said non-human mammalian interferon.

In an embodiment, the polypeptide of the invention may comprise the amino acid sequence set forth in any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or functional fragments/variants thereof that is at least about 80%, 85%, 90%, 95%, 97%, 98%, 99%, 99.5% identical to one or more of the recited sequences, or functional fragments/variants thereof that have at most 20, 15, 10, 9, 8, 7, 6, 5, 4, 3, 2, or 1 amino acid substitutions compared to one or more of the recited sequences, with or without the signal sequence, with or without substitution of one or more cysteine residues with another residue, such as a serine, and contiguous segments thereof of at least 165 amino acids in length. In an embodiment, the portion or polypeptide may enhance the activity of a Type I interferon or a Type II interferon. In an embodiment, the Type I interferon may be selected from interferon alphas (IFN-$\alpha$s) and interferon betas (IFN-$\beta$s). In an embodiment, the Type II interferon may be interferon gamma (IFN-$\gamma$). In an embodiment, the polypeptide may inhibit proliferation of a mammalian cell, inhibit viral infection of a mammalian cell, increase expression of MHC Class I and/or MHC Class II molecules on the surface of mammalian cells, stimulate or inhibits cytokine production by mammalian cells or the like, or a combination thereof. In an embodiment, the mammalian cell may be a non-human primate cell. In an embodiment, the mammalian cell may be an LLC-MK2 cell (FIG. 1) or an A549 cell (FIG. 2). The viral infection may be caused by one of encephalomyocarditis virus, vesicular stomatitis virus, coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, influenza virus, flavivirus, or the like.

In an embodiment, an isolated antibody may bind specifically to a polypeptide having an amino acid sequence as described herein. In an embodiment, the polypeptides described herein may be combined with a pharmaceutically acceptable excipient.

In an embodiment, the polypeptide of the invention may contain modifications. In an embodiment, the modification may increase the serum half-life of the polypeptide, by at least 1, 2, 3, 4, 5, 10, 20, 50 or 100 fold relative to the non-modified form. In an embodiment, the modification comprises a polyethylene glycol (PEG) group. In an embodiment, the polyethylene glycol is selected from linear PEG chains and branched PEG chains. In an embodiment, the polyethylene glycol group is attached to a group selected from the lysine side chains and the N-terminal amino group of the polypeptide.

Another aspect of the invention provides an expression vector capable of replicating in a prokaryotic cell, in a eukaryotic cell, or in both, comprising any of the above nucleic acids, while another aspect of the invention provides a host cell containing the expression vector. In an embodiment, the host cell may be E. coli, B. subtilis, a yeast cell, an insect cell, a bacterium, a fungal cell, an avian cell, a plant cell, a myeloma cell, fibroblast 3T3 cells, COS cells, Chinese Hamster Ovary (CHO) cells, mink-lung epithelial cell, human foreskin fibroblast cell, human glioblastoma cell, or a teratocarcinoma cell or any other mammalian cell or other cell. A culture of such transformant cells may produce non-human mammalian interferon in a form unaccompanied by a signal peptide or presequence peptide that is the immediate product of the translation of the mRNA of said non-human mammalian interferon.

In an aspect of the invention, a process of producing an expression vector as described herein may comprise constructing a first DNA sequence coding for said polypeptide and operably linking said first DNA sequence with a second DNA sequence which controls expression of said first DNA sequence.

In an aspect of the invention, a process for producing a polypeptide may consist essentially of the amino acid sequence of a non-human mammalian interferon comprising causing a culture of a microorganism or cell culture transformed with an expression vector as described herein to grow and effect production of said polypeptide and recovering said polypeptide.

In an aspect of the invention, a recombinant virus may comprise the expression vector as described herein.

Another aspect of the invention may involve a method of producing a polypeptide, comprising (i) culturing the host cell expressing one of the polypeptides described herein in a cell culture medium to express said polypeptide; (ii) and isolating said polypeptide from said cell culture. In one embodiment of the methods of producing a polypeptide, the host cell may be E. coli, B. subtilis, a yeast cell, an insect cell, a bacterium, a fungal cell, an avian cell, a plant cell, a myeloma cell, a fibroblast 3T3 cell, a COS cell, a Chinese hamster ovary (CHO) cell, a mink-lung epithelial cell, a human foreskin fibroblast cell, a human glioblastoma cell, a teratocarcinoma cell, or other cell.

In an aspect of the invention, a process may comprise expressing a nucleic acid molecule as described herein in a form unaccompanied by the signal peptide or presequence peptide that is the immediate product of the translation of the mRNA of said non-human mammalian interferon in a microorganism or cell culture. The microorganism may be obtained by transforming an E. coli strain.

Another aspect of the invention provides an isolated antibody, or antigen-binding fragment thereof, that may be raised against, or developed through specific immunization with any one or more of the novel polypeptides described herein, and which binds specifically to any one or more of the novel polypeptides described herein. Another aspect of the invention provides an isolated antibody that specifically binds to a polypeptide comprising the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. In an embodiment, the antibody may be a monoclonal antibody. In an embodiment, the antibody may be a humanized antibody, single chain antibody, Fv fragment, scFv, scFv dimer, Nanobody™, Fab fragment, Fab' fragment, F(ab')2 fragment, and the like. In an embodiment, the antibody may be a polyclonal antibody. In an embodiment, the antibody may block binding of the polypeptide to its receptor. In an embodiment, the antibody may be a neutralizing antibody or exhibits neutralizing activity. In an embodiment, the antibody or fragment thereof may be selected by immunoselection or immunodepletion. In an embodiment, the antibody or fragment thereof may be detectably labeled. Any of aid antibodies may be useful as diagnostic tools for measuring interferon in biological fluids wherein the interferon level correlates directly or inversely with disease states, sequalae of pharmacological interventions, or sequalae of toxins.

Another aspect of the invention provides a composition, preferably a pharmaceutical composition, which may comprise at least one of the nucleic acids, polypeptides or antibodies disclosed herein, and a pharmaceutically acceptable excipient. In an embodiment, the composition may comprise one of the IFN polypeptides, described herein, such as interferon polypeptides, fragments, or variants thereof, and a pharmaceutically-acceptable excipient. In an embodiment, the composition may comprise a carrier and at least one of the expression vector described herein or a recombinant virus that comprises the expression vector described herein.

Another aspect of the invention provides a vaccine that may comprise (i) an antigen; (ii) an interferon polypeptide, variant, or fragment thereof as described herein; and optionally (iii) a pharmaceutically-acceptable carrier.

Another aspect of the invention provides a method of treating a subject, mammal, or other organism comprising administering a therapeutically effective amount of one of the compositions described herein. Another aspect of the invention provides a method of treating a mammal or other organism comprising administering a therapeutically effective amount of one of the isolated polypeptides described herein, such as the cytokine polypeptides. In an embodiment, the cytokine polypeptide is an interferon polypeptide or fragment or variant thereof. In an embodiment, the composition that is administered may comprise an interferon polypeptide or biologically-active fragment thereof. In an embodiment, the method further comprises administering to the mammal or other organism an IFN-α polypeptide, an IFN-β polypeptide or an IFN-γ polypeptide. In an embodiment, the method further comprises administering to the mammal or other organism an IFN-α polypeptide, an IFN-β polypeptide or an IFN-γ polypeptide, in an amount that synergizes with the interferon polypeptide administered to the mammal or other organism.

In an embodiment, the therapeutic method is for treating an illness, condition, disease or the like. In an embodiment, the therapeutic method is for the treatment of an immune system related disorder. In an embodiment, the therapeutic method is for treating a disorder selected from an autoimmune disease, multiple sclerosis, lymphoma, cancer, allergy, and the like. In an embodiment, the therapeutic method is for treating a bacterial infection. In an embodiment, the therapeutic method is for treating an infection. In an embodiment, the therapeutic method is for treating a viral infection. In an embodiment, the therapeutic method is for treating a parasitic infection. In an embodiment, the therapeutic method is for treating cancer or a tumor. In an embodiment, the therapeutic method is for treating an autoimmune disease. In an embodiment, the therapeutic method is for treating multiple sclerosis. In an embodiment, the therapeutic method is for treating a lymphoma. In an embodiment, the therapeutic method is for treating an allergy. In an embodiment, the therapeutic method is for treating or prevention of viral hepatitis, papilloma viral infection, herpes, or viral encephalitis. In an embodiment, the therapeutic method is for treating or prevention of a viral infection wherein the viral infection is an encephalomyocarditis viral infection or a vesicular stomatitis viral infection or one caused by one of coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, flavivirus, and the like. With regard to treatment of or prevention of disease spread in non-human primates, highly relevant viral targets include those viruses known to infect breeding colonies including Simian Immunodeficiency Virus, Simian T-cell Lymphotrophic Viruses, Herpes B virus, and Simian type D retrovirus. With specific regard to viral outbreaks in breeding colonies, the therapeutic method may find particular utility in zoos, veterinary settings including offices, hospitals, and clinics, and research colonies maintained by pharmaceutical or contract research organizations. In an embodiment, the therapeutic method may be for treating a cancer including, but is not limited to, hairy cell leukemia, chronic myeloid leukemia, lymphoma, acute myeloid leukemia, osteosarcoma, basal cell carcinoma, glioma, renal cell carcinoma, multiple myeloma, melanoma, prostate cancer, breast cancer, lung cancer, colon cancer, pancreatic cancer, Hodgkin's disease, and the like. In an embodiment, the therapeutic method is for treating a non-human mammal. In an embodiment, the therapeutic method is for treating a human. In an embodiment, the therapeutic method is for treating any organism.

In an aspect of the invention, there may be a method for identifying compounds that enhance or inhibit the biological activity of an interferon polypeptide. In an embodiment, there may be a method for identifying compounds that enhance or inhibit the biological activity of an interferon polypeptide as described herein, wherein a compound which enhances the biological activity of an interferon polypeptide is an interferon agonist. In an embodiment, a compound which inhibits the biological activity of an interferon polypeptide may be an interferon antagonist.

Another aspect of the invention provides a method for identifying a compound that modulates the activity of an interferon polypeptide, the method comprising (i) contacting a cell with the interferon polypeptide and with the compound; and (ii) measuring a response of the cell to the interferon polypeptide; wherein a compound that modulates the response of the cell to the interferon polypeptide is a modulator of the interferon polypeptide. In an embodiment, the response of the cell is cell division or susceptibility to viral infection. In an embodiment, the interferon polypeptide (i) shares at least 99% amino acid sequence identity to any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to a portion thereof; or (ii) comprises at least 100, 120, 140, 160, or 170 contiguous amino acids of any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68; or (iii) both.

Another aspect of the invention provides a method of detecting the level of an interferon polypeptide in a mammal, the method comprising (i) obtaining a sample from the mammal; (ii) contacting the sample with an antibody or binding partner specific for the interferon polypeptide; and (iii) quantifying the amount of antibody or binding partner bound to the interferon polypeptide. Another aspect of the invention provides a method of detecting the level of an interferon nucleic acid in a mammal, the method comprising (i) obtaining a sample from the mammal; (ii) contacting the sample with a polynucleotide complementary to the interferon nucleic acid; and (iii) quantifying the amount of polynucleotide bound to the interferon nucleic acid. In an embodiment, the sample may be selected from whole blood, serum, plasma, other bodily fluid, tissue, muscle, bone and the like.

In an aspect of the invention, a binding partner may specifically bind to a polypeptide comprising the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68. In an aspect of the invention, a binding partner may bind to one or more of the polypeptides comprising the amino acid sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68. In an embodiment, the scaffold of the binding partner is comprised of a portion of one of a fibronectin molecule, a transferrin molecule, an anticalin or lipocalin molecule, a phylomer, a CycloTriVeratrylene molecule, a TriAzaCyclophane molecule, a Shark New Antigen Receptor, a peptide aptamer, or the like.

In an aspect of the invention, a process of producing an expression vector as described herein may comprise constructing a first DNA sequence coding for said polypeptide and operably linking said first DNA sequence with a second DNA sequence which controls expression of said first DNA sequence.

In an aspect of the invention, a process for producing a polypeptide may consist essentially of the amino acid sequence of a non-human mammalian interferon comprising causing a culture of a microorganism or cell culture transformed with an expression vector as described herein to grow and effect production of said polypeptide and recovering said polypeptide.

In an aspect of the invention, a preparation of an isolated peptide as described herein may demonstrate activity of at least $1\times10^7$ U/mg in cytopathic effect assays in either LLC-MK2 cells using vesicular stomatitis virus or A549 cells using encephalomyocarditis virus.

In an aspect of the invention, a kit may be provided for detecting one or more of the polypeptides described herein. As discussed herein, a kit may be a combination of any two or more items. In an embodiment, a kit may include a protein and one or more reagents. In an embodiment, a kit may contain a protocol, specification or data sheets.

In an aspect of the invention, a kit may be provided for differentiating between one or more of the polypeptides as described herein.

In an aspect of the invention, a kit may be provided for differentiating one or more of the polypeptides as described herein from similar polypeptides.

In an aspect of the invention, a kit may be provided for specifically detecting one or more of the nucleic acids as described herein. In an aspect of the invention, a kit may be provided for specifically differentiating between one or more of the nucleic acids as described herein. In an aspect of the invention, a kit may be provided for specifically differentiating one or more of the nucleic acids as described herein from similar nucleic acid sequences. In an embodiment of any of these aspects, a kit may utilize polymerase chain reaction, single nucleotide polymorphisms, single hairpin loops, or locked nucleic acids.

In an aspect of the invention, the polypeptides may serve as activity standards in assays of interferon bioactivity.

In an aspect of the invention, the polypeptides may serve as activity standards in assays of anti-interferon neutralizing antibody bioactivity.

In an aspect of the invention, the polypeptide as described herein may exhibit specific activity of at least $1\times10^7$ U/mg in a cytopathic effect assay using LLC-MK2 cells and Vesicular Stomatitis Virus. In an embodiment, the polypeptide may be expressed in microbial cells and exhibits the cytopathic inhibition activity of this aspect of the invention. In an embodiment, the polypeptide may be expressed in eukaryotic cells and exhibits the cytopathic inhibition activity of this aspect of the invention. In an embodiment, the polypeptide may be expressed in mammalian cells and exhibits the cytopathic inhibition activity of this aspect of the invention. In an embodiment, the polypeptide may be expressed in insect cells and exhibits the cytopathic inhibition activity of this aspect of the invention. In an embodiment, the polypeptide may be expressed in yeast cells or other cells and exhibits the cytopathic inhibition activity of this aspect of the invention.

In an aspect of the invention, a method may detect and/or measure the concentration of the polypeptide as described herein in a variety of matrices including culture supernatant, serum, plasma, extracellular fluid, whole blood, sputum, and nasal secretions, other bodily fluids, tissue, muscle, bone and the like. In an embodiment, the detection and/or measurement method may comprise immunoassays such as ELISAs, ECL and others which detect these molecules at less than 25 pg/mL. In an embodiment, the detection and/or measurement method may comprise immunoassays such as ELISAs, ECL and others which detect these molecules at less than 10 pg/mL. In an embodiment, the detection and/or measurement method may comprise immunoassays such as ELISAs, ECL and others which detect these molecules at less than 5 pg/mL. In an embodiment, the detection and/or measurement method may comprise immunoassays such as ELISAs, ECL and others which detect these molecules at less than 1 pg/mL. In an embodiment, the detection and/or measurement method may comprise antiviral assays including cytopathic effect inhibition assays and viral yield reduction assays. In an embodiment, the assay may be a cytopathic effect assay. In an embodiment, the assay may be a viral yield reduction assay. In an embodiment, the assay may be a plaque assay. In an embodiment, the assay may be a reporter gene assay. In an embodiment, the assay may be a PCR-based assay. In an embodiment, the assay is an immunoassay. In an embodiment, the polypeptides as described herein may function as biomarkers correlating with one or more of: (i) particular acute or chronic disease states, comprising: Viral infections, Cancer, Autoimmune states, Immunocompromised states, Other hyper- or hypoimmune conditions; (ii) Responses to administration of pharmacological agents, toxins, or therapeutic interventions; (iii) General immune function; and (iv) General toxicology. In an embodiment, the polypeptides as described herein may function as immunotoxicological markers correlating with one or more of: (i) particular acute or chronic disease states, comprising: Viral infections, Cancer, Autoimmune states, Immunocompromised states, Other hyper- or hypoimmune conditions; (ii) Responses to administration of pharmacological agents, toxins, or therapeutic interventions; (iii) General immune function; and (iv) General toxicology. In an embodiment, the polypeptides as described herein may function as pharmacodynamic or toxicological markers correlating with one or more of: (i) Responses to administration of pharmacological agents, toxins, or therapeutic interventions; (iii) General immune function; and (iv) General toxicology. In an embodiment, the subject may be a human, a non-human primate, a non-primate mammal, a non-mammal animal, or other organism. The method may be used to predict the effect of human interferons administered to humans. The method may be used to determine the efficacy of interferon in animal models of human disease. The method may be used to determine the side effect profile of interferons. The method may be used to predict responses of higher primates to administration of interferons and agents to be used in combination with interferons.

In an aspect of the invention, a method of identifying an intervention that increases or decreases the expression of any of the polypeptides described herein may comprise: obtaining a biological sample; exposing said biological sample to an intervention; waiting a specified period of time; assessing changes in gene expression levels, levels of RNA, protein, or protein activity levels related to one or more biomarkers of immune function of subject toxicity; and identifying said intervention as one that results in altered expression of any of the polypeptides as described herein. In an embodiment, the biological sample comprises cells. The cells may be obtained from a mammal. The mammal may be a non-human primate. In an embodiment, said change in gene expression levels, levels of RNA, protein, or protein activity levels may correspond to a change in gene expression for a gene encoding any one of a STAT, ISG, ISRE, and IRF protein. In an embodiment, intervention may be a Toll-Like Receptor agonist or antagonist.

The invention further provides agents for the manufacture of medicaments to treat any of the disorders described herein. For example, any methods disclosed herein for treating, preventing or aiding in the prevention of a disorder, such as of viral infections or cancers, by administering an interferon polypeptide to an individual may be applied to the use of the agent in the manufacture of a medicament to treat that disorder.

The present invention provides isolated nucleic acid molecules comprising a polynucleotide encoding at least a portion of a non-human primate interferon polypeptide including an amino acid sequence shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. Thus, one aspect of the invention provides an isolated polynucleotide comprising a nucleotide sequence selected from the group consisting of: (a) a nucleotide sequence encoding an interferon polypeptide including an amino acid sequence in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68; (b) a nucleotide sequence encoding a biologically active fragment of a polypeptide shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68; and (c) a nucleotide sequence complementary to at least one of any of the nucleotide sequences in (a) or (b) above.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30-70 (e.g., 50) nucleotides of the reference polynucleotide. These may be useful as diagnostic and therapeutic probes and primers as discussed above and in more detail below. In addition, nucleic acids designed to hybridize with high specificity may be used to block the expression of a single interferon gene or multiple interferon genes. This may include antisense oligonucleotides of at least 8 nucleotides in length. They may be comprised on authentic nucleotides and a phosphate backbone, or can contain artificial moieties included to aid in hybridization efficiency, limit degradation, or limit off target gene silencing. Similarly, siRNAs designed to target a single interferon gene or multiple interferon mRNAs using similar approaches are possible. Likewise, microRNAs designed to target regions of the mature mRNAs for any of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67 may affect gene and/or protein expression.

In another aspect, any of the nucleic acid molecules of the present invention which encode interferon polypeptides may include, but are not limited to, those encoding the amino acid sequence of the complete polypeptide, by itself; and the coding sequence for the complete polypeptide and additional sequences, such as those encoding an added secretory leader sequence, such as a pre-, or pro- or prepro-protein sequence.

Also encoded by nucleic acids of the invention may be the above protein sequences together with additional, non-coding sequences, including, for example, but not limited to introns and non-coding 5' and 3' sequences, such as the transcribed, non-translated sequences that play a role in transcription, mRNA processing, including splicing and polyadenylation signals, for example-ribosome binding and stability of mRNA; and an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence may be a hexa-histidine peptide, such as the tag provided in a pQE vector (QIAGEN, Inc.), among others, many of which are commercially available. For instance, hexa-histidine as described by Gentz et al. provides for convenient purification of the fusion protein (Gentz et al. *Proc. Natl. Acad. Sci. USA* 86, 821-824, 1989). The "HA" tag is another peptide useful for purification which corresponds to an epitope derived from the influenza hemagglutinin protein (Wilson et al. *Cell* 37, 767, 1984). As discussed below, other such fusion proteins include a cytokine fused to Fc at the N- or C-terminus.

The present invention also relates to recombinant vectors, which include the isolated nucleic acid molecules of the present invention, and to host cells containing the recombinant vectors, as well as to methods of making such vectors and host cells and for using them for production of interferon polypeptides or peptides by recombinant techniques.

An additional embodiment of this aspect of the invention relates to a peptide or polypeptide which comprises the amino acid sequence of an epitope-bearing portion of an interferon polypeptide having an amino acid sequence described in (a) or (b), above. Peptides or polypeptides having the amino acid sequence of an epitope-bearing portion of an interferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody or binding partner that may bind specifically to an interferon polypeptide having an amino acid sequence described in (a) or (b) above. The invention further provides methods for isolating antibodies that may bind specifically to an interferon polypeptide having an amino acid sequence as described herein. Such antibodies may be useful in kits to quantify the interferons, reagents for detection of the interferons on Western blots, for localization of the interferons or through immunocytochemistry, or therapeutically.

In another aspect, the invention further provides compositions comprising any of the interferon polynucleotides or interferon polypeptides, described herein, for administration to cells in vitro to cells ex vivo and to cells in vivo, or to a multicellular organism. In certain particularly preferred embodiments of this aspect of the invention, the compositions may comprise an interferon polynucleotide for expression of an interferon polypeptide in a host organism for treatment of disease. Particularly preferred in this regard is expression in an animal subject for treatment of a dysfunction associated with loss of endogenous activity of an interferon.

The invention also provides for pharmaceutical compositions comprising interferon polypeptides which may be employed, for instance, to treat immune system-related disorders such as viral infection, parasitic infection, bacterial infection, cancer, autoimmune disease, multiple sclerosis, lymphoma, allergy, and the like. In certain preferred embodiments, the subject pharmaceutical composition may be a veterinary composition for administration to a non-human animal, preferably a non-human primate. In certain embodiments, the subject pharmaceutical composition may be for human use. Exemplary conditions which can be treated with an interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T-cell lymphoma), and viral infections. Without limitation, treatment with interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6), papilloma, poxvirus, picornavirus, adenovirus, rhinovirus, human T lymphotrophic virus-type 1 and 2 (HTLV-1-2), human rotavirus, rabies, retroviruses including human immunodeficiency virus (HIV), encephalitis and respiratory viral infections. The method of the invention can also be used to modify various immune responses.

In an embodiment, the subject interferons may be used as anti-viral agents. Interferons have been used clinically for anti-viral therapy, for example, in the treatment of acquired immune disorders, encephalomyocarditis virus, vesicular stomatitis virus, coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, influenza virus, flavivirus, and the like.

In another embodiment, the subject interferon may be used as anti-parasitic agents. The subject interferons may be used, for example, for treating *Cryptosporidium parvum* infection.

In still another embodiment, the subject interferons may be used as anti-bacterial agents. Interferons have been used clinically for anti-bacterial therapy. For example, the subject interferons can be used in the treatment of multidrug-resistant pulmonary tuberculosis.

In yet another embodiment, the subject interferons may be used as anti-cancer agents. Interferon therapy using the subject interferons can be used in the treatment of numerous cancers e.g., hairy cell leukemia, acute myeloid leukemia, osteosarcoma, basal cell carcinoma, glioma, renal cell carcinoma, multiple myeloma, melanoma, Hodgkin's disease, and the like.

In yet another embodiment, the subject interferons may be used as part of an immunotherapy protocol. The interferons of the present invention may be used clinically for immunotherapy or more particularly, for example, to prevent graft vs. host rejection, or to curtail the progression of autoimmune diseases, such as arthritis, multiple sclerosis, or diabetes. In another embodiment, the subject interferons may be used as part of a program for treating allergies.

In still another embodiment, the subject interferons may be used as vaccine adjuvants. The subject interferons may be used as an adjuvant or coadjuvant to enhance or stimulate the immune response in cases of prophylactic or therapeutic vaccination.

In addition to the treatment of animals in general, the specific invention particularly contemplates the use of the subject interferons for the treatment of primates as part of veterinary protocols. In an embodiment, the interferon is a Rhesus (*Macaca mulatta*) interferon. In another embodiment, the interferon is a Cynomolgus (*Macaca fascicularis*) interferon.

The subject invention also contemplates functional antagonists, e.g., wherein one or more amino acid residues are different from the wild-type interferon, which inhibit one or more biological activities of the wild-type interferon. Such antagonists can be used to treat disorders resulting from aberrant over expression or other activation of an endogenous interferon. The functional antagonists may be formulated in a pharmaceutical preparation.

The present invention also provides a screening method for identifying compounds capable of enhancing or inhibiting a biological activity of an interferon polypeptide, which involves contacting a receptor which is enhanced by an interferon polypeptide with the candidate compound in the presence of an interferon polypeptide, assaying, for example, anti-viral activity in the presence of the candidate compound and an interferon polypeptide, and comparing the activity to a standard level of activity, the standard being assayed when contact is made between the receptor and interferon in the absence of the candidate compound. In this assay, an increase in activity over the standard indicates that the candidate compound is an agonist of interferon activity and a decrease in activity compared to the standard indicates that the compound is an antagonist of interferon activity.

The measurement of Rhesus and/or Cynomolgus macaque interferon in serum, tissue culture fluid or other matrices is of great interest because these non-human primates have become well accepted models for the pharmaceutical industry. There are a large number of Immune Response Modifiers under development and non-human primate models to test their pharmacodynamics, pharmacokinetics and toxicity are likely to be used. One hallmark of these compounds is their ability to induce interferon-alpha expression in cells and animals and means to accurately measure the induced interferon are needed. Additionally, studies of the mechanism of interferon therapeutics in non-human primates are hampered by the immunogenicity of human proteins in these non-human primates. Therefore, the use of non-human primate congeners of the particular human interferon may predict the outcome(s) of longer term studies on the mechanism of action of the human interferon in human subjects.

Because non-human primates are also used as models of certain viral infections in man such as Rift Valley Fever, Hepatitis C, Ebola virus, and others the ability of human interferon to treat these diseases is limited due to the immunogenicity issues. The use of the polypeptides of the current invention being "self" in the non-human primate rather than "foreign" will greatly aid in such studies.

Measurement of Rhesus and Cynomolgus interferon alphas has been difficult prior to the present invention. The presence of these molecules can be detected by antiviral assays although the presence of other molecules such an interferon-beta can lead to erroneous results. Furthermore, although it has been reported that ELISA assays developed to detect Human Interferon alpha can be used to detect Rhesus and Cynomolgus interferon-alpha, the accuracy of these assays is suspect since the standard used in these assays is human interferon and the degree of detection of the monkey interferon is not determinable. Rhesus IFN-α2 and Cynomolgus IFN-α2 each yield specific ELISA signals of only ~10% when compared to human IFN-α2 using a commercially available ELISA assay (see FIG. 3, PBL Biomedical Laboratories Product #41100-1). Also, it will be evident to one skilled in the art that the proteins of the current invention will allow selection of pre-existing antibodies or the development of novel antibodies which will allow more accurate and sensitive measurement of these molecules.

It is known in the art that Rhesus and Cynomolgus monkeys and isolated cells from these animals produce interferon alphas under a variety of conditions. This interferon alpha can be measured by a variety of methods, including but not limited to immunoassays and cytopathic effect reduction assays. However, since these molecules have not been purified to homogeneity and the immunoassays are known to be inaccurate the determination of the intrinsic activity of these molecules has been previously unattainable. By using the sequences of the current invention, we have determined using purified protein quantified by physical methods, including but not limited to ultraviolet spectroscopy, HPLC, etc., that these molecules have activity in protecting cells in culture from viral infection. Moreover, these proteins protect Rhesus cells such as LLC-MK2 (ATCC CCL-7) from viral infection by vesicular stomatitis virus with a specific activity of greater than $10^7$ units/mg determined using a human interferon standard. Selected interferon proteins may exhibit higher specific activities, up to $10^8$ U/mg.

An additional aspect of the invention is related to a method for treating an animal in need of an increased level of interferon activity in the body comprising administering to such an animal a composition comprising a therapeutically effective amount of an isolated interferon polypeptide of the invention or an agonist thereof.

A still further aspect of the invention is related to a method for treating an animal in need of a decreased level of interferon activity in the body comprising, administering to such an animal a composition comprising a therapeutically effective amount of an interferon antagonist. Preferred antagonists for use in the present invention are interferon-specific antibodies.

Administration of dosages may be periodic, at set intervals, as needed and the like. In embodiments, administration of the described dosages may be every other day, but is preferably once or twice a week. In embodiments, doses may be administered over at least a 24 week period by injection.

Administration of the dose may be intravenous, subcutaneous, intramuscular, parenteral, or by any other acceptable systemic method. Based on the judgment of the attending clinician, the amount of drug administered and the treatment regimen used will, of course, be dependent on the age, sex and medical history of the subject being treated, the neutrophil count (e.g., the severity of the neutropenia), the severity of the specific disease condition, and the tolerance of the subject to the treatment as evidenced by local toxicity and by systemic side-effects. Dosage amount and frequency may be determined during initial screenings of neutrophil count.

Conventional pharmaceutical formulations may be also prepared using the subject interferon compositions of the present invention. The formulations comprise a therapeutically effective amount of an interferon polypeptide together with pharmaceutically acceptable carriers. For example, adjuvants, diluents, preservatives and/or solubilizers, if needed, may be used in the practice of the invention. Pharmaceutical compositions of interferon including those of the present invention may include diluents of various buffers (e.g., Tris-HCl, acetate, phosphate) having a range of pH and ionic strength, carriers (e.g., serum albumin), solubilizers (e.g., Polyoxyethylene Sorbitan or TWEENA polysorbate), and preservatives (e.g., thimerosal, benzyl alcohol). See, for example, U.S. Pat. No. 4,496,537.

The amount of the interferon composition administered to treat the conditions described above may be based on the interferon activity of the composition. It is an amount that may be sufficient to significantly effect a positive clinical response. Although the clinical dose will cause some level of side effects in some subjects, the maximal dose for mammals including humans is the highest dose that does not cause unmanageable clinically-important side effects. For purposes of the present invention, such clinically important side effects are those which would require cessation of therapy due to severe flu-like symptoms, central nervous system depression, severe gastrointestinal disorders, alopecia, severe pruritus or rash Substantial white and/or red blood cell and/or liver enzyme abnormalities or anemia-like conditions or the like are also dose limiting.

Naturally, the dosages of interferon may vary somewhat depending upon the formulation selected. In general, however, the interferon composition is administered in amounts ranging from about 100,000 to about several million IU/m² per day, based on the mammal's condition. The range set forth above is illustrative and those skilled in the art will determine the optimal dosing of interferon selected based on clinical experience and the treatment indication.

The pharmaceutical compositions may be in the form of a solution, suspension, tablet, capsule, lyophilized powder or the like, prepared according to methods well known in the art. It is also contemplated that administration of such compositions will be chiefly by the parenteral route although oral or inhalation routes may also be used depending upon the needs of the artisan.

The inventions described herein may also be represented by the paragraphs below.

1. An isolated nucleic acid comprising a polynucleotide encoding at least a portion of an interferon polypeptide, wherein the nucleic acid comprises a sequence identical to at least one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, or 67.

2. An isolated nucleic acid comprising a polynucleotide encoding at least a portion of an interferon polypeptide, wherein the interferon polypeptide comprises an amino acid sequence identical to at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.

3. An isolated nucleic acid of paragraph 1 or 2, further comprising a sequence encoding the amino acid methionine at the N-terminus of the ordinarily first amino acid of said interferon polypeptide.

4. The isolated nucleic acid of paragraph 1 or 2, further comprising a sequence encoding a cleavable conjugate or signal protein attached to the N-terminus of the ordinarily first amino acid of said interferon polypeptide.

5. An expression vector capable of replicating in a prokaryotic cell, a eukaryotic cell, or both, comprising the nucleic acid of paragraph 1 or 2.

6. The vector of paragraph 5, wherein the vector is a plasmid.

7. A host cell including the expression vector of paragraph 5.

8. The host cell of paragraph 7, wherein the host cell is *E. coli*, *B. subtilis*, a yeast cell, an insect cell, or a mammalian cell.

9. The host cell of paragraph 7, wherein the host cell is selected from the group consisting of bacterium, yeast cell, fungal cell, insect cell, avian cell, mammalian cell, and plant cell.

10. The host cell of paragraph 7, wherein the host cell is a microorganism obtained by transforming an *E. coli* strain.

11. A method of producing a polypeptide, comprising culturing the cell of paragraph 7 in a cell culture medium to express said polypeptide, and isolating said polypeptide from said cell culture.

12. An isolated interferon polypeptide, wherein the polypeptide is encoded by the isolated nucleic acid of paragraph 1 or 2.

13. The isolated polypeptide of paragraph 12, wherein the amino acid sequence is identical to at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.

14. The isolated polypeptide of paragraph 13, wherein the isolated polypeptide comprises the amino acid sequence of the polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, and wherein the polypeptide lacks its associated signal peptide.

15. An isolated polypeptide comprising an amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68, or a contiguous segment of at least 165 amino acids of one of said sequences, wherein the fragment is at least 165 amino acids in length.

16. The polypeptide of any one of paragraphs 13-15, wherein the polypeptide:
    (a) inhibits proliferation of a mammalian cell;
    (b) inhibits viral infection of a mammalian cell;
    (c) increases expression of MHC Class I and/or MHC Class II molecules on the surface of a mammalian cell;
    (d) increases expression of an IFN signal-responsive reporter construct;
    (e) stimulates or inhibits cytokine production by a mammalian cell; or,
    (f) any combination thereof.

17. The polypeptide of paragraph 16, wherein the mammalian cell is a non-human primate cell.

18. The polypeptide of paragraph 16, wherein the mammalian cell is a LLC-MK2 cell, a JTC-12 cell, or an A549 cell.

19. The polypeptide of paragraph 16, wherein the viral infection is caused by a virus selected from encephalomyocarditis virus, vesicular stomatitis virus, coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, influenza virus, or flavivirus.

20. The polypeptide of any one of paragraphs 13-15, wherein the polypeptide comprises a modification that increases its serum half-life.

21. The polypeptide of paragraph 20, wherein the modification comprises the addition of a polyethylene glycol (PEG) group.

22. The polypeptide of paragraph 21, wherein the polyethylene glycol group comprises linear PEG chains or branched PEG chains.

23. The polypeptide of paragraph 22, wherein the polyethylene glycol group is attached to a group selected from: the lysine side chains, or the N-terminal amino group of the polypeptide.

24. An isolated antibody that binds specifically to a polypeptide of any one of paragraphs 13-15.

25. The polypeptide of any one of paragraphs 13-15, in combination with a pharmaceutically acceptable excipient.

26. The polypeptide of any one of paragraphs 13-15, wherein the polypeptide exhibits specific activity of at least $1 \times 10^7$ U/mg in a cytopathic effect assay using LLC-MK2 cells and Vesicular Stomatitis Virus.

27. The polypeptide of any one of paragraphs 13-15, wherein the polypeptide is expressed in microbial cells and exhibits specific activity of at least $1 \times 10^7$ U/mg in a cytopathic effect assay using LLC-MK2 cells and Vesicular Stomatitis Virus.

28. The polypeptide of any one of paragraphs 13-15, wherein the polypeptide is expressed in eukaryotic cells and exhibits specific activity of at least $1 \times 10^7$ U/mg in a cytopathic effect assay using LLC-MK2 cells and Vesicular Stomatitis Virus.

29. The polypeptide of any one of paragraphs 13-15, wherein the polypeptide is expressed in mammalian cells and exhibits specific activity of at least $1 \times 10^7$ U/mg in a cytopathic effect assay using LLC-MK2 cells and Vesicular Stomatitis Virus.

30. The polypeptide of any one of paragraphs 13-15, wherein the polypeptide is expressed in insect cells and exhibits specific activity of at least $1 \times 10^7$ U/mg in a cytopathic effect assay using LLC-MK2 cells and Vesicular Stomatitis Virus.

31. The polypeptide of any one of paragraphs 13-15, wherein the polypeptide is expressed in yeast cells and exhibits specific activity of at least $1 \times 10^7$ U/mg in a cytopathic effect assay using LLC-MK2 cells and Vesicular Stomatitis Virus.

32. A method of treating a subject, comprising administering a therapeutically effective amount of an isolated interferon polypeptide of any one of paragraphs 13-15.

33. The method of paragraph 32, wherein the method treats an immune system related disorder.

34. The method of paragraph 32, wherein the immune system related disorder is selected from: viral infection, parasitic infection, bacterial infection, cancer, autoimmune disease, multiple sclerosis, lymphoma, or allergy.

35. The method of paragraph 32, wherein the method treats or prevents a viral infection selected from: an encephalomyocarditis viral infection, a vesicular stomatitis viral infection, viral hepatitis, a papilloma viral infection, herpes, or viral encephalitis, or a viral infection caused by a virus selected from: coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, influenza virus, or flavivirus.

36. The method of paragraph 32, wherein the subject is a non-human animal, a non-human mammal, or a non-human primate.

37. A method for identifying compounds that enhance or inhibit the biological activity of an interferon polypeptide, comprising:
   (a) treating a cell with the interferon in combination with a test compound;
   (b) waiting a specified amount of time;
   (c) assessing the effect of the test compound on the interferon activity in a bioactivity assay, wherein the interferon bioactivity assay may comprise measurement of any one or more of:
      i. inhibition of proliferation of a mammalian cell;
      ii. inhibition of viral infection of a mammalian cell;
      iii. increase or decrease in expression of MHC Class I and/or MHC Class II molecules on the surface of a mammalian cell;
      iv. increase in expression of an IFN signal-responsive reporter construct;
      v. stimulation or inhibition of cytokine production by mammalian cells; and
      vi. any combination of any one of i-v; and,
   (d) quantifying said responses, wherein the interferon in the bioactivity assay comprise a polypeptide of any one of paragraphs 13-15.

38. The method of paragraph 37, wherein the method is used for identifying compounds that enhance or inhibit the biological activity of an interferon polypeptide of any of paragraphs 13-15, wherein a compound that enhances the biological activity of an interferon polypeptide is an interferon agonist.

39. The method of paragraph 37, wherein a compound that inhibits the biological activity of an interferon polypeptide is an interferon antagonist.

40. A method of producing a polypeptide, comprising:
   (a) culturing a host cell of paragraph 7 in a cell culture medium to express said polypeptide; and,
   (b) isolating said polypeptide from said cell culture.

41. The method of paragraph 40, wherein the host cell is selected from *E. coli, B. subtilis*, a yeast cell, an insect cell, a myeloma cell, a fibroblast 3T3 cell, a HEK-293 cell, a PER.C6 cell, a COS cell, a Chinese hamster ovary (CHO) cell, a mink-lung epithelial cell, a human foreskin fibroblast cell, a human glioblastoma cell, or a teratocarcinoma cell.

42. A process comprising expressing a nucleic acid of paragraph 1 or 2, said nucleic acid encodes a polypeptide (1) that lacks a signal peptide or presequence peptide, and (2) that is the immediate product of the translation of the mRNA of said mammalian interferon in a microorganism or cell culture.

43. A culture of cells transformed according to paragraph 42, which produces non-human mammalian interferon in a form unaccompanied by a signal peptide or presequence peptide that is the immediate product of the translation of the mRNA of said non-human mammalian interferon.

44. A process of producing an expression vector according to paragraph 5, comprising constructing a first DNA sequence coding for said polypeptide, and operably linking said first DNA sequence with a second DNA sequence which controls expression of said first DNA sequence.

45. A process for producing a polypeptide consisting essentially of the amino acid sequence of a non-human mammalian interferon, comprising:
   (a) causing a culture of a microorganism or cell culture transformed with an expression vector according to paragraph 5 to grow;
   (b) effecting production of said polypeptide in said cells; and,
   (c) recovering said polypeptide.

46. A recombinant virus, comprising the expression vector of paragraph 5.

47. A composition comprising a carrier and at least one of the expression vector of paragraph 5, or a recombinant virus that comprises the expression vector of paragraph 5.

48. An isolated antibody or antigen-binding fragment thereof that is produced by immunizing a subject with any one of the polypeptides of paragraphs 13-15, wherein said antibody or antigen-binding fragment thereof specifically binds to any one of said polypeptides.

49. An isolated antibody or antigen-binding fragment thereof that is produced by immunizing a subject with any one of the polypeptides of paragraphs 13-15, wherein said antibody or antigen-binding fragment thereof specifically binds to a polypeptide comprising the amino acid sequence set forth in any one or more of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.

50. An isolated antibody or antigen-binding fragment thereof that is produced by immunizing a subject with a polypeptide comprising the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68, wherein said antibody or antigen-binding fragment thereof binds to one or more of said polypeptides.

51. An isolated antibody or antigen-binding fragment thereof that is produced by genetically immunizing a subject with the nucleic acid sequence of paragraph 1 or 2, wherein said antibody or antigen-binding fragment thereof specifically binds to any one of the polypeptides of paragraphs 13-15.

52. An isolated antibody or antigen-binding fragment thereof that is produced by genetically immunizing a subject with the nucleic acid sequence of paragraph 1 or 2, said antibody or antigen-binding fragment thereof specifically binds to a polypeptide comprising the amino acid sequence set forth in any one or more of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.

53. An isolated antibody or antigen-binding fragment thereof that is produced by genetically immunizing a subject with the nucleic acid sequence of paragraph 1 or 2, said antibody or antigen-binding fragment thereof binds to one or more of said polypeptides of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.

54. The antibody of any one of paragraphs 48-53, wherein the antibody is a monoclonal antibody or an antigen-binding fragment thereof.

55. The antibody of any one of paragraphs 48-53, wherein the antibody is a polyclonal antibody or an antigen-binding fragment thereof.

56. The antibody of any one of paragraphs 48-55, wherein the antibody or antibody fragment inhibits binding of the polypeptide to its receptor.
57. The antibody of any one of paragraphs 48-55, wherein said antibody or antibody fragment is a neutralizing antibody or exhibits neutralizing activity.
58. The antibody of any one of paragraphs 48-55, wherein said antibody or antigen-binding fragment thereof is selected from: humanized antibody, single chain antibody, Fv fragment, scFv, scFv dimer, Nanobody, Fab fragment, Fab' fragment, or F(ab')$_2$ fragment.
59. A binding partner that specifically binds to a polypeptide comprising the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.
60. A binding partner that binds to one or more of the polypeptides comprising the amino acid sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68.
61. The binding partner of paragraph 59 or 60, wherein the binding partner comprises a portion of a scaffold, wherein the scaffold is selected from a fibronectin molecule, a transferrin molecule, an anticalin or lipocalin molecule, a phylomer, a CycloTriVeratrylene molecule, a TriAzaCyclophane molecule, a Shark New Antigen Receptor, or a peptide aptamer.
62. A composition comprising at least one of the nucleic acids, polypeptides, antibodies, or binding partners of any one of paragraphs 1-2, 13-15, 20-23, or 48-61, and a pharmaceutically acceptable excipient.
63. A composition comprising the polypeptide of any one of paragraphs 13-15.
64. A composition comprising the polypeptide of any one of paragraphs 13-15, and a pharmaceutically acceptable excipient.
65. A vaccine comprising (i) an antigen; and (ii) the polypeptide of any one of paragraphs 13-15.
66. A method of detecting the level of an interferon polypeptide of paragraphs 13-15 in a mammal, the method comprising:
   (a) obtaining a sample from the mammal;
   (b) contacting the sample with an antibody (e.g., one raised against and/or specific for a polypeptide of any one of paragraphs 13-15), or a binding partner specific for the interferon polypeptide; and
   (c) quantifying the amount of antibody or binding partner bound to the interferon polypeptide.
67. A method of detecting the level of a nucleic acid of paragraph 1 or 2 in a mammal, the method comprising:
   (a) obtaining a sample from the mammal;
   (b) contacting the sample with a polynucleotide complementary to the interferon nucleic acid; and,
   (c) quantifying the amount of polynucleotide bound to the interferon nucleic acid.
68. The method of paragraph 66 or 67, wherein the sample is selected from whole blood, serum or plasma.
69. The antibody of any one of paragraphs 48-58, wherein said antibody or fragment thereof is selected by immunoselection or immunodepletion.
70. The antibody of any one of paragraphs 48-58, wherein said antibody or fragment thereof is detectably labeled.
71. A process for producing a polypeptide consisting essentially of the amino acid sequence of a non-human mammalian interferon, comprising causing a culture of a microorganism or cell culture transformed with an expression vector according to paragraph 5 to grow, effecting production of said polypeptide, and recovering said polypeptide.
72. A preparation of an isolated peptide of any one of paragraphs 13-15, said preparation demonstrating a specific activity of at least $1 \times 10^7$ U/mg in cytopathic effect assays in either LLC-MK2 cells using vesicular stomatitis virus or A549 cells using encephalomyocarditis virus.
73. A kit comprising antibody pairs or binding partner pairs or combinations thereof, said antibody pairs or binding partner pairs specifically bind one or more of the polypeptides of any one of paragraphs 13-15.
74. The kit of paragraph 73, capable of differentiating between one or more of the polypeptides of any one of paragraphs 13-15.
75. The kit of paragraph 73, capable of differentiating between one or more of the polypeptides of any one of paragraphs 13-15 from other polypeptides.
76. A kit comprising polynucleotides complementary to any one of the nucleic acids of paragraph 1 or 2, capable of specifically detecting one or more of said nucleic acids.
77. The kit of paragraph 76, capable of specifically differentiating between one or more of the nucleic acids of paragraph 1 or 2.
78. The kit of paragraph 76, capable of specifically differentiating between one or more of the nucleic acids of paragraph 1 or 2 from other nucleic acid sequences.
79. The kit of any one of paragraphs 76-78, further comprising reagents for performing polymerase chain reaction, reagents for detecting single nucleotide polymorphisms, single hairpin loops, or locked nucleic acids.
80. A method of measuring interferon bioactivity, comprising:
   (a) treating a cell with interferon wherein the interferon is active in a bioactivity assay comprising any one or more of:
      i. inhibition of proliferation of a mammalian cell;
      ii. inhibition of viral infection of a mammalian cell;
      iii. increase or decrease in the expression of MHC Class I and/or MHC Class II molecules on the surface of mammalian cells;
      iv. increase in expression of an IFN signal-responsive reporter construct;
      v. stimulation or inhibition of cytokine production by mammalian cells; or
      vi. any combination of any one of i-v; and
   (b) quantifying said responses, wherein the interferon in said bioactivity assay comprise of any one of the polypeptides in any one of paragraphs 13-15.
81. A method of measuring neutralizing antibody bioactivity, comprising:
   (a) treating a cell with interferon in combination with a biological sample;
   (b) waiting a specified amount of time;
   (c) assessing the effect of the biological sample on the interferon activity in a bioactivity assay, wherein the interferon bioactivity assay comprises measuring any one or more of:
      i. inhibition of proliferation of a mammalian cell;
      ii. inhibition of viral infection of a mammalian cell;
      iii. increase or decrease in expression of MHC Class I and/or MHC Class II molecules on the surface of mammalian cells;
      iv. increase in expression of an IFN signal-responsive reporter construct;
      v. stimulation or inhibition of cytokine production by mammalian cells; or
      vi. any combination of any one of i-v; and (d) quantifying said responses, wherein the interferon in the neutralizing antibody bioactivity assay comprises any one of the polypeptides in any one of paragraphs 13-15.

82. A method for detecting and/or measuring the concentration of a polypeptide of any one or more of paragraphs 13-15, in a matrix selected from culture supernatant, serum, plasma, extracellular fluid, whole blood, sputum, or nasal secretions, the method comprising:
(a) obtaining a sample of biological fluid from a subject; and
(b) analyzing the sample for the presence, activity, and/or concentration of said polypeptides using a technique selected from: an antibody-based detection method (preferably using an antibody raised against and/or specific for a polypeptide of any one of paragraphs 13-15), a binding-partner-based detection method, or a bioactivity assay.

83. The method of paragraph 82, wherein the detection and/or measurement method comprises an immunoassay which detects the polypeptide at a sensitivity of less than 25 pg/mL.

84. The method of paragraph 82, wherein the sensitivity is less than 10 pg/mL.

85. The method of paragraph 82, wherein the sensitivity is less than 5 pg/mL.

86. The method of paragraph 82, wherein the sensitivity is less than 1 pg/mL.

87. The method of paragraph 82, further comprising an antiviral assay.

88. The method of paragraph 82, wherein the assay is selected from a cytopathic effect inhibition assay, a viral yield reduction assay, a plaque assay, a reporter gene assay, a PCR-based assay, or an immunoassay.

89. The method of paragraph 82, for diagnosing an acute or chronic disease state, a pharmacological response, or a pharmacodynamic response to therapeutics or toxins, further comprising correlating directly or inversely the severity of the disease state or treatment response with the level of any one of said polypeptides as a biomarker, wherein:
the acute or chronic disease state is selected from a viral infection, a cancer, an autoimmune state, an immunocompromised state, a hyperimmune condition, or a hypoimmune condition; and
the pharmacological or pharmacodynamic response is to a pharmacological agent, a toxin, or therapeutic interventions representative of alteration in the subject's immune function or toxicological state.

90. The method of paragraph 89, wherein a polypeptide of any one of paragraphs 13-15 functions as an immunotoxicological marker correlating inversely or directly with any one of:
(a) a response to administration of pharmacological agents, toxins, or therapeutic interventions; or
(b) general toxicological state.

91. The method any one of paragraphs 82-90, wherein the subject is a non-human primate.

92. The method of any one of paragraphs 82-90, wherein the method is used to predict the effect of human interferons administered to humans.

93. The method of any one of paragraphs 82-90, wherein the method is used to determine the efficacy of an interferon in animal models of human disease.

94. The method of any one of paragraphs 82-90, wherein the method is used to determine a side effect profile of an interferon.

95. The method of any one of paragraphs 82-90, wherein the method is used to predict responses of higher primates to administration of an interferon and an agent to be used in combination with interferons.

96. A method of identifying an intervention that increases or decreases the expression of a polypeptide of any one of paragraphs 13-15, comprising:
(a) obtaining a biological sample;
(b) exposing the biological sample to an intervention;
(c) waiting a specified period of time;
(d) assessing a change in gene expression levels, levels of RNA, protein, or protein activity levels related to one or more biomarkers of immune function of subject toxicity; and
(e) identifying the intervention as one that results in altered expression of any one of the polypeptides of any one of paragraphs 13-15.

97. The method of paragraph 96, wherein the biological sample comprises cells.

98. The method of paragraph 97, wherein the cells are obtained from a mammal.

99. The method of paragraph 98, wherein the mammal is a non-human primate.

100. The method of paragraph 96, wherein the change in gene expression levels, levels of RNA, protein, or protein activity levels corresponds to a change in gene expression for a gene encoding a protein selected from a STAT protein, an ISG protein, an ISRE protein, and an IRF protein.

101. The method of any one of paragraphs 96-100, wherein the intervention is an agonist or antagonist for a Toll-Like Receptor, a NOD-Like Receptor, or a RIG-1-Like Receptor.

102. The method of any one of paragraphs 96-100, wherein the intervention is an immune response modulator.

Other features and advantages of the invention will be apparent from the detailed description, and from the claims.

It should be understood that all embodiments of the invention described herein (including those described under different aspects of the invention) are generally contemplated to be combinable with any one or more other embodiments of the invention, unless clearly not applicable or disclaimed.

BRIEF DESCRIPTION OF THE FIGURES

The invention and the following detailed description of certain embodiments thereof may be understood by reference to the following figures.

DETAILED DESCRIPTION OF THE INVENTION

I. Overview

Figure 1:
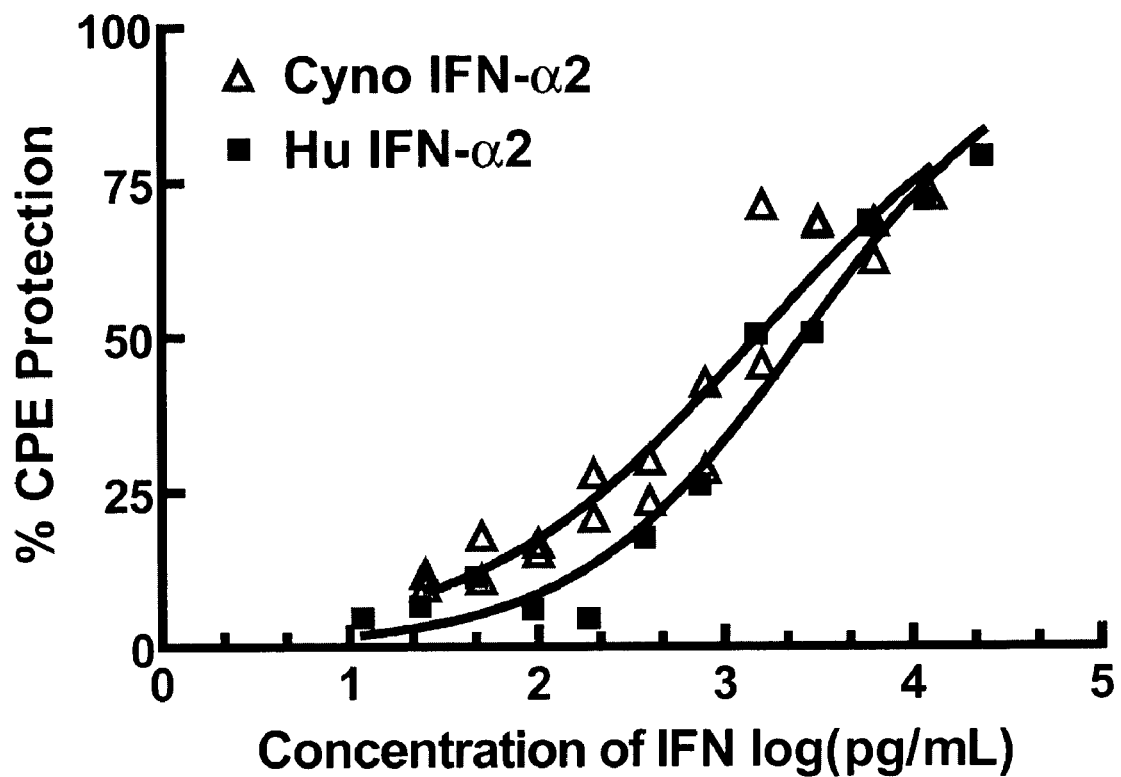
FIG. 1 depicts a cytopathic effect inhibition assay performed on Rhesus LLC-MK2 cells in which human interferon alpha 2 activity is compared to that of Cynomolgus interferon alpha 2 (SEQ ID NO: 66), both purified from inclusion bodies after expression in E. coli. Together with the results depicted in Table 1 (JTC 12 cells), these data demonstrate that the majority Cynomolgus interferon alpha proteins expressed either in E. coli or in mammalian cell culture supernatants exhibit protection of non-human primate cells from the cytopathic effects of viruses. This is a hallmark of interferon activity. Therefore, the classification of these proteins and their cognate DNAs as interferon alpha proteins and genes appears appropriate, and these specific examples suggest that all of the subject sequences will exhibit bioactivities indicative of interferon proteins.

The present invention provides isolated nucleic acid molecules comprising a polynucleotide encoding at least a portion or a fragment of the novel polypeptides described herein. In an embodiment, the novel polypeptides may be interferons, such as cytokine interferons.

In another aspect, the present invention provides isolated nucleic acid molecules comprising a polynucleotide encoding at least a portion of a polypeptide having the amino acid sequence shown in one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. More generally, a fragment or portion of an isolated nucleic acid molecule refers to fragments at least about 10 nucleotides, and more preferably at least about 20 nucleotides, still more preferably at least about 30 nucleotides, and even more preferably, at least about 40 nucleotides in length. Such fragments may be useful as diagnostic probes and primers as discussed herein. Of course, larger fragments 50-300 nucleotides in length may also be useful according to the present invention.

Further embodiments of the invention may comprise isolated nucleic acid molecules that comprise a polynucleotide which hybridizes under stringent hybridization conditions to a polynucleotide described in any of the SEQ IDs disclosed herein.

In another aspect, any of the nucleic acid molecules of the present invention which encode interferon polypeptides may include, but are not limited to, those encoding the amino acid sequence of the complete polypeptide and those that include the coding sequence for the complete polypeptide and additional sequences, such as those encoding an added secretory leader sequence, such as a pre-, or pro- or prepro-protein sequence. In some embodiments, the polypeptides may lack the signal sequence.

Also encoded by nucleic acids of the invention may be the above protein sequences together with additional, non-coding sequences, including, for example, but not limited to introns and non-coding 5' and 3' sequences, such as the transcribed, non-translated sequences that play a role in transcription, mRNA processing, including splicing and polyadenylation signals, for example-ribosome binding and stability of mRNA; and an additional coding sequence which codes for additional amino acids, such as those which may provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc.), among others, many of which are commercially available. For instance, hexa-histidine as described by Gentz et al. provides for convenient purification of the fusion protein (Gentz et al. *Proc. Natl. Acad. Sci. USA* 86, 821-824, 1989). The "HA" tag is another peptide useful for purification which corresponds to an epitope derived from the influenza hemagglutinin protein (Wilson et al. *Cell* 37, 767, 1984). As discussed below, other such fusion proteins include the polypeptide, such as an interferon polypeptide, fused to $F_c$ at the N- or C-terminus. In a related embodiment, the invention may also provide fusion proteins comprising an interferon/interleukin protein and a heterologous protein. In certain embodiments, the fusion proteins comprise at least a portion of the interferon/interleukin or a variant thereof and a second domain selected from an immunoglobulin element, a multimerizing domain, a targeting domain, a stabilizing domain, and a purification domain. Any one domain may perform many functions. For example, an $F_c$ domain may provide dimerization, facilitate purification and stabilize the protein in vivo. Exemplary heterologous proteins that may be used to generate interferon/interleukin fusion proteins include, but are not limited to, glutathione-S-transferase (GST), an enzymatic activity such as alkaline phosphatase (AP), or an epitope tag such as hemagglutinin (HA).

The present invention also relates to recombinant vectors, which include the isolated nucleic acid molecules of the present invention, and to host cells containing the recombinant vectors, as well as to methods of making such vectors and host cells and for using them for production of the polypeptides or peptides, including interferon polypeptides and fragments thereof, by recombinant techniques.

In another aspect, the invention provides an isolated polypeptide comprising an amino acid sequence selected from any of the SEQ IDs disclosed herein, with or without the signal sequence. In preferred embodiments, the invention provides an isolated polypeptide, or fragment thereof, comprising an amino acid sequence of an interferon described herein, such as one of the interferon polypeptides disclosed herein. The polypeptides of the present invention also include polypeptides having an amino acid sequence at least 80% identical, more preferably at least 90% identical, and still more preferably 95%, 96%, 97%, 98%, 99%, or 99.5% identical to any of those described in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, as well as polypeptides having an amino acid sequence with at least 90% similarity, and more preferably at least 98% similarity, to those above.

The invention also provides a peptide or polypeptide which comprises the amino acid sequence of an epitope-bearing portion of a polypeptide, such as an interferon polypeptide, having an amino acid sequence of any of the SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or fragments or variants thereof. Peptides or polypeptides having the amino acid sequence of an epitope-bearing portion of a polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a polypeptide having an amino acid sequence described in one of the SEQ IDs disclosed here. The invention further provides methods for isolating antibodies that bind specifically to the polypeptide having an amino acid sequence as described herein. Such antibodies may be useful therapeutically. In an embodiment, the antibodies may be specific for interferon polypeptides.

In another aspect, the invention provides compositions comprising any of the polynucleotides or polypeptides, including interferon polypeptides and polynucleotides, described herein, for administration to cells in vitro, to cells ex vivo, and to cells in vivo, or to a multicellular organism. In some embodiments, the compositions comprise an interferon polynucleotide for expression of an interferon polypeptide in a host organism for treatment of a disease or condition. Particularly preferred in this regard is expression in a subject for treatment of a dysfunction associated with loss of endogenous activity of an interferon, or for treatment of a viral infection or of a tumor.

The invention also provides for pharmaceutical compositions comprising interferon polypeptides which may be employed, for instance, to treat immune system-related disorders such as viral infection, parasitic infection, bacterial infection, cancer, autoimmune disease, multiple sclerosis, lymphoma and allergy. Methods of treating individuals in need of interferon polypeptides are also provided. In certain preferred embodiments, the subject pharmaceutical composition may be a veterinary composition for administration to a non-human animal, preferably a non-human primate. Exemplary conditions which may be treated with an interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T-cell lymphoma), and viral infections. Without limitation, treatment with interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6), papilloma, poxvirus, picornavirus, adenovirus, rhinovirus, human T lymphotrophic virus-type 1 and 2 (HTLV-1-2), human rotavirus, rabies, retroviruses including human immunodeficiency virus (HIV), encephalitis and respiratory viral infections. The method of the invention may also be used to modify various immune responses.

In some embodiments, the compositions comprise at least two interferons, such as an interferon and a second interferon. The second interferon may be a Type I or a Type II interferon. In an embodiment, the second interferon is an IFN-α, an IFN-β, or an IFN-γ polypeptide. In another embodiment, the second interferon is an IFN-δ, IFN-ω, or IFN-ν polypeptide.

In yet another embodiment, the subject interferons may be used as anti-cancer agents. Interferon therapy using the subject interferons may be used in the treatment of numerous cancers. e.g., hairy cell leukemia, acute myeloid leukemia, osteosarcoma, basal cell carcinoma, glioma, renal cell carcinoma, multiple myeloma, melanoma, and Hodgkin's disease.

In yet another embodiment, the subject interferons may be used as part of an immunotherapy protocol. The interferons of the present invention may be used clinically for immunotherapy or more particularly, for example, to prevent graft vs. host rejection, or to curtail the progression of autoimmune diseases, such as arthritis, multiple sclerosis, or diabetes. In another embodiment, the subject interferons may be used as part of a program for treating allergies.

In still another embodiment, the subject interferons may be used as vaccine adjuvants. The subject interferons may be used as an adjuvant or coadjuvant to enhance or stimulate the immune response in cases of prophylactic or therapeutic vaccination.

The subject invention also contemplates functional antagonists, e.g., wherein one or more amino acid residues are different from the wild-type interferon, which inhibit one or more biological activities of the wild-type interferon. Such antagonists may be used to treat disorders resulting from aberrant over expression or other activation of an endogenous interferon. The functional antagonists may be formulated in a pharmaceutical preparation.

The present invention also provides a screening method for identifying compounds capable of enhancing or inhibiting a biological activity of one of the polypeptides described herein. In the exemplary case where the polypeptide is an interferon, this may involve contacting a receptor which is enhanced by an interferon polypeptide with the candidate compound in the presence of an interferon polypeptide, assaying, for example, anti-viral activity in the presence of the candidate compound and an interferon polypeptide, and comparing the activity to a standard level of activity, the standard being assayed when contact is made between the receptor and interferon in the absence of the candidate compound. In this assay, an increase in activity over the standard indicates that the candidate compound is an agonist of interferon activity and a decrease in activity compared to the standard indicates that the compound is an antagonist of interferon activity.

One aspect of the invention provides screening assays for drug candidates to identify compounds that competitively bind or complex with the receptor(s) of the interferons described herein and signal through such receptor(s). Such screening assays may include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays may be performed in a variety of formats, including protein-protein binding assays, biochemical screening assays, immunoassays and cell based assays, which are well characterized in the art.

An additional aspect of the invention may be related to a method for treating an animal in need of an increased level of interferon activity in the body comprising administering to such an animal a composition comprising a therapeutically effective amount of an isolated interferon polypeptide of the invention or an agonist thereof. A still further aspect of the invention may be related to a method for treating an animal in need of a decreased level of interferon activity in the body comprising, administering to such an animal a composition comprising a therapeutically effective amount of an interferon antagonist. Preferred antagonists for use in the present invention are interferon-specific antibodies.

The amount of the interferon composition administered to treat the conditions described above may be based on the interferon activity of the composition. It may be an amount that is sufficient to significantly effect a positive clinical response. Although the clinical dose may cause some level of side effects in some animals, the maximal dose for animals including humans is the highest dose that does not cause unmanageable clinically-important side effects. For purposes of the present invention, such clinically important side effects are those which would require cessation of therapy due to severe flu-like symptoms, central nervous system depression, severe gastrointestinal disorders, alopecia, severe pruritus or rash substantial white and/or red blood cell and/or liver enzyme abnormalities or anemia-like conditions are also dose limiting. Naturally, the dosages of interferon may vary somewhat depending upon the formulation, selected. In general, however, the interferon composition may be administered in amounts ranging from about 100,000 to about several million IU/m$^2$ per day, based on the animal's condition. The range set forth above is illustrative and those skilled in the art will determine the optimal dosing of interferon selected based on clinical experience and the treatment indication. The pharmaceutical compositions may be in the form of a solution, suspension, tablet, capsule, lyophilized powder or the like, prepared according to methods well known in the art. It is also contemplated that administration of such compositions will be chiefly by the parenteral route although oral or inhalation routes may also be used depending upon the needs of the artisan.

The invention further provides methods of detecting the level of gene expression of an interferon gene in an animal. Such methods may involve detection of interferon polypeptide or mRNA levels. Polypeptide levels may be quantified from a sample derived from the animal using an antibody, while mRNA levels may be quantified using, for example, Northern blots, RT-PCR amplification, and DNA microarrays.

In an aspect of the invention, there may be a method for identifying compounds that enhance or inhibit the biological activity of an interferon polypeptide. In an embodiment, there may be a method for identifying compounds that enhance or inhibit the biological activity of an interferon polypeptide as described herein, wherein a compound which enhances the biological activity of an interferon polypeptide is an interferon agonist. In an embodiment, a compound which inhibits the biological activity of an interferon polypeptide may be an interferon antagonist.

In an aspect of the invention, a process for producing a polypeptide may consist essentially of the amino acid sequence of a non-human mammalian interferon comprising causing a culture of a microorganism or cell culture transformed with an expression vector as described herein to grow and effect production of said polypeptide and recovering said polypeptide.

In an aspect of the invention, a preparation of an isolated peptide as described herein may demonstrate activity of at least $1\times10^7$ U/mg in cytopathic effect assays in either LLC-MK2 cells using vesicular stomatitis virus or A549 cells using encephalomyocarditis virus.

In an aspect of the invention, a kit may be provided for detecting one or more of the polypeptides described herein.

In an aspect of the invention, a kit may be provided for differentiating between one or more of the polypeptides as described herein.

In an aspect of the invention, a kit may be provided for differentiating one or more of the polypeptides as described herein from similar polypeptides.

In an aspect of the invention, a kit may be provided for specifically detecting one or more of the nucleic acids as described herein. In an aspect of the invention, a kit may be provided for specifically differentiating between one or more of the nucleic acids as described herein. In an aspect of the invention, a kit may be provided for specifically differentiating one or more of the nucleic acids as described herein from similar nucleic acid sequences. In an embodiment of any of these aspects, a kit may utilize polymerase chain reaction, single nucleotide polymorphisms, single hairpin loops, or locked nucleic acids.

In an aspect of the invention, the polypeptides may serve as activity standards in assays of interferon bioactivity.

In an aspect of the invention, the polypeptides may serve as activity standards in assays of anti-interferon neutralizing antibody bioactivity.

In an aspect of the invention, the polypeptide as described herein may exhibit specific activity of at least $1\times10^7$ U/mg in a cytopathic effect assay using LLC-MK2 cells and Vesicular Stomatitis Virus. In an embodiment, the polypeptide may be expressed in microbial cells and exhibits the cytopathic inhibition activity of this aspect of the invention. In an embodiment, the polypeptide may be expressed in eukaryotic cells and exhibits the cytopathic inhibition activity of this aspect of the invention. In an embodiment, the polypeptide may be expressed in mammalian cells and exhibits the cytopathic inhibition activity of this aspect of the invention. In an embodiment, the polypeptide may be expressed in insect cells and exhibits the cytopathic inhibition activity of this aspect of the invention. In an embodiment, the polypeptide may be expressed in yeast cells and exhibits the cytopathic inhibition activity of this aspect of the invention.

Figure 3:
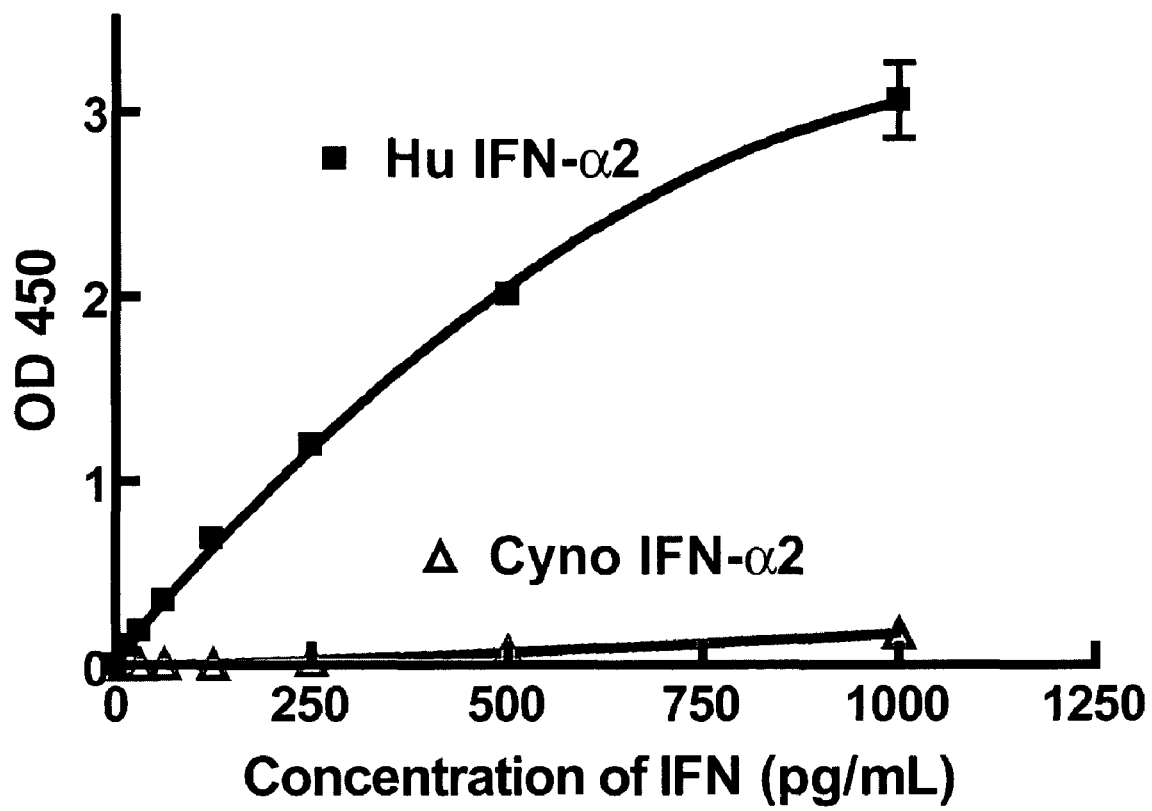
FIG. 3 depicts an ELISA assay assessing the reactivity of the ELISA toward human interferon alpha 2 and Rhesus interferon alpha 2, and Cynomolgus interferon alpha 2 (SEQ ID NO: 66), both purified from inclusion bodies after expression in *E. coli*. Together with the results depicted in Table 3, these data demonstrate that the Cynomolgus interferon alpha proteins expressed either in *E. coli* or in mammalian cell culture supernatants are recognized by ELISAs directed against interferon alpha.

In an aspect of the invention, a method may detect and/or measure the concentration of the polypeptide as described herein in a variety of matrices including culture supernatant, serum, plasma, extracellular fluid, whole blood, sputum, and nasal secretions. In an embodiment, the detection and/or measurement method may comprise immunoassays such as ELISAs, ECL and others which detect these molecules at less than 25 pg/mL. In an embodiment, the detection and/or measurement method may comprise immunoassays such as ELISAs, ECL and others which detect these molecules at less than 10.0 pg/mL. In an embodiment, the detection and/or measurement method may comprise immunoassays such as ELISAs, ECL and others which detect these molecules at less than 5 pg/mL. In an embodiment, the detection and/or measurement method may comprise immunoassays such as ELISAs, ECL and others which detect these molecules at less than 1 pg/mL. The graph in FIG. 3 illustrates the need for such a kit as ELISA kit designed to detect human interferons (PBL Biomedical Laboratories Product #41100-1) is not sufficiently reactive to quantify low levels of specific non-human primate. In an embodiment, the detection and/or measurement method may comprise antiviral assays including cytopathic effect inhibition assays and viral yield reduction assays. In an embodiment, the assay may be a cytopathic effect assay. In an embodiment, the assay may be a viral yield reduction assay. In an embodiment, the assay may be a plaque assay. In an embodiment, the assay may be a reporter gene assay. In an embodiment, the assay may be a PCR-based assay. In an embodiment, the assay is an immunoassay. In an embodiment, the polypeptides as described herein may function as biomarkers correlating with one or more of: (i) particular acute or chronic disease states, comprising: Viral infections, Cancer, Autoimmune states, Immunocompromised states, Other hyper- or hypoimmune conditions; (ii) Responses to administration of pharmacological agents, toxins, or therapeutic interventions; (iii) General immune function; and (iv) General toxicology. In an embodiment, the polypeptides as described herein may function as immunotoxicological markers correlating with one or more of: (i) particular acute or chronic disease states, comprising: Viral infections, Cancer, Autoimmune states, Immunocompromised states, Other hyper- or hypoimmune conditions; (ii) Responses to administration of pharmacological agents, toxins, or therapeutic interventions; (iii) General immune function; and (iv) General toxicology. In an embodiment, the subject may be a non-human primate. The method may be used to predict the effect of human interferons administered to humans. The method may be used to determine the efficacy of interferon in animal models of human disease. The method may be used to determine the side effect profile of interferons. The method may be used to predict responses of higher primates to administration of interferons and agents to be used in combination with interferons.

In an aspect of the invention, a method of identifying an intervention that increases or decreases the expression of any of the polypeptides described herein may comprise: obtaining a biological sample; exposing said biological sample to an intervention; waiting a specified period of time; assessing changes in gene expression levels, levels of RNA, protein, or protein activity levels related to one or more biomarkers of immune function of subject toxicity; and identifying said intervention as one that results in altered expression of any of the polypeptides as described herein. In an embodiment, the biological sample comprises cells. The cells may be obtained from a mammal. The mammal may be a non-human primate. In an embodiment, said change in gene expression levels, levels of RNA, protein, or protein activity levels may correspond to a change in gene expression for a gene encoding any one of a STAT, ISG, ISRE, and IRF protein. In an embodiment, intervention may be a Toll-Like Receptor agonist or antagonist. In an embodiment, intervention may be an immune response modulator.

II. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article, unless context clearly indicates otherwise. By way of example, "an element" means one element or more than one element.

The term "or" is used herein to mean, and is used interchangeably with, the term "and/or", unless context clearly indicates otherwise.

The term "including" is used herein to mean, and is used interchangeably with, the phrase "including but not limited to".

The term "antibody" as used herein is intended to include whole antibodies, e.g., of any isotype (IgG, IgA, IgM, IgE, etc), and includes fragments thereof, including fragments which also may be specifically reactive with a vertebrate, e.g., mammalian, protein. Antibodies may be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

A "chimeric polypeptide" or "fusion polypeptide" is a fusion of a first amino acid sequence with a second amino acid sequence where the first and second amino acid sequences are not naturally present in a single polypeptide chain.

The term "detection", in addition to art-recognized meanings, is intended to refer to any process of observing a marker, in a biological sample, whether or not the marker is actually detected. In other words, the act of probing a sample for a marker is a "detection" even if the marker is determined to be not present or below the level of sensitivity. Detection may be a quantitative, semi-quantitative or non-quantitative observation.

A "binding partner" is any protein molecule or chemically modified protein molecule which is reactive with another protein, such as being specifically reactive with a vertebrate, e.g., mammalian, protein. Fragments of antibody protein sequence may be genetically engineered using conventional techniques into any of several binding partner scaffolds. Alternatively, peptide sequences may be inserted into any of several peptide or organic scaffolds. Thus, the term includes segments of proteolytically-cleaved or recombinantly-prepared portions of an antibody molecule that are capable of selectively reacting with a certain protein that may then be inserted into i) an alternative protein backbone, ii) a organic chemical scaffold, and/or iii) a peptide backbone. Non-limiting examples of such backbones or scaffolds include fibronectins, transferring, anticalins, lipocalins, phylomers, CycloTriVeratrylene, TriAzaCyclophane, Shark New Antigen Receptor, and/or peptide aptamers and/or the like.

An "expression construct" is any recombinant nucleic acid that includes an expressible nucleic acid and regulatory elements sufficient to mediate expression in a suitable host cell. For example, an expression construct may contain a promoter or other RNA polymerase contact site, a transcription start site or a transcription termination sequence. An expression construct for production of a protein may contain, for example a translation start site, such as an ATG codon, a ribosome binding site, such as a Shine-Dalgarno sequence, and/or a translation stop codon.

The term "isolated" as used in reference to nucleic acids (such as DNA or RNA) or polypeptides, indicates a nucleic acid or polypeptide, such as an interferon nucleic acid or polypeptide, that is removed from its natural context, or separated from other DNAs/RNAs or polypeptides that are present in the natural source of the macromolecule. The term isolated also refers to a nucleic acid or peptide that is substantially free of cellular material or culture medium when produced by recombinant DNA techniques, or chemical precursors or other chemicals when chemically synthesized. For example, an "isolated" polypeptide may be substantially free of other proteins and certain other compounds that are normally associated with it. As another example, an "isolated" nucleic acid may be removed from its normal genomic context and recombined with other nucleic acids, such as a cloning vector. Moreover, an "isolated nucleic acid" is meant to include nucleic acid fragment which are not naturally occurring as fragments and would not be found in the natural state.

A "knock-out" of a gene means an alteration in the sequence of the gene that results in a decrease of function of the target gene, preferably such that target gene expression is undetectable or insignificant. For example, a knock-out of an endogenous interferon gene means that function of the endogenous interferon gene has been substantially decreased. "Knock-out" transgenics can be transgenic animals having a heterozygous knock-out of the interferon gene or a homozygous knock-out of the interferon gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased) of the target gene, e.g., by introduction of an additional copy of the target gene, or by operatively inserting a regulatory sequence that provides for enhanced expression of an endogenous copy of the target gene. "Knock-in" transgenics of interest for the present invention can be transgenic animals having a knock-in of the animal's endogenous interferon. Such transgenics can be heterozygous knock-in for the interferon gene, homozygous for the knock-in of the interferon gene and the like. "Knock-ins" may also encompass conditional knock-ins.

The term "nucleic acid" includes, in addition to any art recognized meaning, polynucleotides such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, intratumoral, and intrasternal injection and infusion, and the like.

The terms "polypeptide" and "protein" are used interchangeably herein.

The term "purified protein" refers to a preparation of a protein or proteins which are preferably isolated from, or otherwise substantially free of, other proteins and certain other molecules normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins may be prepared as purified preparations by using a cloned gene as described. By "purified" it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "recombinant" as used in reference to a nucleic acid indicates any nucleic acid that is positioned adjacent to one or more nucleic acid sequences that it is not found adjacent to in nature or presently known to be found adjacent to in nature. A recombinant nucleic acid may be generated in vitro, for example by using the methods of molecular biology, or in vivo, for example by insertion of a nucleic acid at a novel chromosomal location by homologous or non-homologous recombination. The term "recombinant" as used in reference to a polypeptide indicates any polypeptide that is produced by expression and translation of a recombinant nucleic acid.

The term "specific," as used to describe antibody binding, refers to the situation that the antibody has a substantially higher binding affinity/selectivity for one (intended) antigen compared to another (e.g., cross-reacting) antigen. Antibody (or functional fragment thereof) of the subject invention that "specifically" binds a target antigen (such as one of the polypeptide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68) preferably has a kd at least about 2-fold, 5-fold, 10-fold, 20-fold, 50-fold, 100-fold lower than that for a cross-reacting antigen (such as a human interferon polypeptide).

The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The term "transgene" is used herein to describe genetic material which has been or is about to be artificially inserted into the genome of an animal, particularly a mammalian cell of a living animal.

By "transgenic animal" is meant a non-human organism, usually a mammal (e.g., mouse, rat, rabbit, hamster, etc.), having a non-endogenous nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

As used herein, the term "PEG moiety" is intended to include, but is not limited to, linear and branched PEG, methoxy PEG, hydrolytically or enzymatically degradable PEG, pendant PEG, dendrimer PEG, copolymers of PEG and one or more polyols, and copolymers of PEG and PLGA (poly (lactic/glycolic acid)) and the like. According to the present invention, the term polyethylene glycol or PEG is meant to comprise native PEG as well as derivatives thereof.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, endometrial carcinoma, salivary gland carcinoma, kidney cancer, vulval cancer, thyroid cancer, hepatic carcinoma and various types of head, neck cancer, and the like.

"Treatment" is an intervention performed with the intention of preventing the development or altering the pathology of a disorder. The term "treatment" is intended to encompass also prophylaxis, therapy, cure, and the like. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy. Similarly, in the treatment of virus infections, the therapeutic agent may treat the infection directly, or increase the efficacy of other antiviral treatments, e.g. by upregulating the immune system of the subject.

"Chronic" administration refers to administration of the agent(s) in a continuous mode as opposed to an acute mode, so as to maintain the initial biological effect for an extended period of time.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder.

A "therapeutically effective amount" in the context of antiviral activity is an amount capable of invoking one or more of the following effects: (1) at least partial killing of the virus causing the infection; (2) enhancement of anti-viral immune response; (3) relief, to some extent, of one or more symptoms associated with the disorder.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™, and the like Administration "in combination with" one or more further therapeutic agents includes simultaneous (concurrent) and consecutive administration in any order.

The term "antagonist" is used in the broadest sense, and includes any molecule that partially or fully blocks, inhibits, or neutralizes a biological activity of a native interferon polypeptide disclosed herein. In a similar manner, the term "agonist" is used in the broadest sense and includes any molecule that mimics a biological activity of a native interferon polypeptide disclosed herein.

A "small molecule" is defined herein to have a molecular weight below about 1000 Daltons, preferably below 500 Daltons.

By a polynucleotide which hybridizes to a "portion" of a polynucleotide is intended a polynucleotide (either DNA or RNA) hybridizing to a sequence of nucleotides, typically at least about 15 nucleotides, and more preferably at least about 20 nucleotides, still more preferably at least about 30 nucleotides, and even more preferably about 30 to about 70 (e.g., 50) nucleotides of the reference polynucleotide. These are useful as diagnostic probes and primers.

A "mature protein" is a protein that is produced by cellular processing of a primary translation product of a DNA sequence. Such processing may include removal of a secretory signal peptide, sometimes in combination with a propeptide. Mature sequences can be predicted from full-length sequences using methods known in the art for predicting cleavage sites (see, for example, von Heijne *Nucleic Acids Res.* 14, 4683, 1986; Bendtsen et al. *J. Mol. Biol.* 340, 783-95, 2004; Hiller et al., *Nucleic Acids Res.* July 1; 32(Web Server issue):W375-9, 2004). The sequence of a mature protein can be determined experimentally by expressing a DNA sequence of interest in a eukaryotic host cell and determining the amino acid sequence of the final product. For proteins lacking secretory peptides, the primary translation product will be the mature protein.

The terms "microarray," "GeneChip," "genome chip," and "biochip," as used herein refer to an ordered arrangement of hybridizable array elements. The array elements are arranged so that there are preferably at least one or more different array elements on a substrate surface, such as paper, nylon or other type of membrane, filter, chip, glass slide, or any other suitable solid support. The hybridization signal from each of the array elements is individually distinguishable.

Throughout this disclosure the phrase "for example" means "for example and without limitation". Throughout this disclosure the phrase "such as" means "such as and without limitation." Generally, any and all examples may be provided for the purpose of illustration and not limitation.

III. Nucleic Acids

The present invention provides isolated nucleic acid molecules comprising a polynucleotide such as any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67 and others encoding at least a portion of a polypeptide having an amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. Thus, one aspect of the invention provides an isolated polynucleotide comprising a nucleotide sequence selected from the group consisting of: (a) a nucleotide sequence encoding a polypeptide including an amino acid sequence in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68; (b) a nucleotide sequence encoding a biologically active fragment of a polypeptide shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68; and (c) a nucleotide sequence complementary to at least one of any of the nucleotide sequences in (a) or (b) above. In some embodiments, the polypeptide is one of the interferon polypeptides set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68.

One aspect of the invention provides an isolated nucleic acid encoding a polypeptide, wherein the polypeptide has an amino acid sequence that is at least 99%, 99.3, 99.6% or 100% identical to at least 10, 12, 14, 16, 20, 22, 24, 25, 30, 35, 40, 50, 60, 70, 80, 90, 100, 110, 120, 130, 140, 150 contiguous amino acids of one of the sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68.

In an embodiment, the interferon polypeptide, such as the interferon polypeptide, is a mature protein. In another embodiment, the IFN polypeptide does not comprise a signal sequence.

In certain aspects the invention provides isolated and/or recombinant nucleic acids encoding interferon polypeptides, interferon receptor polypeptides, interleukin polypeptides and interleukin receptor polypeptides, such as, for example, SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. Nucleic acids of the invention are further understood to include nucleic acids that comprise variants of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67, e.g. due to the degeneracy of the genetic code. For example, nucleic acids encoding interferon polypeptide, receptor, or fragments thereof, may be nucleic acids comprising a sequence that is at least 95%, 99% or 100% identical to a sequence set forth in any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67, or a sequence that encodes the polypeptide of any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68.

One aspect of the invention provides nucleic acid fragments comprising sequences identical to a fragment of any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67. In an embodiment, such fragment is at least about 15 nucleotides, and more preferably at least about 20 nucleotides, still more preferably at least about 30 nucleotides, and even more preferably, at least about 40 nucleotides in length which are useful as diagnostic probes and primers as discussed herein. Of course, larger fragments 50-300 nucleotides in length are also useful according to the present invention as are fragments corresponding to most, if not all, of at least one of the nucleotide sequences shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67. Another aspect of the invention provides isolated polypeptides encoded by these nucleic acids.

Isolated nucleic acids which differ from the sequences set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. One skilled in the art will appreciate that these variations in one or more nucleotides of the nucleic acids encoding a particular protein may exist among individuals of a given species due to natural allelic variation. Any and all such nucleotide variations and resulting amino acid polymorphisms are within the scope of this invention.

In an aspect, the polynucleotide comprises a sequence encoding the amino acid methionine attached to the N-terminus of the ordinarily first amino acid of said non-human mammalian interferon. In another aspect, the polynucleotide comprises a sequence encoding a cleavable conjugate or signal protein attached to the N-terminus of the ordinarily first amino acid of said non-human mammalian interferon.

Optionally, a nucleic acid of the invention encoding an interferon polypeptide, receptor, or fragments thereof, will genetically complement a partial or complete loss of function phenotype in the corresponding gene. For example, an interferon nucleic acid of the invention may be expressed in a cell in which endogenous interferon has been knocked out, and the introduced interferon nucleic acid will mitigate a phenotype resulting from the knockout.

In certain aspects, nucleic acids encoding interferon polypeptides, receptors, or fragments thereof, and variants thereof may be used to increase expression of the gene in an organism or cell by direct delivery of the nucleic acid. A nucleic acid therapy construct of the present invention can be delivered, for example, as an expression plasmid which, when transcribed in the cell, produces RNA which encodes an interferon polypeptide, receptor, or fragments thereof.

In another aspect, nucleic acid encoding an interferon polypeptide, receptor, fragment thereof, or variants thereof, may be used to decrease gene expression. Such a nucleic acid therapy construct can be delivered, for example, as an expression plasmid which, when transcribed in the cell, produces RNA which is complementary to at least a unique portion of the cellular mRNA which encodes an interferon polypeptide. Alternatively, the construct is an oligonucleotide which is generated ex vivo and which, when introduced into the cell causes inhibition of expression by hybridizing with the mRNA and/or genomic sequences encoding the interferon polypeptide. Such oligonucleotide probes are optionally modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al. *Biotechniques* 6, 958-976, 1988; and Stein et al. *Cancer Res.* 48, 2659-2668, 1988.

Another aspect of the invention relates to the use of RNA interference (RNAi) to effect knockdown of the interferon polypeptide and receptor genes described herein. RNAi constructs comprise double stranded RNA that may specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in PCT Publication Nos. WO 01/68836 and WO 01/75164.

Ribozyme molecules designed to catalytically cleave an mRNA transcript can also be used to prevent translation of mRNA (see, e.g., PCT Publication No. WO90/11364; Sarver et al. *Science* 247, 1222-1225, 1990; and U.S. Pat. No. 5,093, 246). While ribozymes that cleave mRNA at site-specific recognition sequences can be used to destroy particular mRNAs, the use of hammerhead ribozymes is preferred.

Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature,* 334, 585-591, 1988. The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al. *Science* 224, 574-578, 1984; Zaug and Cech, *Science* 231, 470-475, 1986; Zaug et al. *Nature* 324, 429-433, 1986; PCT Publication No. WO 88/04300 by University Patents Inc.; Been and Cech *Cell* 47, 207-216, 1986). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells produce sufficient quantities of the ribozyme to destroy targeted messages and inhibit translation. Because ribozymes unlike antisense molecules, are catalytic, a lower intracellular concentration may be required for efficiency.

A further aspect of the invention relates to the use of DNA enzymes to inhibit expression of the interferon polypeptide and receptor genes described herein. DNA enzymes incorporate some of the mechanistic features of both antisense and ribozyme technologies. DNA enzymes are designed so that they recognize a particular target nucleic acid sequence, much like an antisense oligonucleotide. But much like a ribozyme they are catalytic and specifically cleave the target nucleic acid.

Briefly, to design an ideal DNA enzyme that specifically recognizes and cleaves a target nucleic acid, one of skill in the art must first identify the unique target sequence. Preferably, the unique or substantially unique sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Additionally, one of skill in the art will recognize that, like antisense oligonucleotide, DNA enzymes can be optionally modified to improve stability and improve resistance to degradation.

Accordingly, the modified oligomers of the invention are useful in therapeutic, diagnostic, and research contexts. In therapeutic applications, the oligomers are utilized in a manner appropriate for nucleic acid therapy in general.

In addition to use in therapy, the oligomers of the invention may be used as diagnostic reagents to detect the presence or absence of the interferon gene and receptor gene DNA or RNA sequences, such as for determining the level of expression of the gene or for determining whether the gene of the invention contains a genetic lesion.

In another aspect of the invention, the subject nucleic acid is provided in an expression vector comprising a nucleotide sequence encoding a subject interferon polypeptide, receptor, or fragment thereof, operably linked to at least one regulatory sequence. Regulatory sequences are art-recognized and are selected to direct expression of the polypeptide, or fragment. Accordingly, the term regulatory sequence includes promoters, enhancers and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an interferon polypeptide, receptor, or fragment thereof. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs may be used to cause expression of the subject polypeptides in cells propagated in culture, such as and without limitation to produce proteins or polypeptides, including fusion proteins or polypeptides, for purification.

The nucleic acids provided by the invention may be used as probes. Probes may also be employed in PCR techniques to generate a pool of sequences for identification of closely related interleukin or interferon sequences, such as interferon sequences. Probes may be included in a kit for detecting the polynucleotides of the invention, closely related interleukin or interferon sequences, differentiating between the polynucleotides of the invention, differentiating between the polynucleotides of the invention and similar sequences, and the like. The kit may utilize the polymerase chain reaction, single nucleotide polymorphisms, single hairpin loops, locked nucleic acids, and the like.

Nucleotide sequences encoding the interleukin and interferon polypeptides described herein can also be used to construct hybridization probes for mapping the gene which encodes the interferon and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleotide sequences (or their complement) encoding interferons have various applications in the art of molecular biology, including uses as hybridization probes, in chromosome and gene mapping and in the generation of anti-sense RNA and DNA. IFN-encoding nucleic acids may also be useful for the preparation of IFN polypeptides by the recombinant techniques described herein.

The full-length native sequence gene encoding the interferon sequences reported herein, or portions thereof, may be used as hybridization probes for a cDNA library to isolate the full-length gene or to isolate still other genes (for instance, those encoding naturally-occurring variants of interferon from other species). Optionally, the length of the probes will be about 20 to about 50 bases. By way of example, a screening method will comprise isolating the coding region of the interferon gene using the known DNA sequence to synthesize a selected probe of about 40 bases. Hybridization probes may be labeled by a variety of labels, including radionucleotides such as 32P or 35S, or enzymatic labels such as alkaline phosphatase coupled to the probe via avidin/biotin coupling systems. Labeled probes having a sequence complementary to that of the interferon gene of the present invention may be used to screen libraries of human cDNA, genomic DNA or mRNA to determine members of such libraries to which the probe hybridizes to.

Methods of alignment of sequences for comparison are well known in the art. Optimal alignment of sequences for comparison may be conducted by the local homology algorithm of Smith and Waterman, *Adv. Appl. Math.* 2, 482, 1981; by the homology alignment algorithm of Needleman and Wunsch, *J. Mol Biol.* 48, 443, 1970; by the search for similarity method of Pearson and Lipman, *Proc. Natl. Acad. Sci. USA* 8, 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp *Gene* 73, 237-244, 1988; Higgins and Sharp, CABIOS:11-13, 1989; Corpet, et al., *Nucleic Acids Res.* 16, 881-890, 1988; Huang, et al. *Comput. Appl. Biosci.* 8, 1-7, 1992; and Pearson, et al., *Methods in Molecular Biology* 24, 7-331, 1994. The BLAST family of programs which may be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and may be used with the present invention.

It will be clear to one skilled in the art that the nucleic acids and corresponding polypeptide sequences provided herein exhibit homology to and may be grouped into families based on sequence homology to Rhesus sequences currently available in Genbank. Both Rhesus and Cynomolgus nucleic acid and polypeptide sequences of the invention bear homology to published Rhesus sequences. Non-limiting examples of Cynomolgus nucleic acid sequences homologous to published Rhesus nucleic acid sequences include:

SEQ ID NO: 65 which is highly related to Macaca mulatta alpha 2 (Genbank accession #XM_001107516).

The group consisting of SEQ ID NO: 43, SEQ ID NO: 45, SEQ ID NO: 47, SEQ ID NO: 51, SEQ ID NO: 55 and SEQ ID NO: 63 are highly related to genes of the Macaca mulatta alpha 4 family (Genbank accession #XM_001107940).

XM_001107884, XM_001107817, XM_001107754, XM_001107693, XM_001107635).

SEQ ID NO: 59 which is highly related to Macaca mulatta alpha 8 (Genbank accession #XM_001107458).

The group consisting of SEQ ID NO: 49 and SEQ ID NO: 57 are highly related to Macaca mulatta alpha 14 (Genbank accession #XM_001107576).

The group consisting of SEQ ID NO: 41, SEQ ID NO: 61 and SEQ ID NO: 67 are highly related to Macaca mulatta alpha 17 (Genbank accession #XM_001107999).

SEQ ID NO: 53 which is highly related to Macaca mulatta alpha 21 (Genbank accession #XM_001108051).

IV. Proteins

In certain aspects, the invention provides interferon polypeptides, receptors, or fragments thereof, of various mammals and non-mammalian organisms, and functional variants thereof. Preferred functional variants of interferon polypeptides may be those that have immunomodulatory, antiviral and/or antiproliferative activity. In certain aspects, the present invention includes the full-length interferon protein and variants of these proteins, which include biologically-active fragments of the proteins and fusion proteins including at least a portion of the interferon polypeptides. These include proteins with antiviral and/or antiproliferative activity that have amino acid substitutions or have sugars or other molecules attached to amino acid functional groups. The term "variants" also encompasses homologous genes of xenogeneic origin. Typically, IFN variants will retain all, a substantial proportion, or at least partial biological activity as, for example, can be determined using the interferon bioassays provided herein.

In certain aspects, the present disclosure makes available isolated and/or purified forms of interferon polypeptides and receptors, which may be isolated from, or otherwise substantially free of, other proteins which might normally be associated with the protein or a particular complex including the protein. In certain embodiments, an interferon polypeptide is any polypeptide having at least 99%, 99.3, 99.6% or 100% identity to an amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these interferon polypeptides. In some embodiments, the invention provides polypeptides identical to either the full-length or the mature forms of the interferons of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, wherein one or more cysteine residues are replaced with another residue, preferably a serine residue. Other preferred residues with which the cysteine may be substituted include alanine and threonine.

The invention provides polypeptides without signal peptides and polypeptides having them. Signal peptides are normally cleaved from proteins post-translationally such that they are absent from the mature form of the protein. Accordingly, one aspect of the invention may provide the mature forms of the interferon polypeptides set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, and variants thereof. For example, a process may comprise expressing a nucleic acid molecule as described herein in a form unaccompanied by the signal peptide or presequence peptide that is the immediate product of the translation of the mRNA of said non-human mammalian interferon in a microorganism or cell culture. The microorganism may be obtained by transforming an *E. coli* strain. The culture of transformed cells may produce non-human mammalian interferon in a form unaccompanied by a signal peptide or presequence peptide that is the immediate product of the translation of the mRNA of said non-human mammalian interferon.

In certain embodiments, an interferon polypeptide may be a polypeptide comprising a portion of an amino acid sequence at least 99%, 99.3, 99.6% or 100% identical to the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these IFN polypeptides, wherein said portion is a functional portion, such as a portion that retains a substantial anti-viral, anti-proliferative, or immunomodulatory activity. By substantial activity, it is meant that the portion of the polypeptide retains, on a molar basis, at least 20%, 30%, 40%, 50%, 60%, 70%, 80%, 90% or 95% of the antiviral or anti-proliferative of the mature protein. In certain related embodiments, the present invention also includes fragments of the full-length IFN polypeptides of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. In one embodiment, the fragments are N- or C-terminal fragments, preferably fragments having anti-viral activity or anti-proliferative or immunomodulatory activity or combinations thereof.

The invention further provides interferon polypeptides, obtained when a nucleic acid comprising a nucleic acid sequence at least 95%, such as 95%, 96%, 97%, 98%, 99%, 99.5%, or 100%, identical to a nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67 is expressed in a cell. In an embodiment, the cell may be a mammalian cell. In certain embodiments, the interferon polypeptide may be purified or partially purified. Optionally, an interferon polypeptide of the invention may function in place of an endogenous interferon polypeptide, for example, by mitigating a partial or complete loss of function phenotype in a cell. In an exemplary embodiment, an interferon polypeptide may be produced in a cell in which the endogenous interferon polypeptide has been reduced, and the introduced interferon polypeptide may mitigate a phenotype resulting from the reduction in endogenous expression.

In another aspect, the invention provides polypeptides that may be agonists or antagonists of an interferon polypeptide. Variants of an interferon polypeptide may have a hyperactive or constitutive activity, or, alternatively, act to prevent the interferon polypeptide from performing one or more functions. For example, a truncated form lacking one or more domains may have a dominant negative effect. Another aspect of the invention may relate to polypeptides derived from a full-length interferon polypeptide. Isolated peptidyl portions of the subject proteins may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, any one of the subject proteins may be arbitrarily divided into fragments of desired length with no overlap of the fragments, or preferably divided into overlapping fragments of a desired length. The fragments may be produced (recombinantly or by chemical synthesis) and tested to identify those peptidyl fragments which may function as either agonists or antagonists of an interferon polypeptide.

It may also be possible to modify the structure of the subject interferon polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the interferon polypeptides described in more detail herein. Such modified polypeptides may be produced, for instance, by amino acid substitution, deletion, or addition. For instance, it is reasonable to expect that an isolated replacement of a leucine with an isoleucine or valine, an aspartate with a glutamate, a threonine with a serine, cysteine with a serine, or a similar replacement of an amino acid with a structurally related amino acid (i.e. conservative mutations) may not have a major effect on the biological activity of the resulting molecule. Conservative replacements are those that take place within a family of amino acids that may be related in their side chains. Genetically encoded amino acids may be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of an interferon polypeptides can be assessed, e.g., for their ability to modulate viral infection of proliferation, as described in the examples, for their ability to bind to another polypeptide, e.g., another interferon polypeptide.

Polypeptides in which more than one replacement may have taken place may readily be tested in the same manner. This invention further contemplates a method of generating sets of combinatorial mutants of the interferon polypeptides, as well as truncation mutants, and may be especially useful for identifying potential variant sequences (e.g. homologs) that may be functional in binding to an interferon receptor. The purpose of screening such combinatorial libraries may be to generate, for example, interferon homologs which may act as either agonists or antagonist, or alternatively, which possess novel activities all together. Combinatorially-derived homologs may be generated which have a selective potency relative to a naturally occurring interferon polypeptide. Such proteins, when expressed from recombinant DNA constructs, may be used in gene therapy protocols.

Likewise, mutagenesis may give rise to variants which have intracellular half-lives dramatically different than the corresponding wild-type protein. For example, the altered protein may be rendered either more stable or less stable to proteolytic degradation or other cellular process which result in destruction of, or otherwise inactivation of the interferon polypeptide of interest. Such variants, and the genes which encode them, may be utilized to alter interferon levels by modulating the half-life of the protein. For instance, a short half-life may give rise to more transient biological effects and, when part of an inducible expression system, may allow tighter control of recombinant interferon production within the cell. As above, such proteins, and particularly their recombinant nucleic acid constructs, may be used in gene therapy protocols.

In similar fashion, interferon homologs may be generated by the present combinatorial approach to act as antagonists, in that they are able to interfere with the ability of the corresponding wild-type protein to function. In a representative embodiment of this method, the amino acid sequences for a population of interferon homologs may be aligned, preferably to promote the highest homology possible. Such a population of variants may include, for example, homologs from one or more species, or homologs from the same species but which differ due to mutation. Amino acids which appear at each position of the aligned sequences may be selected to create a degenerate set of combinatorial sequences. In a preferred embodiment, the combinatorial library may be produced by way of a degenerate library of genes encoding a library of polypeptides which each include at least a portion of potential interferon sequences. For example, a mixture of synthetic oligonucleotides may be enzymatically ligated into gene sequences such that the degenerate set of potential interferon nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate gene for expression. The purpose of a degenerate set of genes may be to provide, in one mixture, all of the sequences encoding the desired set of potential interferon sequences. The synthesis of degenerate oligonucleotides is well known in the art (see for example, Narang, S A *Tetrahedron* 39, 3, 1983; Itakura et al. (1981) Recombinant DNA, Proc. 3rd Cleveland Sympos. Macromolecules, ed. A G Walton, Amsterdam: Elsevier pp. 273-289; Itakura et al. *Annu. Rev. Biochem.* 53, 323, 1984; Itakura et al. *Science* 198, 1056, 1984; Ike et al. *Nucleic Acids Res.* 11, 477, 1983). Such techniques have been employed in the directed evolution of other proteins (see, for example, Scott et al. *Science* 249, 386-390, 1990; Roberts et al. *Proc. Natl. Acad. Sci. USA* 89, 2429-2433, 1992; Devlin et al. *Science* 249, 404-406, 1990; Cwirla et al. *Proc. Natl. Acad. Sci. USA* 87, 6378-6382, 1990; as well as U.S. Pat. Nos. 5,223,409, 5,198,346, and 5,096,815).

Alternatively, other forms of mutagenesis may be utilized to generate a combinatorial library. For example, interferon variants (both agonist and antagonist forms) may be generated and isolated from a library by screening using, for example, alanine scanning mutagenesis and the like (Rufet al. *Biochemistry* 33, 1565-1572, 1994; Wang et al. *J. Biol. Chem.* 269, 3095-3099, 1994; Balint et al. *Gene* 137, 109-118, 1993; Grodberg et al. *Eur. J. Biochem.* 218, 597-601; 1993; Nagashima et al. *J. Biol. Chem.* 268, 2888-2892, 1993; Lowman et al. *Biochemistry* 30, 10832-10838, 1991; and Cunningham et al. *Science* 244, 1081-1085, 1989), by linker scanning mutagenesis (Gustin et al., *Virology* 193, 653-660, 1993; Brown et al. *Mol. Cell Biol.* 12, 2644-2652, 1992; McKnight et al. *Science* 232, 316, 1982); by saturation mutagenesis (Meyers et al. *Science* 232, 613, 1986); by PCR mutagenesis (Leung et al. *Method Cell Mol. Biol.* 1, 11-19, 1989); or by random mutagenesis, including chemical mutagenesis, etc. (Miller et al. (1992) A Short Course in Bacterial Genetics, CSHL Press, Cold Spring Harbor, N.Y.; and Greener et al. *Strategies in Mol. Biol.* 7, 32-34, 1994). Linker scanning mutagenesis, particularly in a combinatorial setting, may be an attractive method for identifying truncated (bioactive) forms of interferon polypeptides or receptors.

A wide range of techniques are known in the art for screening gene products of combinatorial libraries made by point mutations and truncations, and, for that matter, for screening cDNA libraries for gene products having a certain property. Such techniques may be generally adaptable for rapid screening of the gene libraries generated by the combinatorial mutagenesis of interferon variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high throughput analysis as necessary to screen large numbers of degenerate sequences created by combinatorial mutagenesis techniques.

In an illustrative embodiment of a screening assay, candidate combinatorial gene products of one of the subject proteins may be displayed on the surface of a cell or virus, and the ability of particular cells or viral particles to bind an interferon polypeptide is detected in a "panning assay". For instance, a library of interferon variants may be cloned into the gene for a surface membrane protein of a bacterial cell (Ladner et al., WO 88/06630; Fuchs et al. *Bio/Technology* 9, 1370-1371, 1991; and Goward et al. *Trends Biochem. Sci.* 18, 136-140, 1992), and the resulting fusion protein detected by panning, e.g. using a fluorescently labeled molecule which binds the interferon polypeptide, to score for potentially functional homologs. Cells may be visually inspected and separated under a fluorescence microscope, or, where the morphology of the cell permits, separated by a fluorescence-activated cell sorter.

In similar fashion, the gene library may be expressed as a fusion protein on the surface of a viral particle. For instance, in the filamentous phage system, foreign peptide sequences may be expressed on the surface of infectious phage, thereby conferring two significant benefits. First, because phage may be applied to affinity matrices at very high concentrations, a large number of phage may be screened at one time. Second, since each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVIII coat proteins may be used to generate fusion proteins without disrupting the ultimate packaging of the viral particle (Ladner et al., PCT publication WO 90/02909; Garrard et al., PCT publication WO 92/09690; Marks et al. *J. Biol. Chem.* 267, 16007-16010. 1992; Griffiths et al. *EMBO J.* 12, 725-734, 1993; Clackson et al. *Nature* 352, 624-628, 1991; Barbas et al. *Proc. Natl. Acad. Sci. USA* 89, 4457-4461, 1992).

In certain embodiments, the invention may also provide for reduction of the subject interferon polypeptide to generate mimetics, e.g. peptide or non-peptide agents, which may be able to mimic binding of the authentic protein to another cellular partner. Such mutagenic techniques as described above, as well as the thioredoxin system, may also be particularly useful for mapping the determinants of an interferon polypeptides which participate in protein-protein interactions involved in, for example, binding to their respective receptors. To illustrate, the critical residues of an interferon polypeptide which may be involved in binding to its receptor may be determined and used to generate interferon peptidomimetics which bind to the receptor, and by inhibiting interferon binding, act to inhibit its biological activity. By employing, for example, scanning mutagenesis to map the amino acid residues of an interferon polypeptide which may be involved in binding to the receptor, peptidomimetic compounds may be generated which mimic those residues involved in binding. For instance, non-hydrolyzable peptide analogs of such residues may be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al. *J. Med. Chem.* 29, 295, 1986; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al. *J. Chem. Soc., Perkin Trans.* 1 1231, 1986), and b-aminoalcohols (Gordon et al. *Biochem. Biophys. Res. Commun.* 126, 419, 1985; and Dann et al. *Biochem. Biophys. Res. Commun.* 134, 71, 1986).

The subject polypeptides may further comprise post-translational or non-amino acid elements, such as hydrophobic modifications (e.g. polyethylene glycols or lipids), poly- or mono-saccharide modifications, phosphates, acetylations, etc. Effects of such elements on the functionality of an interferon polypeptide may be tested as described herein for other polypeptide variants.

Covalent modifications of IFNs may be included within the scope of this invention. One type of covalent modification includes reacting targeted amino acid residues of the IFN polypeptide with an organic derivatizing agent that may be capable of reacting with selected side chains or the N- or C-terminal residues of IFN. Derivatization with bifunctional agents may be useful, for instance, for crosslinking IFN to a water-insoluble support matrix or surface for use in the method for purifying anti-IFN antibodies, and vice-versa. Commonly used crosslinking agents include e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the IFN polypeptide included within the scope of this invention may comprise altering the native glycosylation pattern of the polypeptide. "Altering the native glycosylation pattern" is intended for purposes herein to mean deleting one or more carbohydrate moieties found in native sequence IFN, and/or adding one or more glycosylation sites that are not present in the native sequence IFN, and/or altering the nature (profile) of the sugar moieties attached to the polypeptide at various glycosylation sites. Addition of glycosylation sites to the IFN polypeptides may be accomplished by altering the amino acid sequence. The alteration may be made, for example, by the addition of, or substitution by, one or more serine or threonine residues to the native sequence IFN (for O-linked glycosylation sites). The IFN amino acid sequence may optionally be altered through changes at the DNA level, particularly by mutating the DNA encoding the IFN polypeptide at preselected bases such that codons are generated that will translate into the desired amino acids. Another means of increasing the number of carbohydrate moieties on the IFN polypeptide may be by chemical or enzymatic coupling of glycosides to the polypeptide. Such methods are described in the art, e.g., in WO 87/05330, and in Aplin and Wriston, *CRC Crit. Rev. Biochem.* pp. 259-306 (1981).

Removal of carbohydrate moieties present on the IFN polypeptide may be accomplished chemically or enzymatically or by mutational substitution of codons encoding for amino acid residues that serve as targets for glycosylation. Chemical deglycosylation techniques are known in the art and described, for instance, by Hakimuddin et al. *Arch. Biochem. Biophys.* 259, 52 1987; and by Edge et al. *Anal. Biochem.* 118, 131, 1981. Enzymatic cleavage of carbohydrate moieties on polypeptides can be achieved by the use of a variety of endo- and exo-glycosidases as described by Thotakura et al. *Meth. Enzymol.* 138, 350, 1987.

The interferon molecules of the present invention may also be modified in a way to form a chimeric molecule comprising an interferon fused to another heterologous polypeptide or amino acid sequence. Different elements of fusion proteins may be arranged in any manner that may be consistent with the desired functionality. For example, an interferon may be placed C-terminal to a heterologous domain, or, alternatively, a heterologous domain may be placed C-terminal to an interferon. The interferon and the heterologous domain need not be adjacent in a fusion protein, and additional domains or amino acid sequences may be included C- or N-terminal to either domain or between the domains.

In an embodiment, such a chimeric molecule may comprise a fusion of the IFN with a tag polypeptide which provides an epitope to which an anti-tag antibody can selectively bind. The epitope tag may generally be placed at the amino- or carboxyl-terminus of the IFN. The presence of such epitope-tagged forms of the IFN may be detected using an antibody against the tag polypeptide. Also, provision of the epitope tag enables the IFN to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al. *Mol. Cell. Biol.* 8, 2159-2165, 1988); the c-myc tag and the 8F9, 3C7, 6E10, G4, B7 and 9E10 antibodies thereto (Evan et al. *Mol, Cell. Biol.* 5, 3610-3616, 1985); and the Herpes Simplex virus glycoprotein D (gD) tag and its antibody (Paborsky et al. *Protein Eng.* 3, 547-553, 1990). Other tag polypeptides include the Flag-peptide Hopp et al. *BioTechnology* 6, 1204-1210, 1988); the KT3 epitope peptide (Martin et al. *Science* 255, 192-194, 1992); an α-tubulin epitope peptide (Skinner et al. *J. Biol. Chem.* 266, 15163-15166, 1991); and the T7 gene 10 protein peptide tag (Lutz-Freyermuth et al. *Proc. Natl. Acad. Sci. USA* 87, 6393-6397, 1990). Techniques for making fusion genes are well known. Essentially, the joining of various DNA fragments coding for different polypeptide sequences may be performed in accordance with conventional techniques, employing blunt-ended or staggered-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The invention further provides chimeric proteins generated from an interferon polypeptide and a second interferon polypeptide. Such chimeric interferons may contain, for example, an N-terminal portion of one interferon polypeptide and a C-terminal polypeptide from another interferon polypeptide, such as an IFN-α, β, etc. In one embodiment, the hybrid interferon may comprise two or more segments of an interferon. U.S. Pat. No. 6,174,996 illustrates how hybrid interferons may be generated.

In another embodiment, the chimeric molecule may comprise a fusion of the IFN with an immunoglobulin or a particular region of an immunoglobulin. An immunoglobulin element may be any portion of an immunoglobulin. In certain embodiments, the immunoglobulin element comprises one or more domains of an IgG heavy chain. For example, an immunoglobulin element may comprise a heavy chain or a portion thereof from an IgG, IgD, IgA or IgM. Immunoglobulin heavy chain constant region domains include CH1, CH2, CH3, and CH4 of any class of immunoglobulin heavy chain including gamma, alpha, epsilon, mu, and delta classes. Immunoglobulin variable regions include VH, Vkappa, or Vgamma. An Fc portion is a commonly used immunoglobulin element.

For a bivalent form of the chimeric molecule, such a fusion could be to the Fc region of an IgG molecule, to form an "immunoadhesin". The fusion is preferably to a heavy chain constant region sequence, e.g., a hinge, CH2 and CH3 regions, or the CH1, hinge, CH2 and CH3 regions of an IgG immunoglobulin. Immunoadhesins are expected to have a longer half-life and/or slower clearance than the corresponding IFN polypeptide.

In certain embodiments, the subject polypeptides may be fused to a multimerization domain, such as a dimerization domain. Multimerization domains may be essentially any polypeptide that forms a dimer (or higher order complex, such as a trimer, tetramer, etc.) with another polypeptide. Optionally, the multimerization polypeptide associates with other, identical multimerization polypeptides, thereby forming homomultimers. An IgG Fc element is an example of a dimerizing domain that tends to form homomultimers. Optionally, the multimerizing polypeptide associates with other different multimerizing polypeptides, thereby forming heteromultimers. The Jun leucine zipper domain forms a dimer with the Fos leucine zipper domain, and is therefore an example of a dimerizing domain that tends to form heteromultimers. Multimerizing domains may form both hetero- and homomultimers.

Another type of covalent modification of IFN comprises linking the IFN polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. For example, PEGylated variants are expected to have a longer half-life and/or shorter clearance than the corresponding, non-PEGylated interferon polypeptide. The polyol moiety in the polyol-IFN conjugate according to the present invention may be any water-soluble mono- or bifunctional poly(alkylene oxide) having a linear or branched chain. Typically, the polyol is a poly(alkylene glycol) such as poly(ethylene glycol) (PEG). However, those of skill in the art will recognize that other polyols, such as, for example poly(propylene glycol) and copolymers of polyethylene glycol and polypropylene glycol, may be suitably used. Methods of pegylating interferons are described, in U.S. Patent Publication No. 2006/0029573 (also WO 06/004959). Exemplary formulations for pegylated interferons are described in U.S. Patent Publication No. 2006/0051320. For example, the polyethylene glycol group may be attached to a group selected from the lysine side chains and the N-terminal amino group of the polypeptide Other interferon conjugates may be prepared by coupling an interferon to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used.

Interferons tend to oligomerize when expressed recombinantly. It is believed, that certain oligomeric forms result from two or more interferon molecules becoming irreversibly associated with one another through intermolecular covalent bonding, such as by disulfide linkages. This problem has been observed particularly with respect to leukocyte and fibroblast interferons (see, e.g., U.S. Pat. No. 4,816,566). Accordingly, the invention includes variants of the interferons in which one or more cysteine residues are deleted or substituted by residues of other amino acids which are incapable of disulfide bond formation. Preferred variants substantially retain or mimic the biological activity of the IFN from which they are derived. Modification of Cys-24, Cys-29, Cys-119 and Cys-179 to serine residues in human interferons results in a biologically activity polypeptide with antiproliferative activity and antiviral activity. Accordingly, the invention provides variants of the non-human primate interferon polypeptides set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68, or their mature forms, where at least one cysteine residue may be mutated to another residue, preferably a serine residue. The invention also comprises fragments of at least 20, 30, 40, 50, 60, 70, 80, 90, 100 or 150 residues in length of the polypeptides having sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68, where at least 1, 2, 3, 4, 5, 6, 7, 8, 9 or 10 cysteine residues are mutated to another residue, preferably a serine residue.

In an embodiment, the polypeptide may comprise a modification that increases serum half-life.

V. Variant Interferon Polypeptides

It is anticipated that certain mutant forms (or variants) of the interferon polypeptides of the invention may act as agonist or antagonists. While not wishing to be bound to any particular theory, it is well known that mutant forms of protein signaling factors are capable of binding to the appropriate receptor and yet not capable of activating the receptor. Such mutant proteins act as antagonists by displacing the wild-type proteins and blocking the normal receptor activation. Additionally, it is well known that one or more amino acid substitutions may be made in many proteins in order to enhance their activity in comparison to wild-type forms of the protein. Such agonists may have, for example, increased half-life, binding affinity, or activity in comparison to the wild-type protein. There are many well known methods for obtaining mutants (or variants) with a desired activity.

Methods for generating large pools of mutant/variant proteins are well known in the art. In an embodiment, the invention contemplates using interferon polypeptides generated by combinatorial mutagenesis. Such methods, as are known in the art, are convenient for generating both point and truncation mutants, and can be especially useful for identifying potential variant sequences (e.g., homologs) that are functional in a given assay. The purpose of screening such combinatorial libraries is to generate, for example, interferon variants homologs that can act as either agonists or antagonists. Thus, combinatorially derived variants can be generated to have an increased potency relative to a naturally occurring form of the protein. Likewise, interferon variants can be generated by the present combinatorial approach to act as antagonists, in that they are able to mimic, for example, binding to other extracellular matrix components (such as receptors), yet not induce any biological response, thereby inhibiting the action of interferon polypeptides or interferon agonists. Moreover, manipulation of certain domains of interferon by the present method can provide domains more suitable for use in fusion proteins, for example, domains demonstrated to have specific useful properties.

To further illustrate the state of the art of combinatorial mutagenesis, it is noted that the review article of Gallop et al. *J. Med. Chem.* 37, 1233, 1994, describes, the general state of the art of combinatorial libraries as of the earlier 1990's. In particular, Gallop et al state on page 1239"[s]creening the analog libraries aids in determining the minimum size of the active sequence and in identifying those residues critical for binding and intolerant of substitution." In addition, Ladner et al. (PCT Publication No. WO 90/02809), Goeddel et al. (U.S. Pat. No. 5,223,408), and Markland et al. (PCT Publication No. WO 92/15679) illustrate specific techniques which one skilled in the art could utilize to generate libraries of variants which can be rapidly screened to identify variants/fragments which possess a particular activity. These techniques are exemplary of the art and demonstrate that large libraries of related variants/truncants can be readily generated and assayed to isolate particular variants. Gustin et al. *Virology* 193, 653, 1993, and Bass et al. *Proteins: Structure, Function and Genetics* 8, 309-314, 1990, also describe other exemplary techniques from the art which can be adapted as a means for generating mutagenic variants of the interferon polypeptides of the invention.

Indeed, it is plain from the combinatorial mutagenesis art that large scale mutagenesis of interferon proteins, without any preconceived ideas of which residues were critical to the biological function, can generate wide arrays of variants having equivalent biological activity. Alternatively, such methods can be used to generate a wide array of variants having enhanced activity or antagonistic activity. Indeed, it is the ability of combinatorial techniques to screen billions of different variants by high throughout analysis that removes any requirement of a priori understanding or knowledge of critical residues.

VI. Cell Lines and Production of Polypeptides

This invention also pertains to a host cell transfected with a recombinant gene including a coding sequence for one or more of the subject interferon polypeptides or receptors. The host cell may be any prokaryotic or eukaryotic cell. The host cell may be selected from the group consisting of *E. coli, B. subtilis,* a yeast cell, an insect cell, a mammalian cell, a bacterium, a fungal cell, an avian cell, a plant cell, a myeloma cell, a fibroblast 3T3 cell, a COS cell, a Chinese hamster ovary (CHO) cell, a mink-lung epithelial cell, a human foreskin fibroblast cell, a human glioblastoma cell, a teratocarcinoma cell, and the like. For example, a polypeptide of the present invention may be expressed in bacterial cells such as *E. coli,* insect cells (e.g., using a baculovirus expression system), yeast, or mammalian cells. Other suitable host cells are known to those skilled in the art.

Accordingly, the present invention further pertains to methods of producing the subject interferon polypeptides and receptors. For example, a host cell transfected with an expression vector encoding an interferon polypeptide may be cultured under appropriate conditions to allow expression of the polypeptide to occur. In the cases of the interferon polypeptide, the polypeptide may be secreted and isolated from a mixture of cells and medium containing the polypeptide. Alternatively, the polypeptide may be retained in the cytoplasm or in a membrane fraction and the cells harvested, lysed and the protein isolated. A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the interferon polypeptide may be a fusion protein containing a domain which facilitates its purification, such as a GST fusion protein, intein fusion protein, cellulose binding domain fusion protein, polyhistidine fusion protein, and the like. A nucleotide sequence encoding an interferon polypeptide may be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures.

A recombinant nucleic acid of the invention may be produced by ligating the cloned gene, or a portion thereof, into a vector suitable for expression in either prokaryotic cells, eukaryotic cells, or both. Expression vehicles for production of a recombinant interferon polypeptide include plasmids and other vectors. For instance, suitable vectors for the expression of an interferon polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) may be used for transient expression of proteins in eukaryotic cells. For example, a process of producing an expression vector may comprise constructing a first DNA sequence coding for a polypeptide of the invention and operably linking said first DNA sequence with a second DNA sequence which controls expression of said first DNA sequence.

Examples of other viral (including retroviral) expression systems may be found below in the description of gene therapy delivery systems. The various methods employed in the preparation of the plasmids and transformation of host organisms are well known in the art. For other suitable expression systems for both prokaryotic and eukaryotic cells as well as general recombinant procedures, see *Molecular Cloning: A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant interferon polypeptide by use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

It is well known in the art that a methionine at the N-terminal position may be enzymatically cleaved by the use of the enzyme methionine aminopeptidase (MAP). MAP has been cloned from *E. coli* (Ben-Bassat et al. *J. Bacteriol.* 169, 751-757, 1987) and *Salmonella typhimurium* and its in vitro activity has been demonstrated on recombinant proteins (Miller et al. *Proc. Natl. Acad. Sci. USA* 84, 2718-1722, 1987). Therefore, removal of an N-terminal methionine, if desired, may be achieved either in vivo by expressing such recombinant polypeptides in a host which produces MAP (e.g., *E. coli,* CM89 or *S. cerevisiae*), or in vitro by use of purified MAP (e.g., procedure of Miller et al.).

Alternatively, the coding sequences for the polypeptide may be incorporated as a part of a fusion gene including a nucleotide sequence encoding a different polypeptide. This type of expression system may be useful under conditions where it is desirable, e.g., to produce an immunogenic fragment of an interferon polypeptide. For example, the VP6 capsid protein of rotavirus may be used as an immunologic carrier protein for portions of polypeptide, either in the monomeric form or in the form of a viral particle. The nucleic acid sequences corresponding to the portion of the interferon polypeptide to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of an interferon polypeptide and the poliovirus capsid protein may be created to enhance immunogenicity (see, for example, EP Publication No. 0259149; and Evans et al. *Nature* 339, 385, 1989; Huang et al. *J. Virol.* 62, 3855, 1988; and Schlienger et al. *J. Virol.* 66, 2, 1992).

The Multiple Antigen Peptide system for peptide-based immunization may be utilized, wherein a desired portion of an interferon polypeptide may be obtained directly from organo-chemical synthesis of the peptide onto an oligomeric branching lysine core (see, for example, Posnett et al. *J. Biol. Chem.* 263, 1719, 1988; and Nardelli et al. *J. Immunol.* 148, 914, 1992). Antigenic determinants of an interferon polypeptide may also be expressed and presented by bacterial cells.

In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{+2}$ metal resin. The purification leader sequence may then be subsequently removed by treatment with enterokinase to provide the purified interferon polypeptide (see, e.g., Hochuli et al. *J. Chromatogr.* 411, 177, 1987; and Janknecht et al. *Proc. Natl. Acad. Sci. USA* 88, 8972, 1991).

Forms of interferon may be recovered from culture medium or from host cell lysates. It may be desired to purify the interferon from recombinant cell proteins or polypeptides. The following procedures are exemplary of suitable purification procedures: by fractionation on an ion-exchange column; ethanol precipitation, reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the interferon. Various methods of protein purification may be employed and such methods are known in the art and described for example in Deutscher *Methods Enzymol.,* 182, 779-80, 1990; Scopes, Protein Purification: Principles and Practice, Springer-Verlag, New York (1982). The purification step(s) selected will depend, for example, on the nature of the production process used and the particular IFN produced.

In an embodiment, the isolated polypeptide may demonstrate activity of at least $1\times10^7$ u/mg in cytopathic effect assays in either LLC-MK2 cells using vesicular stomatitis virus or A549 cells using encephalomyocarditis virus. The polypeptide may be expressed in microbial cells, eukaryotic cells, mammalian cells, insect cells, yeast cells, and the like.

VII. Antibodies and Binding Partners

Another aspect of the invention pertains to an antibody reactive with a subject interferon polypeptide (such as those represented by SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68), preferably antibodies that may be specifically reactive with said proteins. In a related aspect, the methods or kits of the invention utilize antibodies raised against and/or specific for any of the subject interferon polypeptides (such as those represented by SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68). For example, by using immunogens derived from an interferon polypeptide, anti-protein/anti-peptide antisera or monoclonal antibodies may be made by standard protocols (See, for example, Antibodies: A Laboratory Manual ed. by Harlow and Lane (Cold Spring Harbor Press: 1988)). A mammal, such as a mouse, a hamster or rabbit may be immunized with an immunogenic form of the peptide (e.g., an interferon polypeptide, or an antigenic fragment which may be capable of eliciting an antibody response, or a fusion protein). Techniques for conferring immunogenicity on a protein or peptide include conjugation to carriers or other techniques well known in the art. An immunogenic portion of an interferon polypeptide may be administered in the presence of adjuvant. The progress of immunization may be monitored by detection of antibody titers in plasma or serum. Standard ELISA or other immunoassays may be used with the immunogen as antigen to assess the levels of antibodies. In an embodiment, the subject antibodies are immunospecific for antigenic determinants of an interferon polypeptide of a mammal, e.g., antigenic determinants of a protein set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68. In an embodiment, antibodies may be specific for an interferon protein having the amino acid sequence as set forth in any of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68.

Following immunization of an animal with an antigenic preparation of an interferon polypeptide, anti-interferon antisera may be obtained and, if desired, polyclonal anti-interferon antibodies may be isolated from the serum. To produce monoclonal antibodies, antibody-producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein Nature 256, 495-497, 1975), the human B cell hybridoma technique (Kozbar et al. Immunol. Today 4, 72, 1983), and the EBV-hybridoma technique to produce human monoclonal antibodies (Cole et al. (1985) Monoclonal Antibodies and Cancer Therapy, Alan R. Liss, Inc. pp. 77-96). Hybridoma cells may be screened immunochemically for production of antibodies specifically reactive with a mammalian interferon polypeptide of the present invention and monoclonal antibodies isolated from a culture comprising such hybridoma cells.

The term antibody as used herein is intended to include fragments thereof which may also be specifically reactive with one of the subject interferon polypeptides. Antibodies may be fragmented using conventional techniques and the fragments screened for utility in the same manner as described above for whole antibodies. For example, $F(ab)_2$ fragments may be generated by treating antibody with pepsin. The resulting $F(ab)_2$ fragment may be treated to reduce disulfide bridges to produce Fab fragments. The antibody of the present invention is further intended to include bispecific, single-chain, and chimeric and humanized molecules having affinity for an interferon polypeptide conferred by at least one CDR region of the antibody. In preferred embodiments, the antibody further comprises a label attached thereto and may be able to be detected, (e.g., the label can be a radioisotope, fluorescent compound, enzyme or enzyme co-factor).

In certain preferred embodiments, an antibody of the invention may be a monoclonal antibody, and in certain embodiments the invention makes available methods for generating novel antibodies. For example, a method for generating a monoclonal antibody that binds specifically to an interferon polypeptide may comprise administering to a mouse an amount of an immunogenic composition comprising the interferon polypeptide effective to stimulate a detectable immune response, obtaining antibody-producing cells (e.g. cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the interferon polypeptide, receptor, or fragments thereof. Once obtained, a hybridoma may be propagated in a cell culture, optionally in culture conditions where the hybridoma-derived cells produce the monoclonal antibody that binds specifically to the interferon polypeptide, receptor, or fragments thereof. The monoclonal antibody may be purified from the cell culture.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g. by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, BIAcore AB, Uppsala, Sweden), sandwich assays (e.g. the paramagnetic bead system of IGEN International, Inc., Gaithersburg, Md.), western blots, immunoprecipitation assays and immunohistochemistry. In an embodiment, the antibody or fragment thereof may be selected by immunoselection or immunodepletion.

Another application of anti-interferon antibodies of the present invention may be in the immunological screening of cDNA libraries constructed in expression vectors such as gt11, gt18-23, ZAP, and ORF8. Messenger libraries of this type, having coding sequences inserted in the correct reading frame and orientation, may produce fusion proteins. For instance, gt11 will produce fusion proteins whose amino termini consist of β-galactosidase amino acid sequences and whose carboxy termini consist of a foreign polypeptide. Antigenic epitopes of an interferon polypeptide, e.g., other orthologs of a particular protein or other paralogs from the same species, may then be detected with antibodies, as, for example, reacting nitrocellulose filters lifted from infected plates with the appropriate anti-interferon antibodies. Positive phage detected by this assay may then be isolated from the infected plate. Thus, the presence of interferon homologs may be detected and cloned from other animals, as can alternate isoforms (including splice variants) from humans.

The antibodies described herein may be used to assay the levels of the interferon receptors and polypeptides described herein and in particular for detecting the presence of an interferon polypeptide on a biological sample. The level of interferon polypeptide may be measured in a variety of sample types such as, for example, in cells, stools, and/or in bodily fluid, such as in whole blood samples, blood serum, blood plasma and urine. An antibody specifically reactive with the interleukin of IFN may be preferable. The adjective "specifically reactive with" as used in reference to an antibody is intended to mean, as is generally understood in the art, that the antibody may be sufficiently selective between the antigen of interest (e.g. an interferon polypeptide) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that may be effective at selectively identifying an antigen of interest in one type of biological sample (e.g. a stool sample) may not be as effective for selectively identifying the same antigen in a different type of biological sample (e.g. a blood sample). Likewise, an antibody that may be effective at identifying an antigen of interest in a purified protein preparation that is devoid of other biological contaminants may not be as effective at identifying an antigen of interest in a crude biological sample, such as a blood or urine sample. Accordingly, in preferred embodiments, the method employs antibodies that have demonstrated specificity for an antigen of interest in a sample type that may likely be the sample type of choice for use of the antibody. In a particularly preferred embodiment, the method uses antibodies that bind specifically to an interferon polypeptide in a protein preparation from blood (optionally serum or plasma) from a subject.

Another aspect of the invention features protein or modified protein binding partners to the interferons polypeptides of the subject invention. These protein binding partners feature a peptide or polypeptide epitope which may also be specifically reactive toward interferon epitopes. The complementary polypeptide epitopes may be identified as fragments of antibody protein or through phage display technology. These (poly)peptide sequences may be genetically engineered using conventional techniques into any of several binding partner scaffolds. Alternatively, peptide sequences may be inserted into any of several peptide or organic scaffolds. Thus, this aspect of the invention includes segments of proteolytically-cleaved or recombinantly-prepared portions of an antibody molecule that are capable of selectively reacting with a certain protein that are then inserted into i) an alternative protein backbone, ii) an organic chemical scaffold, and/or iii) a peptide backbone. Non-limiting examples of such backbones or scaffolds are fibronectins, transferring, anticalins, lipocalins, phylomers, CycloTriVeratrylene, TriAzaCyclophane, Shark New Antigen Receptor, and/or peptide aptamers.

In an aspect of the invention, the antibody may be a polyclonal antibody or an antigen-binding fragment thereof. The antibody or antibody fragment may inhibit binding of the polypeptide to its receptor. The antibody or antibody fragment may be a neutralizing antibody or exhibits neutralizing activity. The antibody or antigen-binding fragment thereof may be a humanized antibody, single chain antibody, Fv fragment, scFv, scFv dimer, Nanobody™, Fab fragment, Fab' fragment, or F(ab')2 fragment.

VIII. Antibodies as Antagonists

Certain antibodies may act as interferon antagonists. Antibodies may have extraordinary affinity and specificity for particular epitopes. The binding of an antibody to its epitope on a protein may antagonize the function of that protein by competitively or non-competitively inhibiting the interaction of that protein with other proteins necessary for proper function.

Antibodies with interferon antagonist activity may be identified in much the same way as other interferon antagonists. For example, candidate antibodies may be administered to cells expressing a reporter gene, and antibodies that cause decreased reporter gene expression may be antagonists.

In one variation, antibodies of the invention may be single chain antibodies (scFv), comprising variable antigen binding domains linked by a polypeptide linker. Single chain antibodies may be expressed as a single polypeptide chain and can be expressed in bacteria and as part of a phage display library. In this way, phage that express the appropriate scFv will have interferon antagonist activity. The nucleic acid encoding the single chain antibody may then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

IX. Transgenic Animals

Another aspect of the invention may feature transgenic non-human animals which express a heterologous interferon gene. In another aspect the invention may feature transgenic non-human animals which have had one or both copies of the endogenous interferon genes disrupted in at least one of the tissue or cell-types of the animal. In one embodiment, the transgenic non-human animal may be a mammal such as a mouse, rat, rabbit, goat, sheep, dog, cat, cow, or non-human primate. In certain embodiments, such a transgenic animal may display a phenotype associated with inadequate or excessive cell proliferation or viral infection, and may therefore serve as a useful animal model to study the progression of diseases caused by such inadequate or excessive processes. In one embodiment, the interferon transgenic animals of the present invention may be used for in vivo assays to identify anti-cancer or anti-viral therapeutics.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc. Preferably, the transgenic-animals are mice. Transgenic animals comprise an exogenous nucleic acid sequence present as an extrachromosomal element or stably integrated in all or a portion of its cells, especially in germ cells. Unless otherwise indicated, it may be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene may be usually either from a different species than the animal host, or may be otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In one aspect of the invention, an interferon transgene may encode the wild-type form of the protein, homologs thereof, as well as antisense constructs. An interferon transgene may also encode a soluble form of the protein that has immunomodulatory, antiviral and/or antiproliferative activity. It may be desirable to express the heterologous IFN transgene conditionally such that either the timing or the level of IFN gene expression may be regulated. Such conditional expression may be provided using prokaryotic promoter sequences which require prokaryotic proteins to be simultaneously expressed in order to facilitate expression of the IFN transgene. Exemplary promoters and the corresponding trans-activating prokaryotic proteins are given in U.S. Pat. No. 4,833,080.

Moreover, transgenic animals exhibiting tissue specific expression may be generated, for example, by inserting a tissue specific regulatory element, such as an enhancer, into the transgene. For example, the endogenous interferon gene promoter or a portion thereof may be replaced with another promoter and/or enhancer, e.g., a CMV or a Moloney murine leukemia virus (MLV) promoter and/or enhancer.

Transgenic animals containing an inducible IFN transgene may be generated using inducible regulatory elements (e.g. metallothionein promoter), which are well-known in the art. IFN transgene expression may then be initiated in these animals by administering to the animal a compound which induces gene expression (e.g. heavy metals). Another preferred inducible system comprises a tetracycline-inducible transcriptional activator (U.S. Pat. Nos. 5,654,168 and 5,650,298).

The present invention provides for transgenic animals that carry the transgene in all their cells, as well as animals that carry the transgene in some, but not all cells, i.e., mosaic animals. The transgene may be integrated as a single transgene or in tandem, e.g., head to head tandems, or head to tail or tail to tail or as multiple copies.

The successful expression of the transgene may be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells containing an interferon transgene, preferentially a human interferon transgene. For example, the animal cell (e.g. somatic cell or germ cell (i.e. egg or sperm)) may be obtained from the transgenic animal. Transgenic somatic cells or cell lines may be used, for example, in drug screening assays. Transgenic germ cells, on the other hand, may be used in generating transgenic progeny, as described below.

Although not necessary to the operability of the invention, the transgenic animals described herein may comprise alterations to endogenous genes in addition to, or alternatively, to the genetic alterations described above. For example, the host animals may be either "knockouts" and/or "knock-ins" for a target gene(s) as is consistent with the goals of the invention (e.g., the host animal's endogenous interferon may be "knocked out"). Knockouts have a partial or complete loss of function in one or both alleles of an endogenous gene of interest. Knock-ins have an introduced transgene with altered genetic sequence and/or function from the endogenous gene. The two may be combined, for example, such that the naturally occurring gene is disabled, and an altered form introduced. For example, it may be desirable to knockout the host animal's endogenous interferon gene, while introducing an exogenous interferon gene (e.g., a human interferon gene).

In a knockout, preferably the target gene expression may be undetectable or insignificant. For example, a knock-out of an interferon gene means that function of the interferon has been substantially decreased so that expression may not be detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences may be ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of APP genes. A functional knock-out may also be achieved by the introduction of an anti-sense construct that blocks expression of the native genes (for example, see Li and Cohen, Cell 85, 319-329, 1996). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or repressor. The use of knock-in technology may be combined with production of exogenous sequences to produce the transgenic animals of the invention.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. *Methods. Enzymo*1.185, 527-537, 1990.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells may be plated onto a feeder layer in an appropriate medium. Cells containing the construct may be detected by employing a selective medium. After sufficient time for colonies to grow, they may be picked and analyzed for the occurrence of homologous recombination or integration of the construct. Those colonies that may be positive may then be used for embryo manipulation and blastocyst injection. Blastocysts may be obtained from 4 to 6 week old superovulated females. The ES cells may be trypsinized, and the modified cells may be injected into the blastocoel of the blastocyst. After injection, the blastocysts may be returned to each uterine horn of pseudopregnant females. Females may then be allowed to go to term and the resulting litters screened for mutant cells having the construct. By providing for a different phenotype of the blastocyst and the ES cells, chimeric progeny may be readily detected.

The chimeric animals may be screened for the presence of the modified gene and males and females having the modification may be mated to produce homozygous progeny. If the gene alterations cause lethality at some point in development, tissues or organs may be maintained as allogeneic or congenic grafts or transplants, or in in vitro culture.

In certain embodiments, the invention further provides methods for identifying (screening) or for determining the safety and/or efficacy of therapeutics, i.e. compounds which may be useful for treating and/or preventing tumors and viral infections. In addition, the assays may be useful for further improving known therapeutic compounds, e.g., by modifying their structure to increase their stability and/or activity and/or toxicity.

X. Methods of Screening

The present invention may also provide screening methods for identifying compounds capable of enhancing or inhibiting a biological activity of an interferon polypeptide. In one embodiment, the method comprises (i) contacting a receptor whose activity may be regulated by an interferon polypeptide with the candidate compound in the presence of an interferon polypeptide, (ii) assaying an activity of the receptor, for example, anti-viral activity, in the presence of the candidate compound and the interferon polypeptide, and (iii) comparing the activity to a standard level of activity, the standard being assayed when contact may be made between the receptor and interferon in the absence of the candidate compound. In this assay, an increase in activity over the standard indicates that the candidate compound may be an agonist of interferon activity and a decrease in activity compared to the standard indicates that the compound may be an antagonist of interferon activity.

The invention provides methods of identifying modulators of interferon activity. In one aspect, the elucidation of the interferon sequence facilitates rational design of interferon agonists and antagonists based on the structural features of the interferon protein, which may be determined using X-ray crystallography, neutron diffraction, nuclear magnetic resonance spectrometry, and other techniques. In addition, the present invention provides assays for identifying therapeutic agents that modulate cell proliferation and viral infection. In certain embodiments, the therapeutic agents either interfere with or promote interferon function. In other embodiments, the therapeutic agents interfere with the interaction between interferon and an interferon receptor. In another embodiment, the therapeutic agents alter the expression level of endogenous interferon expression, by either increasing or decreasing interferon expression. In a further embodiment, the present invention provides assays for identifying therapeutic agents which either interfere with or promote the anti-viral or antiproliferative activity of an interferon polypeptide. In another embodiment, the assay may detect agents which modulate the intrinsic biological activity of any of the subject interferon polypeptides, such as the anti-viral, immunomodulatory or antiproliferative properties, binding to other cellular components, cellular compartmentalization, and the like. Certain embodiments of the invention relate to assays for identifying agents that bind to an interferon polypeptide. In one embodiment, an assay may detect agents which inhibit interaction of one or more subject interferon polypeptides with its receptor. A wide variety of assays may be used for this purpose, including labeled in vitro protein-protein binding assays, electrophoretic mobility shift assays, interaction trap assay, immunoassays for protein binding, and the like.

Given the role of interferon polypeptides in modulating viral infection and cell proliferation, the agents that bind to interferons as well as the agents that interfere with interferons binding to their receptors may be able to modulate viral infection and/or cell proliferation. Accordingly, one aspect of the invention provides a method for assessing the ability of an agent to modulate viral infection and/or cell proliferation, comprising: 1) combining: a first polypeptide including at least a portion of an interferon polypeptide with a cell expressing an interferon receptor, and an agent, under conditions wherein the first polypeptide interacts with the interferon receptor in the absence of said agent, 2) determining if said agent interferes with the interaction, and 3) for an agent that interferes with the interaction, further assessing its ability to interfere with the interferon's antiviral or antiproliferative activity. In preferred embodiments, the interferon may be an interferon or a biologically-active fragment thereof, such as an N-terminal fragment of the mature form.

Other embodiments of the invention include methods for assessing the ability of an agent to modulate viral infection and/or cell proliferation comprising 1) combining a polypeptide including at least a portion of an interferon with an agent under conditions where the polypeptide exhibits antiviral and/or antiproliferative activity in the absence of the agent, and 2) determining if the agent interferes with or promotes the interferon modulation of antiviral and/or antiproliferative activity.

A variety of assay formats will suffice and, in light of the present disclosure, those not expressly described herein will nevertheless be comprehended by one of ordinary skill in the art. Assay formats which approximate such conditions as formation of protein complexes may be generated in many different forms, and include assays based on cell-free systems, e.g. purified proteins or cell lysates, as well as cell-based assays which utilize intact cells. Simple binding assays may also be used to detect agents which bind to the interferons of the present invention. Such binding assays may also identify agents that act by disrupting the interaction between an interferon polypeptide and its receptor. Agents to be tested may be produced, for example, by bacteria, yeast or other organisms (e.g. natural products), produced chemically (e.g. small molecules, including peptidomimetics), or produced recombinantly. In a preferred embodiment, the test agent may be a small organic molecule, e.g., other than a peptide or oligonucleotide, having a molecular weight of less than about 1,000 Daltons. In many drug screening programs which test libraries of compounds and natural extracts, high throughput assays may be desirable in order to maximize the number of compounds surveyed in a given period of time.

In binding assays, the interaction is binding and the complex formed may be isolated or detected in the reaction mixture. In a particular embodiment, a receptor of a polypeptide encoded by one of the interferon/interleukin polypeptides disclosed herein, or the drug candidate, may be immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized may be used to anchor it to a solid surface. The assay may be performed by adding the non-immobilized component, which may be labeled by a detectable label, to the immobilized component, e.g. the coated surface containing the anchored component. When the reaction is complete, the non-reacted components are removed e.g. by washing, and complexes anchored on the solid surface may be detected. When the originally non-immobilized component carries a detectable label, the detection of label immobilized on the surface indicates that complexing occurred. Where the originally non-immobilized component does not carry a label, complexing may be detected, for example, by using a labeled antibody specifically binding the immobilized complex.

A variety of other reagents may be included in the screening assay. These include reagents like salts, neutral proteins, e.g. albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, and the like may be used. The mixture of components may be added in any order that provides for the requisite binding. Incubations may be performed at any suitable temperature, typically between 4° and 40° C. Incubation periods may be selected for optimum activity, but may also be optimized to facilitate rapid high-throughput screening.

In yet another embodiment, the interferon polypeptide and a potential interacting polypeptide may be used to generate an interaction trap assay (see also, U.S. Pat. No. 5,283,317; Zervos et al. *Cell* 72, 223-232, 1993; Madura et al. *J. Biol. Chem.* 268, 12046-12054, 1993; Bartel et al. *Biotechniques* 14, 920-924, 1993; and Iwabuchi et al. *Oncogene* 8, 1693-1696, 1993), for subsequently detecting agents which disrupt binding of the proteins to one and another.

One aspect of the present invention provides reconstituted protein preparations including an interferon polypeptide and one or more interacting polypeptides.

In an aspect of the invention, the polypeptides may serve as activity standards in assays of interferon bioactivity. In an aspect of the invention, the polypeptides may serve as activity standards in assays of anti-interferon neutralizing antibody bioactivity.

In an aspect of the invention, a kit may be used to detect one or more of the polypeptides of the invention. In an aspect of the invention, a kit may be used to differentiate between one or more of the polypeptides of the invention. In an aspect of the invention, a kit may be used to differentiate one or more of the polypeptides of the invention from similar polypeptides.

XI. DNA Microarrays

Another aspect of the invention provides a DNA microarray comprising at least one polynucleotide comprising at least a region of 20, 25, 30, 35, 40, 45, 50, 60 or 70 nucleotides in length that is identical to a portion of any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67.

DNA microarray and methods of analyzing data from microarrays are well-known in the art, including in DNA Microarrays: A Molecular Cloning Manual, Ed by Bowtel and Sambrook (Cold Spring Harbor Laboratory Press, 2002); Microarrays for an Integrative Genomics by Kohana (MIT Press, 2002); A Biologist's Guide to Analysis of DNA Microarray Data, by Knudsen (Wiley, John & Sons, Incorporated, 2002); and DNA Microarrays: A Practical Approach, Vol. 205 by Schema (Oxford University Press, 1999); and Methods of Microarray Data Analysis II, ed by Lin et al. (Kluwer Academic Publishers, 2002), hereby incorporated by reference in their entirety.

In an embodiment, a microarray comprises a support or surface with an ordered array of binding (e.g., hybridization) sites or "probes" each representing one of the markers described herein. Preferably the microarrays are addressable arrays, and more preferably positionally addressable arrays. More specifically, each probe of the array may be preferably located at a known, predetermined position on the solid support such that the identity (i.e., the sequence) of each probe may be determined from its position in the array (i.e., on the support or surface). In preferred embodiments, each probe may be covalently attached to the solid support at a single site.

Microarrays may be prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences may be synthesized either enzymatically in vivo, enzymatically in vitro (e.g., by PCR), or non-enzymatically in vitro.

The probe or probes used in the methods and gene chips of the invention may be immobilized to a solid support which may be either porous or non-porous. For example, the probes of the invention may be polynucleotide sequences which may be attached to a nitrocellulose or nylon membrane or filter covalently at either the 3' or the 5' end of the polynucleotide. Such hybridization probes are well known in the art (see, e.g., Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, the solid support or surface may be a glass or plastic surface. In a particularly preferred embodiment, hybridization levels may be measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

DNA microarrays may be fabricated using drop deposition from pulse-jets of either nucleic acid precursor units (such as monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043. Instead of drop deposition methods, photolithographic array fabrication methods may be used. Inter-feature areas need not be present particularly when the arrays are made by photolithographic methods as described in those patents.

Preferably, microarrays may be made from materials that may be stable under binding (e.g., nucleic acid hybridization) conditions. The microarrays are preferably small, e.g., between 1 $cm^2$ and 25 $cm^2$, between 12 $cm^2$ and 13 $cm^2$, or about 3 $cm^2$. However, larger arrays may also be contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom).

XII. Compositions

In another aspect, the invention further provides compositions comprising any of the interferon/interleukin polynucleotides or interferon/interleukin polypeptides, described herein, for administration to cells in vitro, to cells ex vivo and to cells in vivo, or to a multicellular organism. In certain particularly preferred embodiments of this aspect of the invention, the compositions comprise an interferon polynucleotide for expression of an interferon polypeptide in a host organism for treatment of disease. Particularly preferred in this regard is expression in a human subject for treatment of a dysfunction associated with loss of endogenous activity of an interferon.

Pharmaceutical compositions for use in accordance with the present invention may be formulated in conventional manners using one or more physiologically acceptable carriers or excipients. The therapeutic compositions of the invention may be formulated for a variety of loads of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the therapeutic compositions of the invention may be formulated in liquid solutions, preferably in physiologically compatible buffers such as Hank's solution or Ringer's solution. In addition, the therapeutic compositions may be formulated in solid form and redissolved or suspended immediately prior to use. Lyophilized forms are also included.

For oral administration, the therapeutic compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active agent. For buccal administration the therapeutic compositions may take the form of tablets or lozenges formulated in conventional manner. For administration by inhalation, the compositions for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the therapeutic agents and a suitable powder base such as lactose or starch.

The therapeutic compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the therapeutic compositions may also be formulated as a depot preparation. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration may also be by transmucosal or transdermal means. For transmucosal or transdermal administration, penetrants appropriate to the barrier to be permeated may used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention may be formulated into ointments, salves, gels, or creams as generally known in the art. A wash solution may be used locally to treat an injury or inflammation to accelerate healing. For oral administration, the therapeutic compositions may be formulated into conventional oral administration forms such as capsules, tablets, and tonics.

The therapeutic compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the nucleic acids of the invention may be formulated for a variety of modes of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, intranodal, and subcutaneous for injection, the nucleic acids of the invention may be formulated in liquid solutions, preferably in physiologically compatible buffers such as Hank's solution or Ringer's solution. In addition, the nucleic acids may be formulated in solid form and redissolved or suspended immediately prior to use. Lyophilized forms are also included.

Toxicity and therapeutic efficacy of therapeutic compositions of the present invention may be determined by standard pharmaceutical procedures in cell cultures or experimental animals, e.g., for determining The $LD_{50}$ (The Dose Lethal To 50% Of The Population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents which exhibit large therapeutic indices may be preferred. While therapeutic compositions that exhibit toxic side effects may be used, care should be taken to design a delivery system that targets such therapeutic agents to the site of affected tissue in order to minimize potential damage to uninfected cells and, thereby, reduce side effects.

The data obtained from the cell culture assays and animal studies may be used in formulating a range of dosages for use in humans. The dosage lies preferably within a range of circulating concentrations that include the $ED_{50}$ with little or no toxicity. The dosage may vary within this range depending upon the dosage form employed and the route of administration utilized. For any agents used in the method of the invention, the therapeutically effective dose may be estimated initially from cell culture assays. A dose may be formulated in animal models to achieve a circulating plasma concentration range that includes the $IC_{50}$ (i.e., the concentration of the test therapeutic agent which achieves a half-maximal inhibition of symptoms) as determined in cell culture. Such information may be used to more accurately determine useful doses in humans. Levels in plasma may be measured, for example, by high performance liquid chromatography.

In one embodiment, the compositions may be formulated for oral administration. U.S. Pat. No. 5,846,526 describes the oral interferon compositions that may be adapted for the interferon polypeptides described herein.

Another aspect of the invention provides an article of manufacture containing materials useful for the diagnosis or treatment of the disorders described below is provided. The article of manufacture comprises a container and a label. Suitable containers include, for example, bottles, vials, syringes, and test tubes. The containers may be formed from a variety of materials such as glass or plastic. The container may hold a composition which may be effective for diagnosing or treating the condition and may have a sterile access port (for example the container may be an intravenous solution bag or a vial having a stopper pierceable by a hypodermic injection needle). The active agent in the composition may be an interferon of the present invention, preferably an interferon polypeptide, or an agonist or antagonist thereof. The label on, or associated with, the container may indicate that the composition may be used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

In another aspect, the subject interferon may be coformulated with another interferon. Accordingly, in an embodiment, the compositions of interferon polypeptides of any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68 further comprise an interferon alpha (IFN-α), an interferon beta (IFN-β), or an interferon gamma (IFN-γ). In an embodiment, the composition comprises IFN-α2a. In another embodiment, the composition of an interferon further comprises an interferon selected from IFN-α, IFN-β, IFN-ε, IFN-κ, IFN-τ, or IFN-ω. In an embodiment, the interferon and the second interferon act synergistically in at least one of the assays described herein, such as the anti-viral assays, and anti-proliferation assays and the immunomodulatory assays.

Another aspect of the invention provides a composition comprising (i) an interferon polypeptide having an amino acid sequence that is at least 99%, 99.3%, 99.6% or 100% identical to the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these IFN polypeptides; (ii) a second interferon polypeptide selected from an IFN-α, IFN-β, IFN-ε, IFN-κ, IFN-τ or IFN-ω; and (iii) a pharmaceutically acceptable carrier. In one embodiment, the interferon polypeptide of part (i) is identical to either to full-length or the mature forms of the interferons of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, optionally where at least 1, 2, 3, 4 or 5 cysteine residues are replaced with another residue, preferably a serine residue. In another embodiment, the IFN polypeptides of part (i) is a polypeptide comprising a portion of an amino acid sequence at least 99%, 99.3%, 99.6% or 100% identical to the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these IFN polypeptides, wherein said portion is a functional portion, such as a portion that retains a substantial anti-viral, anti-proliferative, or immunomodulatory activity.

In preferred embodiments, the compositions comprise the full-length forms, mature forms, variants, or cysteine substituted forms, or combinations thereof, of the interferons having the amino acid sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68.

In an embodiment, a composition comprises at least one of the nucleic acids, polypeptides, antibodies, or binding partners of the invention, and a pharmaceutically acceptable excipient. In an embodiment, a composition may comprise a carrier and at least one of the expression vector described herein or a recombinant virus that comprises the expression vector described herein.

XIII. Pharmaceutical Compositions

In another aspect, the present invention provides pharmaceutical preparations comprising interferons, interferon agonists or interferon antagonists. The interferons, interferon agonists and/or interferon antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compositions of the present invention, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "depot formulations."

Pharmaceutical formulations of the present invention may also include veterinary compositions, e.g., pharmaceutical preparations of the compositions of the present invention suitable for veterinary uses, e.g., for the treatment of livestock, non-human primates, domestic animals, (such as dogs and cats) and the like.

Rechargeable or biodegradable devices may also provide methods of introduction. In embodiments, various slow release polymeric devices have been developed and tested in vivo in recent years for the controlled delivery of drugs, including proteinaceous biopharmaceuticals. In embodiments, a variety of biocompatible polymers (including hydrogels), including both biodegradable and non-degradable polymers, can be used to form an implant for sustained release at a particular target site.

External pumps and metering devices may also provide methods of introduction. In embodiments, pumps may provide steady introduction of the interferon into the subject, or may provide pulsatile release, depending on the therapeutic strategy. In addition, if coupled with a method of measuring bioavailable interferon in the subject, the pump or metering device may be tuned to provide exogenous interferon when bioavailable levels fall below a set threshold.

The preparations of the present invention may be given orally, parenterally, topically, intratumorally, rectally, or the like. They are of course given by forms suitable for each administration route. For example, they are administered in tablets or capsule form, by injection, inhalation, eye lotion, ointment, suppository, controlled release patch, etc., administration by injection, infusion or inhalation; topical by lotion or ointment; and rectal by suppositories; and the like. Oral, parenteral, and topical administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally, sublingually, and the like.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which may be effective to achieve the desired therapeutic response for a particular subject, composition, and mode of administration, without being toxic to the subject.

The selected dosage level may depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular composition employed, the age, sex, weight, condition, general health and prior medical history of the subject being treated, and the like.

A physician, veterinarian or other healthcare provider having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms.

The subject receiving this treatment is any animal in need, including primates, in particular humans, and other mammals such as equines, cattle, swine and sheep; and poultry and pets and other organisms in general.

The compound of the invention may be administered as such or in admixtures with pharmaceutically acceptable and/or sterile carriers and can also be administered in conjunction with other agents. Non-limiting examples of such agents include antimicrobial agents such as penicillins, cephalosporins, aminoglycosides, and glycopeptides. Conjunctive therapy thus includes sequential, simultaneous and separate administration of the active compound in a way that the therapeutic effects of the first administered one is not entirely disappeared when the subsequent is administered.

While it is possible for a compound of the present invention to be administered alone, it is preferable to administer the compound as a pharmaceutical formulation (composition). The compositions of the present invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a subject.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agonists from one organ, or portion of the body, to another organ, or portion of the body. Each carrier should be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid, (16) pyrogen-free water; (17) isotonic saline; (18) Ringer's solution; (19) ethyl alcohol; (20) phosphate buffer solutions; and (21) other non-toxic compatible substances employed in pharmaceutical formulations.

XIV. Therapeutic Applications

The novel interferon polypeptides of the present invention have antiviral, antiproliferative and/or immunoregulatory activities. Thus, the interferons, including variants and derivatives of the native protein, may be used for the treatment of malignant or non-malignant conditions associated with unwanted cell proliferation, or viral diseases. More particularly, the interferons may be useful for the treatment of diseases characterized by tumorigenic or neoplastic cell growth, malignant hematological systemic diseases, viral disease, asthma, carcinomas, sarcomas, myelomas, melanomas, lymphomas, papillomas, degenerative diseases, allergic diseases, psoriasis, pain, and the like. The interferons may be useful for immune system related disorders, such as, viral infection, parasitic infection, bacterial infection, cancer, autoimmune disease, multiple sclerosis, lymphoma, allergy, and the like. Dosages may be calculated based upon the specific activity of the interferon as compared to the specific activities of other, known interferons, which have been used to treat similar conditions. In an embodiment, the polypeptide of the invention may inhibit proliferation of a mammalian cell, inhibit viral infection of a mammalian cell, increase expression of MHC Class I and/or MHC Class II molecules on the surface of mammalian cells, stimulate or inhibit interferon production by mammalian cells, or a combination thereof. The mammalian cell may be a non-human primate cell. The mammalian cell may be the LLC-MK2 cell line or the A549 cell line. The viral infection may be caused by one of encephalomyocarditis virus, vesicular stomatitis virus, coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, influenza virus, flavivirus, and the like.

The IFN polypeptides and their agonists may also be used as adjuncts to chemotherapy. It is well understood that chemotherapeutic treatment results in suppression of the immune system. Often, although successful in destroying the tumor cells against which they are directed, chemotherapeutic treatments result in the death of the subject due to such side effects of the chemotherapeutic agents. Administration of the IFN polypeptides or their agonists may prevent this side effect as a result of their ability to upregulate the subject's immune system. In general, subjects suffering from immunosuppression due to any underlying cause, including HIV infection (or AIDS), may benefit from treatment with the IFN polypeptides or agonist thereof.

The invention provides a method of treating a subject afflicted with severe acute respiratory syndrome (SARS), comprising administering to the subject an amount of an interferon polypeptide effective to reduce the concentration of SARS-associated coronavirus particles in the subject, thereby treating the subject.

The invention provides a method of treating a subject infected with a virus selected from the group consisting of coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, flavivirus, and the like, comprising administering to the subject an amount of an interferon polypeptide that may be effective to reduce the concentration of virus particles in the subject, thereby treating the subject.

This invention contemplates any of the treatment methods described herein also as methods for preventing the subject from becoming afflicted or infected, or as methods of reducing the subject's risk of a affliction or infection, or as protecting the subject against disorders/conditions related to a particular virus, or as preventing the subject from exhibiting symptoms associated with a viral infection. For instance, the above methods for treating subject infected with a virus may also be used to prevent the subject from becoming infected with the virus, or to reduce the subject risk of viral infection.

This invention provides a method of reducing a subject's risk of viral infection comprising administering to the subject one of the interferon polypeptides described herein, or biologically active fragments thereof. In one embodiment, this method comprises preventing the subject from being infected with the virus. In one embodiment, this method comprises preventing the subject from exhibiting symptoms associated with a viral infection. In one embodiment, this method comprises protecting the subject against disorders/conditions related to a particular virus. This protection may be conferred by preventing or lessening the severity of a disorder/condition resulting from the infection. In another embodiment, the protection may also be conferred by reducing the spread of infection to others by lessening the severity of a disorder/condition resulting from the infection in the subject. In another embodiment, the prevention or reduction of risk may be effected by causing the subject's cells to become less susceptible to infection. The methods and embodiments described herein are not necessarily mutually exclusive. The viral infections include but are not limited to those caused by coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, flavivirus, and the like.

This invention provides a method of treating a subject afflicted with influenza (orthomyxovirus) comprising administering to the subject an amount of one of the interferon polypeptides described herein, preferably an interferon polypeptide that may be effective to reduce the concentration of influenza virus particles in the subject.

This invention also provides a method of preventing a subject from becoming afflicted with a syndrome caused by a virus selected from the group consisting of coronavirus, smallpox virus, cowpox virus, monkeypox virus, West Nile virus, vaccinia virus, respiratory syncytial virus, rhinovirus, arterivirus, filovirus, picornavirus, reovirus, retrovirus, papovavirus, herpesvirus, poxvirus, hepadnavirus, astrovirus, coxsackie virus, paramyxoviridae, orthomyxoviridae, echovirus, enterovirus, cardiovirus, togavirus, rhabdovirus, bunyavirus, arenavirus, bornavirus, adenovirus, parvovirus, flavivirus, and the like, comprising administering to the subject an amount of an interferon polypeptide described herein, such as an interferon polypeptide.

In an embodiment, the subject interferons may be used as anti-viral agents. Interferons have been used clinically for anti-viral therapy, for example, in the treatment of acquired immune disorders, viral hepatitis including chronic hepatitis B, hepatitis C, hepatitis D, papilloma viruses, herpes, viral encephalitis, and in the prophylaxis of rhinitis and respiratory infections.

In another embodiment, the subject interferon may be used as anti-parasitic agents. The subject interferons may be used, for example, for treating *Cryptosporidium parvum* infection.

In still another embodiment, the subject interferons may be used as anti-bacterial agents. Interferons have been used clinically for anti-bacterial therapy. For example, the subject interferons can be used in the treatment of multidrug-resistant pulmonary tuberculosis.

In yet another embodiment, the subject interferons may be used as anti-cancer agents. Interferon therapy using the subject interferons may be used in the treatment of numerous cancers e.g., hairy cell leukemia, acute myeloid leukemia, osteosarcoma, basal cell carcinoma, glioma, renal cell carcinoma, multiple myeloma, melanoma, Hodgkin's disease, and the like.

In yet another embodiment, the subject interferons may be used as part of an immunotherapy protocol. The interferons of the present invention may be used clinically for immunotherapy or more particularly, for example, to prevent graft vs. host rejection, or to curtail the progression of autoimmune diseases, such as arthritis, multiple sclerosis, or diabetes.

In another embodiment, the subject interferons may be used as part of a program for treating allergies. In still another embodiment, the subject interferons may be used as vaccine adjuvants. The subject interferons may be used as an adjuvant or coadjuvant to enhance or stimulate the immune response in cases of prophylactic or therapeutic vaccination. For example, a vaccine may comprise (i) an antigen; and (ii) the interferon polypeptide of the invention.

In certain embodiments, the invention provides methods of treating disease by administering substantially purified interferon, or interferon agonists or antagonists, or interferon binding agents, or interferon antisera or antisera directed against interferon antisera to a subject.

Additional methods include administration of interferon, interferon fragments, interferon antisera, or interferon receptor agonists and antagonists linked to cytotoxic agents. It is to be understood that the interferon can be animal or human in origin.

The present invention further includes methods of treating disease by altering (including increasing or decreasing) the production and/or activity of interferon. Exemplary methods for inhibiting the production of interferon include: decreasing interferon level by administrating interferon inhibitory nucleic acids such as RNAi constructs, antisense oligonucleotides, ribozyme, and DNA enzymes.

Another method of treating disease may be by blocking the action of excess endogenous interferon. This may be done by passively immunizing a human or animal with antibodies specific for the undesired interferon in the system.

The present invention may also encompass gene therapy whereby the gene encoding a subject interferon may be regulated in a subject. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12, 335-356, 1992, which is hereby incorporated by reference. Gene therapy encompasses incorporation of DNA sequences into somatic cells or germ line cells for use in either ex vivo or in vivo therapy. Gene therapy functions to replace genes, or to augment normal or abnormal gene function.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the subject. It is believed that the liposome/DNA complexes may be concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies may also be described by delivery site. Fundamental ways to deliver genes include ex vivo gene transfer, in vivo gene transfer, and in vitro gene transfer. In ex vivo gene transfer, cells are taken from the subject and grown in cell culture. The DNA is transfected into the cells, and the transfected cells are expanded in number and then reimplanted in the subject. In in vitro gene transfer, the transformed cells are cells grown in culture, such as tissue culture cells, and not particular cells from a particular subject. These "laboratory cells" are transfected, and the transfected cells are selected and expanded for either implantation into a subject or for other uses.

In vivo gene transfer involves introducing the DNA into the cells of the subject when the cells are within the subject. Methods include using virally mediated gene transfer using a noninfectious virus to deliver the gene in the subject or injecting naked DNA into a site in the subject and the DNA is taken up by a percentage of cells in which the gene product protein is expressed. Additionally, the other methods described herein, such as use of a "gene gun," may be used for in vitro insertion of endothelial cell proliferation inhibitor DNA or inhibitor regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex may be transported into the cell. The ligand gene complex may be injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells may then be introduced into the subject to provide the gene product from the inserted DNA.

Viral vectors have also been used to insert genes into cells using in vivo protocols. To direct tissue-specific expression of foreign genes, cis-acting regulatory elements or promoters that are known to be tissue specific may be used. Alternatively, this can be achieved using in situ delivery of DNA or viral vectors to specific anatomical sites in vivo. For example, gene transfer to blood vessels in vivo was achieved by implanting in vitro-transduced endothelial cells in chosen sites on arterial walls. The virus infected surrounding cells which also expressed the gene product. A viral vector may be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex may be conveniently introduced into body fluids or the bloodstream and then site specifically directed to the target organ or tissue in the body. Both liposomes and polycations, such as polylysine, lipofectins or cytofectins, may be used. Liposomes may be developed which are cell specific or organ specific and thus the foreign DNA carried by the liposome will be taken up by target cells. Injection of immunoliposomes that are targeted to a specific receptor on certain cells may be used as a convenient method of inserting the DNA into the cells bearing the receptor. Another carrier system that has been used is the asialoglycoprotein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA may be coupled to carrier nuclear proteins in specifically engineered vesicle complexes and carried directly into the nucleus.

The interferons of the invention may also be given prophylactically to individuals known to be at high risk for developing new or re-current cancers. Accordingly, an aspect of the invention encompasses methods for prophylactic prevention of cancer in a subject, comprising administrating to the subject an effective amount of an interferon polypeptide and/or a derivative thereof.

According to the present invention, interferon may be used in combination with other compositions and procedures for the treatment of diseases. For example, a tumor may be treated conventionally with surgery, radiation, or chemotherapy combined with interferon and then interferon may be subsequently administered to the subject to extend the dormancy of micrometastases and to stabilize any residual primary tumor.

In an embodiment of the therapeutic methods described herein, the interferon may be administered in combination with another interferon. Applicants have discovered a synergistic effect between interferon and an IFN-α. Accordingly, in one embodiment of the methods described herein for the treatment of animals or other individuals by administering an interferon polypeptide, the method further comprises the coadministration of an interferon alpha (IFN-α), an interferon beta (IFN-β), or an interferon gamma (IFN-γ). In another embodiment, the method further comprises the coadministration of an interferon alpha IFN-α, IFN-β, IFN-ε, IFN-κ, IFN-τ, or IFN-ω. In an embodiment, the interferon and the second interferon act synergistically in any of the assays described herein, such as the anti-viral assays, and anti-proliferation assays and the immunomodulatory assays.

In an embodiment of the therapeutic methods described herein, the animal or individual to be treated is administered a composition comprising (i) an interferon polypeptide having an amino acid sequence that is at least 99%, 99.3, 99.6% or 100% identical to the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these IFN polypeptides; (ii) a second interferon polypeptide selected from an IFN-α, IFN-β, IFN-ε, IFN-κ, IFN-τ or IFN-ω; and (iii) a pharmaceutically acceptable carrier. In an embodiment, the interferon polypeptide of part (i) above is identical to either to full-length or the mature forms of the interferons of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, optionally where at least 1, 2, 3, 4 or 5 cysteine residues are replaced with another residue, preferably a serine residue. In another embodiment, the IFN polypeptides of part (i) above is a polypeptide comprising a portion of an amino acid sequence at least 99%, 99.3, 99.6% or 100% identical to the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, or to the mature forms of these IFN polypeptides, wherein said portion is a functional portion, such as a portion that retains a substantial anti-viral, anti-proliferative activity or immunomodulatory activity.

The invention also provides methods of treating an avian viral infection in primates. In an embodiment, the avian viral infection is an influenza infection. In another embodiment, the avian infection may be caused by a virus selected from avian pneumovirus, avian encephalitis virus, avian influenza, avian leukosis, fowl pox, infectious bronchitis virus, infectious bursal disease virus, Newcastle disease virus, reovirus, and the like.

The invention also provides methods of detecting the level of interferon gene products in a sample from an animal, preferably a mammal. In one embodiment of the methods described herein for detecting the level of an interferon gene product, determining a level of an interferon gene product in a sample obtained from a mammal comprises determining the level of interferon mRNA in the sample. The level of interferon mRNA in the sample may be assessed by combining oligonucleotide probes derived from the nucleotide sequence of interferon with a nucleic acid sample from the individual, under conditions suitable for hybridization. Hybridization conditions may be selected such that the probes will hybridize only with the specified gene sequence. In an embodiment, conditions may be selected such that the probes will hybridize only with an altered nucleotide sequences, such as but not limited to, splice isoforms, and not with unaltered nucleotide sequences; that is, the probes may be designed to recognize only particular alterations in the nucleic acid sequence of interferon, including addition of one or more nucleotides, deletion of one or more nucleotides or a change in one or more nucleotides (including substitution of a nucleotide for one which is normally present in the sequence).

Methods of quantifying mRNA in a sample are well-known in the art. In a particular embodiment, oligonucleotide probes specific to interferon may be displayed on an oligonucleotide array or used on a DNA chip, as described in WO 95/11995. The term "microarray" refers to an array of distinct polynucleotides or oligonucleotides synthesized on a substrate, such as paper, nylon or other type of membrane, filter, chip, glass slide, or any other suitable solid support. Microarrays also include protein microarrays, such as protein microarrays spotted with antibodies. Other techniques for detecting interferon mRNA levels in a sample include reverse transcription of mRNA, followed by PCR amplification with primers specific for an interferon mRNA.

One embodiment of the invention comprises the use of complementary nucleic acid sequences to measure allelic variants nucleotide sequences encoding any of the polypeptides of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68, with or without the signal sequence. It will be obvious to one skilled in the art that nucleic acids encoding the proteins of the current invention with altered sequences are possible. These alternative nucleic acid sequences may arise due to engineering of silent mutations or allelic forms of these genes with silent mutations. Such allelic variants have been identified in human interferon alpha genes as single nucleotide polymorphisms (SNP). Such silent mutation may be exemplified by rs2988573 which is an SNP in the human alpha 6 gene where the codon for Asparagine 89 in the precursor protein has T replacing the C. Within the human alpha 17 gene, two silent mutation SNPs, SNP rs10117962 where the codon for Isoleucine 77 in the precursor has A replacing the C, and SNP rs7025879 where the codon for Serine 174 in the precursor has C replacing the T, have also been identified. These examples are intended to be exemplary and non-limiting.

In one embodiment of the methods described herein, determining a level of an interferon gene product in a sample obtained from an individual comprises determining the level of interferon polypeptide in the sample. In one embodiment of the methods described herein, determining a level of an interferon gene product comprises determining the level of a putative secreted portion of human interferon in the sample, such as but not limited to, a secreted interferon polypeptide. Non-limiting examples of other methods of mRNA measurement and quantification include utilizing polymerase chain reaction, single nucleotide polymorphisms, single hairpin loops, and/or locked nucleic acids.

The level of an interferon polypeptide may be determined by contacting the biological sample with an antibody which specifically binds to interferon and determining the amount of bound antibody, e.g., by detecting or measuring the formation of the complex between the antibody and an interferon polypeptide. Antibodies may be used which bind to a secreted form of interferon, or to altered forms of the interferon protein, including addition proteolytic products. The term antibody as used herein is intended to include whole antibodies, e.g., of any isotype (IgG, IgA, IgM, IgE, etc) and fragments which are also specifically reactive with interferon or a complex comprising interferon. Antibodies can be fragmented using conventional techniques and the fragments screened in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibodies used in the present invention are further intended to include bispecific and chimeric molecules, as well as single chain (scFv) antibodies. The sample may be whole blood, serum, plasma, and the like.

The interferon antibodies may include trimeric antibodies and humanized antibodies, which may be prepared as described, e.g., in U.S. Pat. No. 5,585,089. Single chain antibodies may also be used to detect levels of interferon polypeptides. All of these modified forms of antibodies as well as fragments of antibodies are intended to be included in the term "antibody". Antibodies which bind to interferon may also be obtained commercially. For example, a purified IgG Antibody specific for residues 51-108 of human interferon may be purchased from Phoenix Pharmaceuticals, Inc. Alternatively, a rabbit polyclonal antibody to human interferon may also be purchased from BioVision, Inc.

The antibodies may be labeled (e.g., radioactive, fluorescently, biotinylated or HRP-conjugated) to facilitate detection of the complex. Appropriate assay systems for detecting interferon polypeptide levels include, but are not limited to, Enzyme-Linked Immunosorbent Assay (ELISA), competition ELISA assays, Radioimmuno-Assays (RIA), immunofluorescence, western, and immunohistochemical assays which involve assaying an interferon gene product in a sample using antibodies having specificity for interferon. Numerous methods and devices are well known to the skilled artisan for the detection and analysis of interferon of the instant invention. With regard to polypeptides or proteins in test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. These devices and methods may utilize labeled molecules in various sandwich, competitive, or non-competitive assay formats, to generate a signal that is related to the presence or amount of an analyte of interest. Additionally, certain methods and devices, such as but not limited to, biosensors and optical immunoassays, may be employed to determine the presence or amount of analytes without the need for a labeled molecule. See, e.g., U.S. Pat. Nos. 5,631,171 and 5,955,377, each of which is hereby incorporated by reference in its entirety, including all tables, figures and claims.

An amplified immunoassay, such as but not limited to, immuno-PCR may also be used. In this technique, the antibody may be covalently linked to a molecule of arbitrary DNA comprising PCR primers, whereby the DNA with the antibody attached to it is amplified by the polymerase chain reaction. See Hendrickson et al. *Nucleic Acids Res.* 23, 522-529, 1995; or T. Sano et al., in "Molecular Biology and Biotechnology" ed. Robert A. Meyers, VCH Publishers, Inc. (1995), pp. 458-460. Levels of interferon polypeptides may also be determined using protein microarrays. Methods of producing protein microarrays that may be adapted for detecting levels of interferon protein in a clinical sample are described in the art (see for example of Xiao et al. *Mol. Cell. Endocrinol.* 230, 95-106, 2005; Protein Microarrays (2004) Mark Schena (Ed) Jones & Bartlett Publishers, Inc.). U.S. Patent Publication No. 2003/0153013 describes methods of detecting proteins, e.g., antigens or antibodies, by immobilizing antibodies in a protein microarray on a membrane and contacting the microarray with detection proteins which can bind to the proteins to form protein complexes. Similarly, U.S. Patent Publication No. 2004/0038428 describes methods of constructing protein microarrays.

Alternatively, the level of interferon polypeptide may be detected using mass spectrometric analysis. Mass spectrometric analysis has been used for the detection of proteins in serum samples (see, e.g., Wright et al. *Prostate Cancer Prostatic Dis.* 2, 264-276, 1999; and Petricoin et al. *Lancet* 359, 572-7, 2002). U.S. Patent No. 2003/0013120 describes a system and method for differential protein expression and a diagnostic biomarker discovery system that may be adapted for measuring levels of interferon polypeptides in a fluid sample. Mass spectroscopy methods include Surface Enhanced Laser Desorption Ionization (SELDI) mass spectrometry (MS), SELDI time-of-flight mass spectrometry (TOF-MS), Maldi Q TOF, MS/MS, TOF-TOF, ESI-Q-TOF and ION-TRAP.

In an embodiment of the methods described herein, determining the level of an interferon gene product in a biological sample comprises determining the level of an interferon polypeptide having a post-translational modification, such as a phosphorylated, glycosylated or proteolytic processed interferon polypeptide. Phosphorylation may include phosphorylation of a tyrosine, serine, threonine or histidine. Antibodies that may be used to detect these modifications may include phosphotyrosine-specific antibody, phosphoserine-specific antibody, phosphoserine-specific antibody, and phospho-threonine-proline antibody, for example. Proteolytic processing may be detected by using antibodies specific for a cleaved product or by amino acid sequencing of the interferon protein.

In an embodiment, a method may detect and/or measure the concentration the polypeptide of the invention in a variety of matrices including culture supernatant, serum, plasma, extracellular fluid, whole blood, sputum, and nasal secretions. The detection and/or measurement method may comprise immunoassays such as ELISAs, ECL and others which detect these molecules at a sensitivity of less than 25 pg/mL, less than 10 pg/mL., less than 5 pg/mL, less than 1 pg/mL, and the like. The detection and/or measurement method may comprise antiviral assays including cytopathic effect inhibition assays and viral yield reduction assays. The assay may be a cytopathic effect assay, a viral yield reduction assay, a plaque assay, a reporter gene assay, a PCR-based assay, an immunoassay, and the like. In an embodiment of the method, the polypeptides may function as biomarkers correlating with a) particular disease states, acute or chronic disease states including Viral infections, Cancer, Autoimmune states, Immunocompromised states, Other hyper- or hypoimmune conditions; b) Responses to administration of pharmacological agents, toxins, or therapeutic interventions; c) General immune function; d) General toxicology, and the like. In an embodiment of the method, the may function as immunotoxicological markers correlating with Responses to administration of pharmacological agents, toxins, or therapeutic interventions, General toxicology, and the like. The subject may be a non-human primate. The methods described herein may be used to predict the effect of human interferons administered to humans. The methods described herein may be used to determine the efficacy of interferon in animal models of human disease. The methods described herein may be used to determine the side effect profile of interferons. The methods described herein may be used to predict responses of higher primates to administration of interferons and agents to be used in combination with interferons.

In an aspect of the invention, a method of identifying an intervention that increases or decreases the expression of any of the polypeptides described herein may comprise: obtaining a biological sample; exposing said biological sample to an intervention; waiting a specified period of time; assessing changes in gene expression levels, levels of RNA, protein, or protein activity levels related to one or more biomarkers of immune function of subject toxicity; and identifying said intervention as one that results in altered expression of any of the polypeptides as described herein. In an embodiment, the biological sample comprises cells. The cells may be obtained from a mammal. The mammal may be a non-human primate. In an embodiment, said change in gene expression levels, levels of RNA, protein, or protein activity levels may correspond to a change in gene expression for a gene encoding any one of a STAT, ISG, ISRE, and IRF protein. In an embodiment, intervention may be a Toll-Like Receptor agonist or antagonist. In an embodiment, intervention may be an immune response modulator.

The present invention also provides a screening method for identifying natural or synthetic substances compounds capable of enhancing or inhibiting the expression of an interferon polypeptide. In this assay, an increase in interferon expression levels as compared to the standard indicates that the candidate compound is an agonist of interferon expression and a decrease in expression levels as compared to the standard indicates that the compound is an antagonist of interferon expression. These may occur through transmembrane receptors including Toll-Like Receptors or through intracellular components of innate immunity including retinoic acid inducible gene 1 (RIG-1).

The invention now being generally described, it will be more readily understood by reference to the following examples, which are included merely for purposes of illustration of certain aspects and embodiments of the present invention, and are not intended to limit the invention, as one skilled in the art would recognize from the teachings hereinabove and the following examples, that other variant polypeptides, anti-viral assays, anti-proliferation assays, cell lines, purification assays, data analysis methods, and the like, all without limitation, can be employed, without departing from the scope of the invention as claimed.

The practice of aspects of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Various publications, patents, and patent publications are cited throughout this application the contents of which are incorporated herein by reference in their entirety.

The invention now being generally described, it will be more readily understood by reference to the following examples which are included merely for purposes of illustration of certain aspects and embodiments of the present invention, and are not intended to limit the invention. These and other systems, methods, objects, features, and advantages of the present invention will be apparent to those skilled in the art from the following detailed description of the preferred embodiment and the drawings. All documents mentioned herein are hereby incorporated in their entirety by reference.

EXEMPLIFICATION

Example 1

Cynomolgus IFN-α Full Length Gene Isolation, Sequence Determination, and Bacterial Expression Full length rhesus and Cynomolgus interferon alpha (IFN-α) subtypes were isolated using established PCR methods and cloned into pcDEF3-based mammalian expression vector which utilizes the human polypeptide chain elongation factor 1α promoter (EF-1α) (Goldman et al. *Biotechniques* 21, 1013-1015, 1996). Nucleotide sequence identity was determined by fluorescent based DNA sequencing methods (IDT DNA).

The mature open reading frame for Cynomolgus IFN SEQ ID 66 was subcloned into a standard bacterial expression vector, *E. coli* transformed, and biomass prepared through means familiar to those skilled in the art. Inclusion bodies were prepared by lysis of the *E. coli* and centrifugation, denatured in 7 M guanidine hydrochloride and refolded using standard glutathione ox/red conditions in the presence of 0.5 M arginine. The interferon was precipitated with ammonium sulfate (3 M final) followed by centrifugation. Precipitated interferon was resuspended in buffer and purified through standard chromatographic techniques including gel filtration and ion exchange chromatographies familiar to those skilled in the art.

Example 2

Preparation of Cynomolgus IFN-α Expression Plasmid DNA for Transfection Studies

Plasmid DNA was isolated with EndoFree Plasmid Maxi kit (Qiagen, Cat. #12362) to ensure a high quality endotoxin-free DNA for transfection and expression in mammalian cells. Plasmids were constructed to contain appropriate coding and noncoding portions of DNA SEQ IDs 41, 43, 45, 47, 49, 51, 53, 55, 57, 59, 61, and 65, intended to allow expression of protein SEQ IDs 42, 44, 46, 48, 50, 52, 54, 56, 58, 60, 62, and 66, respectively, in transiently transfected cells.

Example 3

Cell Culture and Transfection Procedure

African green monkey kidney-Vero cells lacking the IFN-α and IFN-β genes were obtained from American Type Culture Collection (CCL-81) were maintained in Modified Eagle Medium (MEM) supplemented with 10% (v/v) heat-inactivated fetal bovine serum. One day before transfection, cells were plated at 250,000 cells per well in 6-well plates and incubated overnight at 37° C. with 5% $CO_2$ to 70-80% confluence. Vero cells were tranfected with each Cynomolgus IFN-α subtype plasmids (containing DNA SEQ IDs 41, 43, 45, 47, 49, 51, 53, 55, 57, 59, 61, and 65) using Lipofectamine-PLUS reagent from Invitrogen according to the manufacturer's protocol. Briefly, 5 µg of plasmid DNA were mixed with 6.25 µL Lipofectamine-PLUS reagent in a serum-free MEM media and incubated at room temperature for 30 min. The combined DNA-Lipofectamine complexes were added to the cell monolayer, incubated for 6 h at 37° C. with 5% $CO_2$, then the transfection mixture was replaced with fresh growth media and further incubated at 37° C. in a 5% $CO_2$. Tissue culture supernatants were collected 24 h post-transfection, aliquoted and stored frozen at −20° C. until use. Biological activities of expressed Cynomolgus IFN-α proteins (SEQ IDs 42, 44, 46, 48, 50, 52, 54, 56, 58, 60, 62, and 66) were determined using reporter, antiviral, and antiproliferative cell-based assays. In addition, the mass concentrations of the IFN concentrations were estimated by using commercially available ELISA kits containing human IFN-α2a as a standard. Vector only and mock-transfected samples were used as controls and analyzed in parallel in all assays.

Example 4

Assay of IFN-α Antiviral Activity on Human A549 Cells

Figure 2:
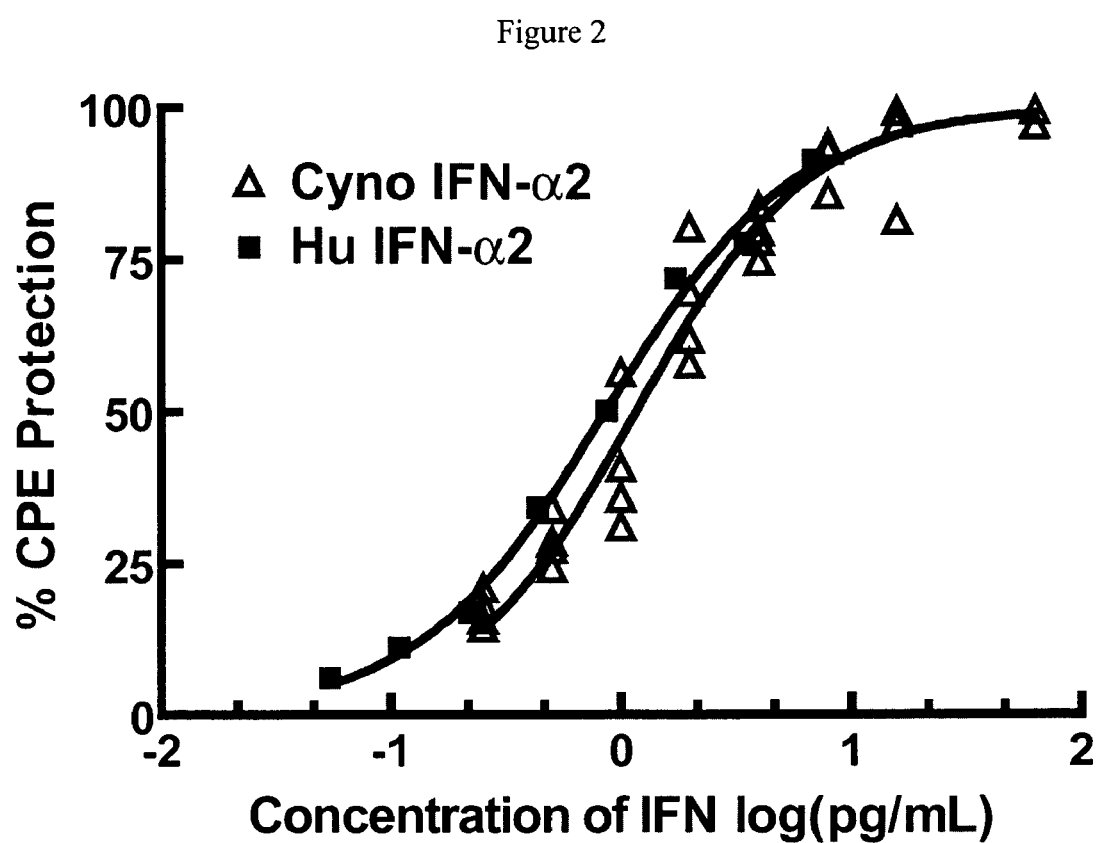
FIG. 2 depicts a cytopathic effect inhibition assay performed on human A549 cells in which human interferon alpha 2 activity is compared to that of Cynomolgus interferon alpha 2 (SEQ ID NO: 66), both purified from inclusion bodies after expression in E. coli. Together with the results depicted in Table 1 (A549 cells), these data demonstrate that the Cynomolgus interferon alpha proteins expressed either in *E. coli* or in mammalian cell culture supernatants each exhibit protection of human cells from the cytopathic effects of viruses. This is a hallmark of interferon activity.

The activity of Cyno IFN-α2 (Ile 16; SEQ ID NO: 66) and human IFN-α2 on human cells (A549) was measured using the following assay. The human lung epidermal carcinoma cells, A549, were plated in 96-well tissue culture plates at 10,000 cells per well in 0.1 mL of media. These were allowed to adhere for 1-4 h and then serial dilutions of the test IFNs were added in 0.1 mL. After incubation for 18-24 h at 37° C. with 5% $CO_2$ in a tissue culture incubator, 0.05 mL of a dilution of encephalomyocarditis virus was added which had been empirically determined to kill all of the untreated cells within 36 h. The plates were returned to the incubator and after 48 h the media was removed and the remaining cells stained with Crystal Violet. After extensive washes with water, the plates were allowed to dry. The dye was then solubilized with 70% methanol/water and the absorbance read at 570 nm on a Molecular Devices plate reader. A series of six wells to which no virus was added were averaged as the 100% protection value, and a series of six wells with virus but no interferon were averaged as the 0% protection. The absorbance values for the various dilutions were then transformed to percent protection and plotted in GraphPad Prism using a variable slope sigmoidal curve fit (see FIG. 2).

The concentration of the lab human IFN-α2a standard (calibrated to the International human IFN-α2a standard) in U/mL and for the unknown samples the dilution which resulted in 50% protection was taken as the assay $EC_{50}$. The dilution of the parent Cynomolgus IFN-α sample at the $EC_{50}$ was multiplied by the U/mL of the standard at the $EC_{50}$ to calculate the U/mL of Cynomolgus IFN-α contained each tissue culture supernatant sample.

Antiviral activities of 12 different Cynomolgus IFN-α supernatants were assessed on human cells by cytopathic effect inhibition assay. The supernatants from the transiently transfected Vero cells were titrated in 96-well plates, and the abilities of these IFNs to protect A549 cells from EMCV virus infection were determined with respect to a human IFN-α2a standard which is active on this cell line. Eleven of the 12 supernatants contained interferon which was active on this cell line (see Table 1 and FIG. 2). These data confirm that the identified sequences represent true interferon molecules as they exhibit the hallmark activity of Type I interferon, i.e., protection of cells from viral infection.

TABLE 1

| | Antiviral activity in A549 cells, Vero TC supernatant (U/mL) | Antiviral activity in JTC 12 cells Vero TC supernatant (U/mL) | OvCar-3 $EC_{50}$ (µL of supe) |
|---|---|---|---|
| SEQ ID 42 | 9410 | 35300, 39800 | <0.1 |
| SEQ ID 44 | 1260, 933 | 2690, 2690, <53, 320 | 10.76 |
| SEQ ID 46 | 10400 | 1050, <41 | 5.82 |
| SEQ ID 48 | 1260, 2930 | 181, 606 | 8.17 |
| SEQ ID 50 | 6600, 5660 | 986, 1380, <53, 176 | 4.85 |
| SEQ ID 52 | 276, 237 | <4, <13 | >25 |
| SEQ ID 54 | 10000, 5560 | 13300, 3440, 14500, 7680 | 1.99 |
| SEQ ID 56 | 1750, 2800 | 3880, 5530 | 13.86 |
| SEQ ID 58 | 8400, 5530 | 5530, 3400 | 0.85 |
| SEQ ID 60 | 39900 | 295000, 103000, 59600, 116000 | 0.04 |
| SEQ ID 62 | 3180, 20500 | 12600 | 0.42 |
| SEQ ID 66 | 6760, 9580 | 2850, 3240, 3090 | 2.55 |
| SEQ ID 66 | $1.00 \times 10^7$ | $1.49 \times 10^6$ | N/A |

Example 5

Assay of IFN-α Antiviral Activity on Cynomolgus Monkey Cells

JTC-12 cells were obtained from Health Science Research Resources Bank (Osaka, Japan). Cells were grown at 37° C. in a humidified incubator with 5% $CO_2$ in DMEM (Gibco) with 10% fetal bovine serum (Gibco). Cells were treated with Trypsin/EDTA (Gibco) and diluted to $2.9 \times 10^6$ cells/mL. Cells were plated for assay by adding 0.1 mL of this suspension to the middle six rows of a 96-well tissue culture plate (Falcon) and returned to the incubator for 2-4 h. Two fold dilutions of Cynomolgus IFN-α protein (SEQ IDs 42, 44, 46, 48, 50, 52, 54, 56, 58, 60, 62, and 66) expressed in tissue culture supernatant were prepared in growth media in separate plate. Each plate contained one row of a human IFN-α2a lab standard prepared from PBL #11100 which had been calibrated to the International standard for IFN-α2a (Gxa01-901-535), six wells which would receive virus but no IFN (virus control) and six wells which would receive no IFN and no virus (Cell control). Cynomolgus IFN-α proteins (SEQ IDs 42, 44, 46, 48, 50, 52, 54, 56, 58, 60, 62, and 66) expressed in tissue culture supernatant were each titrated in duplicate across 12 wells to determine dose response curves. After the plate containing the cells had incubated for 2-4 h, 0.1 mL of each sample was added to the cells and the plate was then allowed to interact with the cells for 16-20 h in the incubator. After this incubation, 0.05 mL of a dilution of EMC virus which had been empirically determined to cause nearly 100% cell lysis after 40 h of incubation was added to the cells. The EMC virus stock was prepared by growth on Vero cells and frozen at −80° C. After 40-48 h, the media were replaced with a crystal violet solution and the cells were stained for >10 minutes. Excess crystal violet was removed by immersion of the plate in clear tap water repeatedly until no visible dye was released from the wells. The plate was dried for 2-24 h and the crystal violet was solubilized by addition of 0.1 mL of 70% methanol to each well. The OD 570 or 562 was determined in a Molecular Devices 96-well plate reader. Data were analyzed by setting the average of the six cell control wells as 100% protection and the average of the six virus control wells as 0% protection. Dose response curves were plotted using GraphPad Prism and analyzed by a sigmoidal-fit (variable slope) equation. The concentration of the lab human IFN-α2a standard (calibrated to the International human IFN-α2a standard) in U/mL and for the unknown samples the dilution which resulted in 50% protection was taken as the assay $EC_{50}$. The dilution of the parent Cynomolgus IFN-α sample at the $EC_{50}$ was multiplied by the U/ml of the standard at the EC50 to calculate the U/ml of IFN contained each tissue culture supernatant sample.

Antiviral activities of 12 different Cynomolgus IFN-α supernatants were Cynomolgus monkey cells by cytopathic effect inhibition assay. The supernatants from the transiently transfected Vero cells were titrated in 96-well plates, and the abilities of these IFNs to protect JTC-12 cells from EMCV virus infection were determined with respect to a human IFN-α2a standard which is active on this cell line. Eleven of the 12 supernatants contained interferon which was active on this cell line (Table 1). These data further confirm that the identified sequences represent true interferon molecules as they exhibit the hallmark activity of Type I interferon, i.e., protection of cells from viral infection.

Example 6

Assay of IFN-α Antiviral Activity on Rhesus Monkey Cells

The activity of Cyno IFN Alpha 2 (Ile 16; SEQ ID NO: 66) and human IFN-α2 on Rhesus cells (LLC-MK2) was measured using the following assay. Rhesus LLC-MK2 cells were plated in 96 well tissue culture plates at 20,000 cells per well in 0.1 mL of media. These were allowed to adhere for 1-4 h and then serial dilutions of the test IFNs were added in 0.1 mL. After incubation for 18-24 h at 37° C. with 5% $CO_2$ in a tissue culture incubator, 0.05 mL of a dilution of vesicular stomatitis virus was added which had been empirically determined to kill all of the untreated cells within 36 h. The plates were returned to the incubator and after 48 h the media was removed and the remaining cells stained with Crystal Violet. After extensive washes with water, the plates were allowed to dry. The dye was then solubilized with 70% methanol/water and the absorbance read at 570 nm on a Molecular Devices plate reader. A series of six wells to which no virus was added were averaged as the 100% protection value, and a series of six wells with virus but no interferon were averaged as the 0% protection. The absorbance values for the various dilutions were then transformed to percent protection and plotted in GraphPad Prism using a variable slope sigmoidal curve fit (see FIG. 1).

FIG. 1 depicts a cytopathic effect inhibition assay performed on Rhesus LLC-MK2 cells wherein human interferon alpha 2 activity is compared to that of Cynomolgus interferon alpha 2 (SEQ ID NO: 66), both purified from inclusion bodies after expression in E. coli. Together with the results depicted in Table 1 (JTC 12 cells), these data demonstrate that the majority Cynomolgus interferon alpha proteins of the subject invention expressed either in E. coli or in mammalian cell culture supernatants exhibit protection of non-human primate cells from the cytopathic effects of viruses. This is a hallmark of interferon activity. Therefore, the classification of these proteins and their cognate DNAs as interferon alpha proteins and genes appears appropriate, and these specific examples suggest that all of the subject sequences will exhibit bioactivities indicative of interferon proteins.

Example 7

Antiproliferative Activities of Cynomolgus IFN-α Subtypes

The human ovarian adenocarcinoma cells, OVCAR-3 (ATCC, #HTB-161) were maintained in RPMI 1640 medium (Invitrogen, 22400) supplemented with 20% fetal bovine serum and 0.01 mg/ml bovine insulin (Sigma, # 10516). Cells were plated in 96-well tissue culture plates at 1,000 cells per well in 0.1 mL media, allowed to adhere for 1-4 h and then serial dilutions of the Cynomolgus IFN-α proteins (SEQ IDs 42, 44, 46, 48, 50, 52, 54, 56, 58, 60, 62, and 66) expressed in tissue culture supernatant were added in 0.1 mL volume. After six days incubation at 37° C. with 5% $CO_2$ in a tissue culture incubator, the conditioned media were removed, 0.1 mL of fresh media containing MTS/PMS reagent (1:6 v/v; Promega, CellTiter 96 Aqueous Non-Radioactive Cell Proliferation Assay, #G5430) was added. After 3-4 h incubation at 37° C., the amount of soluble formazan produced by cellular reduction of the MTS was measured at 490 nm in an ELISA plate reader. This colorimetric method for determines the number of viable cells based on the bioreduction of the tetrazolium compound (3-(4, 5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS). The conversion of MTS into aqueous, soluble formazan is accomplished by dehydrogenase enzymes found in metabolically active cells and its quantity (measured by the amount of 490 nm absorbance) is directly proportional to the number of viable cells in culture.

Antiproliferative activities of 12 different Cynomolgus IFN-α supernatants were assessed on human OvCar-3 cells with respect to a human IFN-α2a standard which is active on this cell line. Eleven of the 12 supernatants contained interferon which was active in this cell-based bioassay, and their $EC_{50}$ values are shown as μL of tissue culture supernatant required to half-maximally inhibit cell proliferation (Table 1). These data further confirm that the identified sequences represent true interferon molecules as they exhibit the hallmark activity of Type I interferon, i.e., inhibition of the growth of malignant cells in culture.

Example 8

Reporter Cell-Based Assay of Cynomolgus IFN-α and Neutralization of the Bioactivity of Cynomolgus IFN-α Subtypes Quantitative determination of the bioactivities of Cynomolgus IFN-α proteins (SEQ IDs 42, 44, 46, 48, 50, 52, 54, 56, 58, 60, 62, and 66) secreted in the tissue culture supernatants was carried out by using the iLite human IFN-α gene-reporter cell-based assay kit according to kit protocol (iLite™ Human Interferon-Alpha Kit, Product #51100-1, PBL Biomedical Laboratories). The assay detects the quantity of active induced luciferase enzyme molecules which is directly proportional to a) the number of IFN-α molecules that have bound to cellular IFN receptors combined with b) the specific activities of those IFN molecules in activating the receptor. Briefly, appropriate volumes of cell culture supernatant were mixed with sample buffer, added to the reporter cells in 96-well test plates and incubated for 17 h at 37° C. with 5% $CO_2$. The luminescent substrate for the luciferase enzyme is added directly to cells and the reaction product measured in a luminometer. The level of the luciferase enzyme activity observed in the particular sample is compared to that obtained using a standard IFN, namely human IFN-α2a, calibrated to the International human IFN-α2a standard.

Assays examining the neutralization of the bioactivity of each Cynomolgus IFN-α protein (SEQ IDs 42, 44, 46, 48, 50, 52, 54, 56, 58, 60, 62, and 66) expressed in tissue culture supernatant were performed using the iLite human IFN-α gene-reporter cell-based assay kit as described above with the following additional steps. Each Cynomolgus IFN-α supernatant sample was diluted to an activity of 12.5 U/mL based on values obtained in the initial iLite activity assay. Subsequently, each interferon sample was pre-mixed with anti-human Type I IFN receptor chain 2 antibodies (Mouse Monoclonal Antibody Against Human Interferon Alpha/Beta Receptor Chain 2 #21385-1, PBL Biomedical Laboratories), then the mixture added to the iLite cells and incubated at 37° C., 5% $CO_2$ for 17 h. Non-Type I IFN receptor antibody samples were also included as negative controls. In each experiment, the control antibody was diluted to the same concentration as the neutralizing/blocking antibodies.

The ability of these interferon supernatants to induce a luciferase expression response in a cell-based assay of IFN activity was executed using a commercial rapid bioassay kit (Product #51100-1, PBL Biomedical Laboratories). All 12 supernatants generated a luciferase response over control supernatant indicating that these supernatants contained detectable and significant interferon bioactivity (Table 2). The activities of each of these 12 interferons in the iLite assay was quantitatively blocked (Table 2) using an antibody specifically directed against the Type I interferon receptor chain 2 (#21385-1, PBL Biomedical Laboratories), again indicating that each supernatant contains interferon bioactivity produced through the transient transfection of plasmids encoding DNA SEQ IDs 41, 43, 45, 47, 49, 51, 53, 55, 57, 59, 61, and 65, leading to expression of the Cynomolgus IFN-α proteins corresponding to protein SEQ IDs 42, 44, 46, 48, 50, 52, 54, 56, 58, 60, 62, and 66, respectively. These data then further confirm that the identified sequences represent true interferon molecules as they exhibit the hallmark activity of Type I interferon, i.e., activation of intracellular signaling cascades specifically through the Type I IFN receptor.

TABLE 2

| | Luciferase Induction Activity Activity (U/mL) | % Neutralization of Luciferase Induction by anti-Type I IFN Receptor Antibody (25 μg/mL) |
|---|---|---|
| SEQ ID 42 | 36732 | >99% |
| SEQ ID 44 | 2826 | >99% |
| SEQ ID 46 | 2699 | >99% |

TABLE 2-continued

| | Luciferase Induction Activity Activity (U/mL) | % Neutralization of Luciferase Induction by anti-Type I IFN Receptor Antibody (25 µg/mL) |
|---|---|---|
| SEQ ID 48 | 2173 | >99% |
| SEQ ID 50 | 8042 | >99% |
| SEQ ID 52 | 515 | >99% |
| SEQ ID 54 | 11552 | >99% |
| SEQ ID 56 | 822 | >99% |
| SEQ ID 58 | 8946 | >99% |
| SEQ ID 60 | 48894 | >99% |
| SEQ ID 62 | 16050 | >99% |
| SEQ ID 66 | 6626 | >99% |

Example 9

ELISA Activity of Cyno IFN-α2 and Hu IFN-α2

The reactivities of Cyno IFN-α2 (Ile 16; SEQ ID NO: 66) and human IFN-α2 were measured in an ELISA (PBL Biomedical Laboratories Product #41100-1) directed against human IFN alpha A. The detection of Cynomolgus IFN-α2 protein (SEQ ID NO: 66) was evaluated using a human IFN-alpha ELISA kit (PBL catalog #41100-1). The study was carried out using purified human interferon alpha 2 and said Cynomolgus IFN-alpha protein purified by standard chromatography methodology. The human and Cynomolgus proteins were each diluted to a concentration of 10,000 pg/mL in phosphate-buffered saline containing 0.1% BSA. Subsequently, serial dilutions were performed in ELISA kit sample buffer to concentrations of 1000, 500, 250, 125, 62.5, 31.25, 15.6 and 0.0 pg/mL per well). Samples were then assayed in the ELISA kit according to the protocol provided with the assay. FIG. 3 depicts an ELISA assay assessing the reactivity of the ELISA toward human interferon alpha 2 and Rhesus interferon alpha 2, and Cynomolgus interferon alpha 2 (SEQ ID NO: 66), both purified from inclusion bodies after expression in *E. coli*. Together with the results depicted in Table 3, these data demonstrate that the Cynomolgus interferon alpha proteins of the subject invention expressed either in *E. coli* or in mammalian cell culture supernatants are recognized by ELISAs directed against interferon alpha.

Two commercial human IFN-α ELISA kits (Human IFN-α Multi-Subtype ELISA kit, PBL # 41105, Human IFN-α ELISA, # 41100) were used to estimate the Cynomolgus IFN-α protein levels (SEQ IDs 42, 44, 46, 48, 50, 52, 54, 56, 58, 60, 62, and 66) present in the transfected cell tissue culture supernatants (Table 3). Samples were diluted in assay buffer and 100 µL were added to the ELISA plate. Dilutions of known amounts of human IFN-α2a (supplied in commercial kits) were also added to the ELISA plates. The assays were carried out according to the manufacturer's procedures. Plates were read at OD 450 nm using Vmax Kinetic Plate Reader (Molecular Devices Corporation). Data points comprising each standard curve were fitted by 4-parameter fit using SoftMax Pro v5.0 (Molecular Devices Corporation).

TABLE 3

| | 41105 ELISA assay of tissue culture supernatants | 41110 ELISA assay of tissue culture supernatants |
|---|---|---|
| SEQ ID 42 | 287, 566 | 0 |
| SEQ ID 44 | 256, 314 | 0 |
| SEQ ID 46 | 123, 187 | 0 |
| SEQ ID 48 | 45, 80 | 0 |
| SEQ ID 50 | >651, >1123 | 296 |
| SEQ ID 52 | 14, 17 | 0 |
| SEQ ID 54 | 8, 8 | 11 |
| SEQ ID 56 | 289, 414 | 0 |
| SEQ ID 58 | >651, >1123 | 66 |
| SEQ ID 60 | >651, 1000 | 0 |
| SEQ ID 62 | 75, 95 | 0 |
| SEQ ID 66 | >651, 1500 | 184 |
| Empty vector | 0 | 0 |

Taken together, these data indicate that the proteins corresponding to SEQ IDs 42, 44, 46, 48, 50, 52, 54, 56, 58, 60, 62, and 66 each exhibit one or more bioactivities characteristic of interferon molecules, particularly those interferon proteins that bind to the type I interferon receptor. In general the activities measured on the human and the Cynomolgus cells were of similar magnitude suggesting that the IFNAR1 and IFNAR2 receptors in these species exhibit similar responses to several Cynomolgus IFN-α proteins.

We have classified these as proteins as IFN-α proteins based on their DNA sequence homologies to published human and rhesus IFN-α DNA sequences. However, each of the sequences contained herein are unique from each other and from the human and rhesus sequences published to date.

Sequences of the Invention

```
                                              SEQ ID NO: 1
ATGGCCCTGTCCTTTTCTTTACTGATGGCCGTGGTGGTGCTCAGCTACAA

ATCCATCTACTCTCTGGGCTGTGATCTGCCTCAGATCCACAGCCTGGGTC

ATAGGAGGGCCTTGATACTCCTGGCACAAATGGGAAGGATCTCTCCTTTC

TCCTGTCTGAAGGACAGACATGACTTTGGATTCCCCCAGGAGGAGTTTGA

TGGCAACCAGTTCCAGAAGGCTCAAGCCATGTCTGTCCTCCATGAGATGA

TCCAGCAGACCTTCAATCTCTTCAGCACAAAGGACTCATCTGCTGCTTGG

GAACAGAACCTCCTAGAAAAATTTTCCGCTGAGCTTTACCAGCAACTGAA

TGACCTGAAAGCCTGTGTGATAGCAGAGCCTGGGATGGAAGACACTCCCT

TGATGAATGAGGACTCCATCCTGGCTGTGAAGAAATACTTCCAAAGAATC

ACTCTCTATCTGACGGAGAAGAAATACAGCCCATGTGCCTGGGAGGTTGT

CAGAACAGAAATCATGAGATCTCTCTCTTTTTCAACAAACTTGCAAAAAA

GATTAAGGAGGAAGGATTGA

SEQ ID NO: 2
MALSFSLLMAVVVLSYKSIYSLGCDLPQIHSLGHRRALILLAQMGRISPF

SCLKDRHDFGFPQEEFDGNQFQKAQAMSVLHEMIQQTFNLFSTKDSSAAW

EQNLLEKFSAELYQQLNDLKACVIAEPGMEDTPLMNEDSILAVKKYFQRI

TLYLTEKKYSPCAWEVVRTEIMRSLSFSTNLQKRLRRKD*

SEQ ID NO: 3
ATGGCCCTGTCCTTTTCTTTACTGATGGCCGTGGTGGTGCTCAGCTACAA

ATCCATCTACTCTCTGGGCTGTGATCTGCCTCAGATCCACAGCCTGGGTC

ATAGGAGGGCCTTGATACTCCTGGCACAAATGGGAAGGATCTCTCCTTTC

TCCTGTCTGAAGGACAGACATGACTTTGGATTCCCCCAGGAGGAGTTTGA

TGGCAACCAGTTCCAGAAGGCTCAAGCCATGTCTGTCCTCCATGAGATGA
```

TCCAGCAGACCTTCAATCCCTTCAGCACAAAGGACTCATCTGCTGCTTGG

GAACAGAACCTCCTAGAAAAATTTTCCGCTGAGCTTTACCAGCAACTGAA

TGACCTGAAAGCCTGTGTGATAGCAGAGCCTGGGATGGAAGACACTCCCT

TGATGAATGAGGACTCCCTCCTGGCTGTGAAgAAATACTTCCAAAGAATC

ACTCTCTATCTGACGGAGAAGAAATACAGCCCATGTGCCTGGGAGGTTGT

CAGAACAGAAATCATGAGATCTCTCTCTTTTTCAACAAACTTGCAAAAAA

GATTAAGGAGGAAGGATTGA

SEQ ID NO: 4
MALSFSLLMAVVVLSYKSIYSLGCDLPQIHSLGHRRALILLAQMGRISPF
SCLKDRHDFGFPQEEFDGNQFQKAQAMSVLHEMIQQTFNPFSTKDSSAAW
EQNLLEKFSAELYQQLNDLKACVIAEPGMEDTPLMNEDSLLAVKKYFQRI
TLYLTEKKYSPCAWEVVRTEIMRSLSFSTNLQKRLRRKD*

SEQ ID NO: 5
ATGGCCCTGTCCTTTTCTTTACTGATGGCCGTGGTGGTGCTCAGCTACAA
ATCCATCTGCTCTCTGGGCTGTGATCTGCCCCAGACCCACAGCCTGGGTC
ATAGGAGGGCCTTGATACTCCTGGAACAAATGGGAAGGATCTCTCCTTTC
TCCTGTCTGAAGGACAGACGTGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GAACAGAACCTCCTAGAAAAATTTTCCACCGAACTTTACCAGCAACTGAA
TGACCTGAAAGCCTGTGTGATAGCAGAGCCTGGGATGGAAGACACTCCCT
TGATGAATGAGGACTCCATCCTGGCTGTGAAGAAATACTTCCAAAGAATC
ACTCTCTATCTGACGGAGAAgAAATACAGCCCATGTGCCTGGGAGGTTGT
CAGAACAGAAATCATGAGATCCCTCTCTTTTTCAACAAACTTGCCAAAAA
GATTAAGGAGGAAGGATTGA

SEQ ID NO: 6
MALSFSLLMAVVVLSYKSICSLGCDLPQTHSLGHRRALILLEQMGRISPF
SCLKDRRDFGFPQEEFDGNQFQKAQAMSVLHEMIQQTFNLFSTKDSSAAW
EQNLLEKFSTELYQQLNDLKACVIAEPGMEDTPLMNEDSILAVKKYFQRI
TLYLTEKKYSPCAWEVVRTEIMRSLSFSTNLPKRLRRKD*

SEQ ID NO: 7
ATGGCCCTGTCCTTTTCTTTACTGATGGCCGTGGTGGTGCTCAGCTACAA
ATCCATCTGCTCTCTGGGCTGTGATCTTCCTCAGACCCACAGCCTGGGTC
ATAGGAGGGCCTTGATACTCCTGGCACAAATGGGAAGGATCTCTCCGTTC
TCCTGTCTGAAGGACAGACATGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GAACAGAACCTCCTAGAAAAATTTTCCGCTGAGCTTTACCAGCAACTGAA
TGACCTGAAAGCCTGTGTGATAGCAGAGCCTGGGATGGAAGACACTCCCT
TGATGAATGAGGACTCCATCCTGGCTGTGAAGAAATACTTCCAAAGAATC
ACTCTCTATCTGACGGAGAAGAAATACAGCCCTTGTGCCTGGGAGGTTGT
CAGAGCAGAAATCATGAGATCCCTCTCTTTTTCAACAAACTTGCAAAAAA
GATTAAGGAGGAAGGATTGA

SEQ ID NO: 8
MALSFSLLMAVVVLSYKSICSLGCDLPQTHSLGHRRALILLAQMGRISPF
SCLKDRHDFGFPQEEFDGNQFQKAQAMSVLHEMIQQTFNLFSTKDSSAAW
EQNLLEKFSAELYQQLNDLKACVIAEPGMEDTPLMNEDSILAVKKYFQRI
TLYLTEKKYSPCAWEVVRAEIMRSLSFSTNLQKRLRRKD*

SEQ ID NO: 9
ATGGCCCTGTCCTTTTCTTTACTGATGGCCGTGGTGGTGCTCAACTACAA
ATCCATCTGCTCTCTGGGCTGTGATCTTCCTCTGACCCAGAGCCTGGGTC
ATAGGAGGGCTTTGATACTCCTAGCACAAATGGGAAGAATCTCTCCTTTA
TCCTGTCTGAAGGACAGACATGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GAACAGAACCTCCTAGAAAAATTTTCCGCTGAGCTTTACCAGCAACAGAA
TGACCTGAAAGCCTGTGTGATAGCAGAGCCTGGGATGGAAGAGACTCTCT
TGATGAATGAGGACTCCATCCTGGCTGTGAAGAAATACTTCCAAAGAATC
ACTCTCTATCTGACGGAGAAGAAATACAGCCCATGTGCCTGGGAGGTTGT
CAGAGCAGAAATCATGAGATCCCTCTCTTTTTCAACAAACTTGCAAAAAA
GATTAAGGAGGAAGGATTGA

SEQ ID NO: 10
MALSFSLLMAVVVLNYKSICSLGCDLPLTQSLGHRRALILLAQMGRISPL
SCLKDRHDFGFPQEEFDGNQFQKAQAMSVLHEMIQQTFNLFSTKDSSAAW
EQNLLEKFSAELYQQQNDLKACVIAEPGMEETLLMNEDSILAVKKYFQRI
TLYLTEKKYSPCAWEVVRAEIMRSLSFSTNLQKRLRRKD*

SEQ ID NO: 11
ATGGCCCTGTCCTTTTCTTTACTGATGGCCATGGTGGTGCTCAGCTACAA
ATCCATCTGCTCTCTGGGCTGTGATCTGCCCCAAACCCACAGCCTGGGTC
ATAGGAGGGCCTTGATACTCCTAGCACAAATGGGAAGAATCTCTCCTTTC
TCCTGTCTGAAGGACAGACATGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GAACAGAACCTCCTAGAAAAATTTTCCGCTGAGCTTTACCAGCAACTGAA
TGACCTGAAAGCCTGTGTGATAGCAGAGCCTGGGATGGAAGACACTCCCT
TGATGAATGAGGACTCCATCCTGGCTGTGAAGAAATACTTCCAAAGAATC
ACTCTCTATCTGACGGAGAAAAAATACAGCCCTTGTGCCTGGGAGGTTGT
CAGAGCAGAAATCATGAGATCCCTCTCTTTTTCAACAAACTTGCAAAAAA
GATTAAGGAGGAAGGATTGA

SEQ ID NO: 12
MALSFSLLMAMVVLSYKSICSLGCDLPQTHSLGHRRALILLAQMGRISPF
SCLKDRHDFGFPQEEFDGNQFQKAQAMSVLHEMIQQTFNLFSTKDSSAAW

EQNLLEKFSAELYQQLNDLKACVIAEPGMEDTPLMNEDSILAVKKYFQRI
TLYLTEKKYSPCAWEVVRAEIMRSLSFSTNLQKRLRRKD*

SEQ ID NO: 13
ATGGCCCTGGTGGTGCTCAGCTGCAAGTCAAGTTGCTCTCTGGGCTGTGA
TCTGCCTCAGACCCACAGCCTGGGTCACAGGAGGACCATGATGCTCCTGG
TACAAATGAGAAGAATCTCTCTTTTCTCCTGTCTGAAGGACAGACACGAC
TTCAGATTTCCCCAGGAGGAGTTTGATGGCAACCAGTTCCAGAAGGCTCA
AGCTATCTCTGTCCTCCATGAGGTGATTCAGCAGACCTACAACCTCTTCA
GCACAAAGGACTCATCTGCTGCTTGGGATGAAATGCTTCTAGACAAACTC
TACACTGAACTTTACCAGCAGCTGAATGACCTGGAAGCCTGTGTGATGCA
GGAGGCGTGGGTGGGAGAGACTCCCCTGATGAATGAGGACTCCATCCTGG
CTGTGAGAAAATACTTCCAAAGAATCACTCTCTACCTGACAGAGAAGAAG
TATAGCCCTTGTGCATGGGAGGTTGTCAGAGCAGAAATCATGAGATCCTT
CTCTTCATCAAGAAACTTGCAAGAAAGATTAAGGAGGAAGGAATAA

SEQ ID NO: 14
MALVVLSCKSSCSLGCDLPQTHSLGHRRTMMLLVQMRRISLFSCLKDRHD
FRFPQEEFDGNQFQKAQAISVLHEVIQQTYNLFSTKDSSAAWDEMLLDKL
YTELYQQLNDLEACVMQEAWVGETPLMNEDSILAVRKYFQRITLYLTEKK
YSPCAWEVVRAEIMRSFSSSRNLQERLRRKE*

SEQ ID NO: 15
ATGGCCTTGCCTTTTGCTTTACTCATGGCCCTGGTGGTGCTCAGCTGCAA
GTCAAGTTGCTCTCTGGGCTGTGATCTGCCTCAGACCCACAGCCTGGGTC
ACAGGAGGACCATGATGCTCCTGGTACAAATGAGAAGAATCTCTCTTTTC
TCCTGTCTGAAGGACAGACACGACTTCAGATTTCCCCAGGAGGAGTTTGA
TGGCAACCAGTTCCAGAAGGCTCAAGCTATCTCTGTCCTCCATGAGGTGA
TTCAGCAGACCTACAACCTCTTCAGCACAAAGGACTCATCTGCTGCTTGG
GATGAAATGCTTCTAGACAAACTCTACACTGAACTTTACCAGCAGCTGAA
TGACCTGGAAGCCTGTGTGATGCAGGAGGCGTGGGTGGGAGAGACTCCCC
TGATGAATGAGGACTCCATCCTGGCTGTGAGAAAATACTTCCAAAGAATC
ACTCTCTACCTGACAGAGAAGAAGTATAGCCCTTGTGCATGGGAGGTTGT
CAGAGCAGAAATCATGAGATCCTTCTCTTCATCAAGAAACTTGCAAGAAA
GATTAAGGAGGAAGGAATAA

SEQ ID NO: 16
MALPFALLMALVVLSCKSSCSLGCDLPQTHSLGHRRTMMLLVQMRRISLF
SCLKDRHDFRFPQEEFDGNQFQKAQAISVLHEVIQQTYNLFSTKDSSAAW
DEMLLDKLYTELYQQLNDLEACVMQEAWVGETPLMNEDSILAVRKYFQRI
TLYLTEKKYSPCAWEVVRAEIMRSFSSSRNLQERLRRKE*

SEQ ID NO: 17
ATGGCCTTGACCTTTTATTTACTGATGGCCCTAGTGGTGCTCAGCTACAA
GCCATTCAGCTCTCTGGGCTGTGATCTGCCTCAGACCCACAGCCTGGGTT
ACAGGAGGCCCTTGGTGCTCCTGGCACAAATGAGAAGAATCTCTCCTTTC
TCCTGCCTGAAGGACAGACATGACTTTGAATTACCCCAGGAGGAGTTTGA
TGACAAAAACTTCCAGAAGGCTCAAGCCATCTCTGTCCTCCATGAGATAA

TCCAGCAGACCTTCAACCTCTTCAACACAAAGAATTCATCTGCTGCTTTC
AATGAGACCCTTCTAGATGAATTCTACATCGAACTTGACCAGCAGCTGAA
TGACCTGGAGTCCTGTGTGATGCAGGAAGTGGGGGTGACAGAGACTCACC
TGATGTACGAGGACTCCATCCTGGCTGTGAAGAAATACTTCCGAAGAATC
ACTCTCTATCTGACAGAGAAGAAATACAGCCCTTGTGCCTGGGAGGTTGT
CAGAGCAGAAATCATGAGATCCTTCTCTTTATCAATCAACTTGCAAAAAA
GATTGAAGAGTAAGGAATAA

SEQ ID NO: 18
MALTFYLLMALVVLSYKPFSSLGCDLPQTHSLGYRRPLVLLAQMRRISPF
SCLKDRHDFELPQEEFDDKNFQKAQAISVLHEIIQQTFNLFNTKNSSAAF
NETLLDEFYIELDQQLNDLESCVMQEVGVTETHLMYEDSILAVKKYFRRI
TLYLTEKKYSPCAWEVVRAEIMRSFSLSINLQKRLKSKE*

SEQ ID NO: 19
ATGGCATTGCCTTTTGCTTTACTGATGGCCCTGGTGGTGCTCAGCTGCAA
GTCAAGCTGCTCTCTGGGCTGTGATCTGCCTGAGACCCACAGCCTGGATA
ACAGAAGGACCATGATGCTCCTGAAACAAATGAGCAGAATCTCTCCTTCC
TCCTGTCTGATGGACAGACATGACTTTGGATTTCCCCAGCAGGAGTTTGA
TGGCAACCAGTTCCAGAAGGCTCCAGCCATCTCTGTCCTCCATGAGCTGA
TCCAGCAGACCTTCAACCTCTTTACCACAAAAGACTCATCTGCTGCTTGG
GATGAGGACCTCCTAGACAAATTCTGCACTGAACTCTACCAGCAGCTGAA
TGACTTGGAAGCCTGTGTCATGCAGCAGGAGAGGGTGGGAGAAACTCCCC
TGATGAATGCGGACTCCACCTTGGCTGTGAAGAAATACTTCCGAAGAATC
ACTCTCTATCTGACAGAGAAGAAATACAGCCCTTGTGCCTGGGAGGTTGT
CAGAGCAGAAATCATGAGATCTTTCTCTTTATCAACAAACTTGCAAGAAA
GATTAAGGAGGAAGGAATAA

SEQ ID NO: 20
MALPFALLMALVVLSCKSSCSLGCDLPETHSLDNRRTMMLLKQMSRISPS
SCLMDRHDFGFPQQEFDGNQFQKAPAISVLHELIQQTFNLFTTKDSSAAW
DEDLLDKFCTELYQQLNDLEACVMQQERVGETPLMNADSTLAVKKYFRRI
TLYLTEKKYSPCAWEVVRAEIMRSFSLSTNLQERLRRKE*

SEQ ID NO: 21
ATGGCATTGCCCTTTGCTTTACTGATGGCCCTGGTGGTGCTCAGCTGCAA
GTCAAGCTGCTCTCTGGGCTGTGATCTGCCTGAGACCCACAGCCTGGATA
ACAGAAGGACCATGATGCTCCTGAAACAAATGAGCAGAATCTCTCCTTCC
TCCTGTCTGATGGACAGACATGACTTTGGATTTCCCCAGCAGGAGTTTGA
TGGCAACCAGTTCCAGAAGGCTCAAGCCATCTCTGTCCTCCATGAGCTGA
TCCAGCAGACCTTCAACCTCTTTACCACAAAAGACTCATCTGCTGCTTGG
GATGAGGACCTCCTAGACAAATTCTGCACTGAACTCTACCAGCAGCTGAA
TGACTTGGAAGCCTGTGTCATGCAGCAGGAGAGGGTGGGAGAAACTCCCC
TGATGAATGCGGACTCCACCTTGGCTGTGAAGAAATACTTCCGAAGAATC
ACTCTCTATCTGACAGAGAAGAAATACAGCCCTTGTGCCTGGGAGGTTGT

```
CAGAGCAGAAATCATGAGATCCTTCTCTTTATCAACAAACTTGCAAGAAA
GATTAAGGAGGAAGGAATAA
                                       SEQ ID NO: 22
MALPFALLMALVVLSCKSSCSLGCDLPETHSLDNRRTMMLLKQMSRISPS
SCLMDRHDFGFPQQEFDGNQFQKAQAISVLHELIQQTFNLFTTKDSSAAW
DEDLLDKFCTELYQQLNDLEACVMQQERVGETPLMNADSTLAVKKYFRRI
TLYLTEKKYSPCAWEVVRAEIMRSFSLSTNLQERLRRKE*
                                       SEQ ID NO: 23
ATGGCCTTGCCCTTTGCTTTACTGATGGCCCTGGTGGTGCTCAGCAGCAA
GTCAAGTTGCTCTCTGGGCTGTGATCTGCCTGAGACCCACAGCCTGGATA
ACAGGAAGACCATGATGCTCCTGGCACAGATGAGCAGAATCTCTCCTTCC
TCCTGTCTGATGGACAGACATGACTTTGGATTTCCCCAGCAGGAGTTTGA
TGGCAACCAGTTCCAGAAGGCTCAAGCCATCTCTGTCCTCCATGAGCTGA
TCCAGCAGACCTTCAACCTCTTTACCACAAAAGACTCATCTGCTGCTTGG
GATGAGGACCTCCTAGACAAATTCTGCACTGAACTCTACCAGCAGCTGAA
TGACTTGGAAGCCTGTGTCATGCAGCAGGAGAGGGTGGGAGAAACTCCCC
TGATGAATGCGACTCCACCTTGGCTGTGAAGAAATACTTCCGAAGAATC
ACTCTCTATCTGACAGAGAAGAAATACAGCCCTTGTGCCTGGGAGGTTAT
CAGAGCAGAAATCATGAGATCCTTCTCTTTATCAACAAACTTGCAAGAAA
GATTAAGGAGGAAGGAATAA
                                       SEQ ID NO: 24
MALPFALLMALVVLSSKSSCSLGCDLPETHSLDNRKTMMLLAQMSRISPS
SCLMDRHDFGFPQQEFDGNQFQKAQAISVLHELIQQTFNLFTTKDSSAAW
DEDLLDKFCTELYQQLNDLEACVMQQERVGETPLMNADSTLAVKKYFRRI
TLYLTEKKYSPCAWEVIRAEIMRSFSLSTNLQERLRRKE*
                                       SEQ ID NO: 25
ATGGCATTGCCCTTTGCTTTAATGATGGCCCTGCTGGTGCTTAGCTACAA
GTCAAGCTGCTCTCTGGGCTGTAATCCATCTCAAACCCACAACATGAATA
ACAGGAGGACTTTGATGCTCATGGCACAAATGAGGAGAATCTCTCCTTTT
TCATGCCTGAAGGACAGAAATGACTTTGAATTTCCCCAGGAGGAGTTTGA
TGGCAACCAGTTCCAGAATACTCAAGCCATCTCTCTCCTCCATGAGATGA
TCCAGCAGACCTTCAATCTCTTCAGCACAAAGGACTCATCTGCTGCTTGG
GATGAGACCCTCCTAGACAAATTCTACATTGAACTTTTCCAGCAACTGAA
TGACCTGGAAGCCTGTGTGATACAGGAGGCTGGGGTAGAAGAGACTCCCC
TGATGAATGAGGACTCCATCCTGGCTGTGAAGAAATACTTCCAAAGAATC
ACTCTCTATCTGATGGAGAAGAAATACAGCCCATGTGCCTGGGAGGTTGT
CAGAGCAGAAATCATGAGATCCCTCTCTTTTTCAACAAACTTGCAAAAAA
GATTAAGGAGGAAGGATTGA
                                       SEQ ID NO: 26
MALPFALMMALLVLSYKSSCSLGCNPSQTHNMNNRRTLMLMAQMRRISPF
SCLKDRNDFEFPQEEFDGNQFQNTQAISLLHEMIQQTFNLFSTKDSSAAW
DETLLDKFYIELFQQLNDLEACVIQEAGVEETPLMNEDSILAVKKYFQRI
TLYLMEKKYSPCAWEVVRAEIMRSLSFSTNLQKRLRRKD*
                                       SEQ ID NO: 27
ATGGCATTGCCCTTTGCTTTAATGATGGCCCTGCTGGTGCTTAGCTACAA
GTCAAGCTGCTCTCTGGGCTGTAATCCATCTCAAACCCACAACATGAATA
ACAGGAGGACTTTGATGCTCATGGCACAAATGAGGAGAATCTCTCCTTTT
TCATGCCTGAAGGACAGAAATGACTTTGAATTTCCCCAGGAGGAGTTTGA
TGGCAACCAGTTCCAGAATACTCAAGCCATCTCTCTCCTCCATGAGATGA
TCCAGCAGACCTTCAATCTCTTCAGCACAAAGGACTCATCTGCTGCTTGG
GATGAGACCCTCCTAGACAAATTCTACATTGAACTTTTCCAGCAACTGAA
TGACCTGGAAGCCTGTGTGATACAGGAGGCTGGGGTAGAAGAGACTCCCC
TGATGAATGAGGACTCCATCCTGGCTGTGAAGAAATACTTCCAAAGAATC
ACTCTCTATCTGATGGAGAAGAAATACAGCCCATGTGCCTGGGAGGTTGT
CAGAGCAGAAATCATGAGATCCCTCTCTTTTTCAACAAACTTGCAAAAAA
GATTAAGGAGGAAGGATTGA
                                       SEQ ID NO: 28
MALPFALMMALLVLSYKSSCSLGCNPSQTHNMNNRRTLMLMAQMRRISPF
SCLKDRNDFEFPQEEFDGNQFQNTQAISLLHEMIQQTFNLFSTKDSSAAW
DETLLDKFYIELFQQLNDLEACVIQEAGVEETPLMNEDSILIAVRKYFQR
ITLYLMEKKYSPCAWEVVRAEIMRSLSFSTNLQKRLRRKD*
                                       SEQ ID NO: 29
ATGGCCCTGTCCTTTTCTTTACTGATGGCCATGGTGGTGCTCAGCTACAA
ATCCATCTGCTCTCTGGGCTGTGATCTGCCCCAAACCCACAGCCTGGGTC
ATAGGAGGGCCTTGATACTCCTAGCACAAATGGGAAGAATCTCTCCTTTC
TCCTGTCTGAAGGACAGACATGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GATGAGACCCTCCTAGACAAATTCTACATTGAACTTTTCCAGCAACTGAA
TGACCTGGAAGCCTGTGTGATACAGGAGGCTGGGGTAGAAGAGACTCCCC
TGATGAATGAGGACTCCATCCTGGCTGTGAAGAAATACTTCCAAAGAATC
ACTCTCTATCTGACGGAGAAGAAATACAGCCCTTGTGCCTGGGAGGTTGT
CAGAGCAGAAATCATGAGATCCCTCTCTTTTTCAACAAACTTGCAAAAAA
GATTAAGGAGGAAGGATTGA
                                       SEQ ID NO: 30
MALSFSLLMAMVVLSYKSICSLGCDLPQTHSLGHRRALILLAQMGRISPF
SCLKDRHDFGFPQEEFDGNQFQKAQAMSVLHEMIQQTFNLFSTKDSSAAW
DETLLDKFYIELFQQLNDLEACVIQEAGVEETPLMNEDSILAVRKYFQRI
TLYLTEKKYSPCAWEVVRAEIMRSLSFSTNLQKRLRRKD*
                                       SEQ ID NO: 31
ATGGCCCTGTCCTTTTCTTTACTGATGGCCGTGGTGGTGCTCAGCTACAA
ATCCATCTGCTCTCTGGGCTGTGATCTGCCTCAGACCCACAGCCTGGGTC
ATAGGAGGGCCTTGATACTCCTGGCACAAATGCAAAGAATCTCTCTTCCC
TCCTGCCTGAAGGACAGGCATGACTTTGCATTCCCCCAGGAGGAGTTTGA
TGGCAACCAGTTCCAGAAGGCTCAAGCCATCTCTGTCCTCCATGAGATGA
TCCAGCAGACCTTCAATCTCTTCAGCACAAAGGACTCATCTGCTGCTTGG
```

GATGAGACCCTCCTAGACAAATTCTACATTGAACTTTTCCAGCAACTGAA

TGACCTGGAAGCCTGTGTGATACAGGAGGCTGGGGTAGAAGAGACTCCCC

TGATGAATGAGGACTCCATCCTGGCTGTGAGGAAATACTTCCAAAGAATC

ACTCTCTATCTGATGGAGAAGAAATACAGCCCTTGTGCCTGGGAGGTTGT

CAGAGCAGAAATGATGAGATCCTTCTCTTTTTCAACAACCTTACAAGAAA

GATTAAGGAGGAAGTAATGA

SEQ ID NO: 32
MALSFSLLMAVVVLSYKSICSLGCDLPQTHSLGHRRALILLAQMQRISLP
SCLKDRHDFAFPQEEFDGNQFQKAQAISVLHEMIQQTFNLFSTKDSSAAW
DETLLDKFYIELFQQLNDLEACVIQEAGVEETPLMNEDSILAVRKYFQRI
TLYLMEKKYSPCAWEVVRAEIMRSFSFSTTLQERLRRK**

SEQ ID NO: 33
ATGGCCCTGTCCTTTTCTTTACTGATGGCCGTGGTGGTGCTCAACTACAA
ATCCATCTGCTCTCTGGGCTGTGATCTGCCTCAGACCCACAGCCTGGGTC
ATAGGAGGGCCTTGATACTCCTGGCACAAATGCAAAGAATCTCTCTTCCC
TCCTGCCTGAAGGACAGGCATGACTTTGCATTCCCCCAGGAGGAGTTTGA
TGGCAACCAGTTCCAGAAGGCTCAAGCCATCTCTGTCCTCCATGAGATGA
TCCAGCAGACCTTCAATCTCTTCAGCACAAAGGACTCATCTGCTGCTTGG
GATGAGACCCTCCTAGACAAATTTTACATTGAACTTTTCCAGCAACTGAA
TGACCTGGAAGCCTGTGTGATACAGGAGGCTGGGGTAGAAGAGACTCcCC
TGATGAATGAGGACTCCATCCTGGCTGTGAGGAAATACTTCCAAAGAATC
ACTCTCTATCTGACGGAGAAGAAATACAGCCCATGTGCCTGGGAGGTTGT
CAGAGCAGAAATCATGAGATCCCTCTCTTTTTCAACAAACTTGCAAAAAA
GATTAAGGAGGAAGGATTGA

SEQ ID NO: 34
MALSFSLLMAVVVLNYKSICSLGCDLPQTHSLGHRRALILLAQMQRISLP
SCLKDRHDFAFPQEEFDGNQFQKAQAISVLHEMIQQTFNLFSTKDSSAAW
DETLLDKFYIELFQQLNDLEACVIQEAGVEETPLMNEDSILAVRKYFQRI
TLYLTEKKYSPCAWEVVRAEIMRSLSFSTNLQKRLRRKD*

SEQ ID NO: 35
ATGGCCCTGTCCTTTTCTTTACTGATGGCCGTGGTGGTGCTCAACTACAA
ATCCATCTGCTCTCTGGGCTGTGATCCTCCCCAGACCCACAGCCTGGGTC
ATAGGAGGGCCTTGATACTCCTGGCACAAATGGGAAGAATCTCTCCTTTC
TCCTGTCTGAAGGACAGACGTGACTTTGGATTCCCCCAGGAGGAGTTTGA
TGGCAACCAGTTCCAGAAGGCTCAAGCCATGTCTGTCCTCCATGAGATGA
TCCAGCAGACCTTCAATCTCTTCAGCACAAAGGACTCATCTGCTGCTTGG
GAACAGAACCTCCTAGAAAAATTTCCGCTGAGCTTTACCAGCAACTGAA
TGCCTTGGAAGCCTGTGTGATAGCAGAGCCTGGGATGGAAGAGACTCTCT
TGATGAATGAGGACTCCATCCTGGCTATGAAGAAATACTTCCAAAGAATC
ACTCTCTATCTAACGGAGAAGAAGTACAGCCCTTGTGCCTGGGAGGTTGT
CAGAGCAGAAATCATGAGATCCCTCTCTTTTTCAACAAACTTGCAAAGAA
AATTAAGGAGGAAGGATTGA

SEQ ID NO: 36
MALSFSLLMAVVVLNYKSICSLGCDPPQTHSLGHRRALILLAQMGRISPF
SCLKDRRDFGFPQEEFDGNQFQKAQAMSVLHEMIQQTFNLFSTKDSSAAW
EQNLLEKFSAELYQQLNALEACVIAEPGMEETLLMNEDSILAMKKYFQRI
TLYLTEKKYSPCAWEVVRAEIMRSLSFSTNLQRKLRRKD*

SEQ ID NO: 37
ATGGCCCTGTCCTTTTCTTTACTGGTGGCCGTGGTGGTGCTCAGCTACAA
ATCCATCTGCTCTCTGGGCTGTGATCTGCCTCGGACCCACAGCCTGGGTC
ATAGGAGGTCCTTGATACTCCTGGCACAAATGGGAAGAATCTCTCCTTTC
TCCTGTCTGAAGGACAGACATGACTTTGGATTCCCCCAGGAGGAGTTTGA
TGGCAACCAGTTCCACAAGGCTCAAGCCATCTCTGTCCTCCATGAGATGA
TCCAGCAGACCTTCAATCTCTTCAGCACAAAGGACTCATCTGCTGCTTGG
GAACACAGCCTCCTAGAAAAATTTTCCACTGGACTTTACCAGCAACTGAA
TGACCTGGAAGCCTGTGTGATACAGGAGGTTGGAGTGGAAGAGACTCCAC
TGACGAATGTGGACTGCATCCTGGCTGTGAGGAAATACTTCCAAAGAATC
ACCCTCTATCTGATGGAGAAGAAATACAGCCCTTGTGCCTGGGAGGTTGT
CAGAGCAGAAATCATGAGATCCTTCTCTTTTTCACAACCTTACAAGAAA
GATTAAGGAGGAAGTAATGA

SEQ ID NO: 38
MALSFSLLVAVVVLSYKSICSLGCDLPRTHSLGHRRSLILLAQMGRISPF
SCLKDRHDFGFPQEEFDGNQFHKAQAISVLHEMIQQTFNLFSTKDSSAAW
EHSLLEKFSTGLYQQLNDLEACVIQEVGVEETPLTNVDCILAVRKYFQRI
TLYLMEKKYSPCAWEVVRAEIMRSFSFFTTLQERLRRK**

SEQ ID NO: 39
ATGGCCCTGTCCTTTTCTTTACTGGTGGCCGTGGTGGTGCTCAGCTACAA
ATCCATCTGCTCTCTGGGCTGTGATCTGCCTCGGACCCACAGCCTGGGTC
ATAGGAGGGCCTTGATACTCCTGGCACAAATGGGAAGGATCTCTCCTTTC
TCCTGTCTGAAGGACAGACATGACTTTGGATTCCCCCAGGAGGAGTTTGA
TGGCAACCAGTTCCAGAAGGCTCAAGCCATCTCTGTCCTCCATGAGATGA
TCCAGCAGACCTTCAATCTCTTCAGCACAAAGGACTCATCTGCTGCTTGG
GAACAGAACCTCCTAGAAAAATTTTCCACTGGACTTTACCAGCAACTGAA
TGACCTGGAAGCCTGTGTGATACAGGAGGTTGGAGTGGAAGAGACTCCAC
TGACGAATGTGGACTGCATCCTGGCTGTGAGGAAATACTTCCAAAGAATC
ACCCTCTATCTGATGGAGAAGAAATACAGCCCTTGTGCCTGGGAGGTTGT
CAGAGCAGAAATCATGAGATCCTTCTCTTTTTCAACAACCTTACAAGAAA
GATTAAGGAGGAAGTAATGA

SEQ ID NO: 40
MALSFSLLVAVVVLSYKSICSLGCDLPRTHSLGHRRALILLAQMGRISPF
SCLKDRHDFGFPQEEFDGNQFQKAQAISVLHEMIQQTFNLFSTKDSSAAW
EQNLLEKFSTGLYQQLNDLEACVIQEVGVEETPLTNVDCILAVRKYFQRI
TLYLMEKKYSPCAWEVVRAEIMRSFSFSTTLQERLRRK**

SEQ ID NO: 41
AGCAAAGTCTTCAGAAAACCTAGAGGCCAAGGTTCAAGGTTACCCACCTC
AGTAGCCTAGCAATATTTGCAACATCCCAATGGCCCTGTCCTTTTCTTTA

CTGATGGCCGTGGTGGTGCTCAGCTACAAATCCATCTGCTCTCTGGGCTG
TGATCCTCCCCAGACCCACAGCCTGGGTCATAGGAGGGCCTTGATACTCC
TGGCACAAATGGGAAGAATCTCTCCTTTCTCCTGTCTGAAGGACAGACAT
GACTTTGGATTCCCCCAGGAGGAGTTTGATGGCAACCAGTTCCAGAAGGC
TCAAGCCATCTCTGTCCTCCATGAGATGATCCAGCAGACCTTCAATCTCT
TCAGCACAAAGGACTCATCTGCTGCTTGGGAACAGAACCTCCTAGAAAAA
TTTTCCGCTGAGCTTTACCAGCAACTGAATGCCTTGGAAGCCTGTGTGAT
AGCAGAGCCTGGGATGGAAGAGACTCTCTTGATGAATGAGGATTCCATCC
TGGCTGTGAAGAAATACTTCCAAAGAATCACTCTCTATCTGACGGAGAAG
AAGTACAGCCCCTGTGCCTGGGAGGTTGTCAGAGCAGAAATCATGAGATC
CCTCTCTTTTTCAACAAACTTGCAAAGAAAATTAAGGAGGAAGGATTGAA
AACTGGTTCAACATGGAAATGATCCTCATTGACGGACATGTCATCTCACA
CTTTCATGAGTTCTTCCATTTCAAAGACTCATGACTCTTATAACCACGAA
TC

SEQ ID NO: 42
MALSFSLLMAVVVLSYKSICSLGCDPPQTHSLGHRRALILLAQMGRISPF
SCLKDRHDFGFPQEEFDGNQFQKAQAISVLHEMIQQTFNLFSTKDSSAAW
EQNLLEKFSAELYQQLNALEACVIAEPGMEETLLMNEDSILAVKKYFQRI
TLYLTEKKYSPCAWEVVRAEIMRSLSFSTNLQRKLRRKD*

SEQ ID NO: 43
CACTATTTAAGATCCATGCACAGAGCAAGGTCTTCAGGAAACCTAGAGGC
CAAGGTTCAAGGTTACCCACCTCACGTAGCCTAGCAATATTGACAACATC
CCAATGGCCCTGTCCTTTTCTTTACTGATGGCCGTGGTGGTGCTCAGCTA
CAAATCCATCTGCTCTCTGGGCTGTGATCTTCCTCAGACCCACAGCCTGG
GTCATAGGAGGGCCTTGATACTCCTGGCACAAATGGGAAGGATCTCTCCG
TTCTCCTGTCTGAAGGACAGACGTGACTTTGCATTCCCCCAGGAGGAGTT
TGATGGCAACCAGTTCCAGAAGGCTCAAGCCATGTCTGTCCTCCATGAGA
TGATCCAGCAGACCTTCAATCTCTTCAGCACAAAGGACTCATCTGCTGCT
TGGGAACAGAACCTCCTAGAAAAATTTTCCGCTGAGCTTTACCAGCAACT
GAATGACCTGAAAGCCTGTGTGATAGCAGAGCCTGGGATGGAAGACACTC
CCTTGATGAATGAGGACTCCATCCTGGCTGTGAAGAAATACTTCCAAAGA
ATCACTCTCTATCTGACGGAGAAGAAATACAGCCCTTGTGCCTGGGAGGT
TGTCAGAACAGAAATCATGAGATCCCTCTCTTTTTCAACAAACTTGCAAA
AAAGATTAAGGAGGAAGGATTGAAAACTGGTTCAACATGGAAATGATCCG
AATTCTGCAGATATCCATCACACTGGCGGCC

SEQ ID NO: 44
MALSFSLLMAVVVLSYKSICSLGCDLPQTHSLGHRRALILLAQMGRISPF
SCLKDRRDFAFPQEEFDGNQFQKAQAMSVLHEMIQQTFNLFSTKDSSAAW
EQNLLEKFSAELYQQLNDLKACVIAEPGMEDTPLMNEDSILAVKKYFQRI
TLYLTEKKYSPCAWEVVRTEIMRSLSFSTNLQKRLRRKD*

SEQ ID NO: 45
GATCCATGCACGGAGCAAAGTCTTCAGAAAACCTAGAGGCCAAGTTTCAA
GGTTACCCACCTCAAGTAGCCTAGCAATATTGACAACATCCCAATGGCCC
TGTCCTTTTCTTTACTGATGGCCGTGGTGGTGCTCAACTACAAATCCATC
TGCTCTCTGGGCTGTGATCTGCCTCGGACCCACAGCCTGGGTCATAGGAG
GGCCTTGATACTCCTGGCACAAATGGGAAGAATCTCTCCTTTCTCCTGTC
TGAAGGACAGACATGACTTTGGATTCCCCCAGGAGGAGTTTGATGGCAAC
CAGTTCCAGAAGGCTCAAGCCATCTCTGTCCTCCATGAGATGATCCAGCA
GACCTTCAATCTCTTCAGCACAAAGGACTCATCTGCTGCTTGGGAACAGA
ACCTCCTAGAAAAATTTTCCGCTGAGCTTTACCAGCAACTGAATGACCTG
AAAGCCTGTGTGATAGCAGAGCCTGGGATGGAAGACACTCCCTTGATGAA
TGAGGACTCCATCCTGGCTGTGAAGAAATACTTCCAAAGAATCACTCTCT
ATCTGACGGAGAAGAAATACAGCCCATGTGCCTGGGAGGTTGTCAGAACA
GAAATCATGAGATCCCTCTCTTTTTCAACAAACTTGCAAAAAAGATTAAG
GAGGAAGGATTGAAAACTGGTTCAACATGGAAATGATCCGAATTCTGCAG
ATATCCATCACACTGGCGGCCGCTCGAGCATGCATCTAGAGGGCCCCTAT
TCTATAGTGTCACCTAAATGCTAGAGCTCGCTGATCAGCCTCGACTGGGC
CTTCTAATTGCCAGCCATCTGTTGTTTGCCCCTCCCCCGTGCCNTC

SEQ ID NO: 46
MALSFSLLMAVVVLNYKSICSLGCDLPRTHSLGHRRALILLAQMGRISPF
SCLKDRHDFGFPQEEFDGNQFQKAQAISVLHEMIQQTFNLFSTKDSSAAW
EQNLLEKFSAELYQQLNDLKACVIAEPGMEDTPLMNEDSILAVKKYFQRI
TLYLTEKKYSPCAWEVVRTEIMRSLSFSTNLQKRLRRKD*

SEQ ID NO: 47
TAGGAATTAGCTTGGTACCCTAGAGGCCAAGGTTCAAGGTTACCCACCTC
AAGTAGCCTAGCAATATTTGCAACATCCCAATGGCCCTGTCCTTTTCTTT
ACTGATGGCCGTGGTGGTGCTCAGCTACAAATCCATCTGCTCTCTGGGCT
GTGATCCTCCCCGGACCCACAGCCTGGGTCATAGGAGGGCCTTGATACTC
CTGGCACAAATGGAAAGAATCTCTCCTTTCTCCTGTCTGAAGGACAGATG
TGACTTTGCATTCCCCCAGGAGGAGTTTGATGGCAACCAGTTCCAGAAGG
CTCAAGCCATGTCTGTCCTCCATGAGATGATCCAGCAGACCTTCAATCTC
TTCAGCACAAAGGACTCATCTGCTGCTTGGGAACAGAACCTCCTAGAAAA
ATTTTCCGCTGAGCTTTACCAGCAACTGAATGACCTGAAAGCCTGTGTGA
TAGCAGAGCCTGGGATGGAAGAGACTCTCTTGATGAATGAGGACTCCATC
CTGGCTGTGAAGAAATACTTCCAAAGAATCACTCTCTATCTGACGGAGAA
GAAGTACAGCCCCTGTGCCTGGGAGGTTGTCAGAGCAGAAATCATGAGAT
CCCTCTCTTTTTCAACAAACTTGCAAAAAAGATTAAGGAGGAAGGATTGA
AAGAATTC

SEQ ID NO: 48
MALSFSLLMAVVVLSYKSICSLGCDPPRTHSLGHRRALILLAQMERISPF
SCLKDRCDFAFPQEEFDGNQFQKAQAMSVLHEMIQQTFNLFSTKDSSAAW

EQNLLEKFSAELYQQLNDLKACVIAEPGMEETLLMNEDSILAVKKYFQRI
TLYLTEKKYSPCAWEVVRAEIMRSLSFSTNLQKRLRRKD*

SEQ ID NO: 49
TCAGACGTGGTTNAAGTTTTTTCTTCCATTTCAGGTGTCGTGAGGCAGT
ATGTTCACTATTTAACACCTATGCACAGAGCAAGGTCTTCAGAAAACTTA
CAGCCCAGGGTTCAGGGTTACTCCTCATCAACCAGCCCAGCAGCATCTTC
AGGATTCCCAATGGCATTGCCCTTTGCTTTAATGATGGCCCTGCTGGTGC
TTAGCTACAAGTCAAGCTGCTCTCTGGGCTGTAATCCATCTCAAACCCAC
AACATGAATAACAGGAGGACTTTGATGCTCATGGCACAAATGAGGAGAAT
CTCTCCTTTTTCATGCCTGAAGGACAGAAATGACTTTGAATTTCCCCAGG
AGGAGTTTGATGGCAACCAGTTCCAGAATACTCAAGCCATCTCTGTCCTC
CATGAGATGATGCAGCAGACCTTCAATCTCTTCAGCACAAAGGACTCATC
TGCTGCTTGGGATGAGACCCTCCTAGACAAATTCTACATTGAACTTTTCC
AGCAACTGAATGACCTGGAAGCCTGTGTGATACAGGAGGCTGGGGTAGAA
GAGACTCCCCTGATGAATGAGGACTCCATCCTGGCTGTGAGGAAATACTT
CCAAAGAATCACTCTCTATCTGATGGAGAAGAAATACAGCCCTTGTGCCT
GGGAGGTTGTCAGAGCAGAAATCATGAGATCCCTCTCTTTTTCAACAAAC
TTGCAAAAAAGATTAAGGAGGAAGGATTGAAAACTGGTTCAACATGGAAA
TGATCCTCATTGACTATACATCATCTCACACTTTCATGAGTTCTTCCATT
TCAAAGACTCATGTCTCTTATAACCACCACGAGTGGAATTC

SEQ ID NO: 50
MALPFALMMALLVLSYKSSCSLGCNPSQTHNMNNRRTLMLMAQMRRISPF
SCLKDRNDFEFPQEEFDGNQFQNTQAISVLHEMMQQTFNLFSTKDSSAAW
DETLLDKFYIELFQQLNDLEACVIQEAGVEETPLMNEDSILAVRKYFQRI
TLYLMEKKYSPCAWEVVRAEIMRSLSFSTNLQKRLRRKD*

SEQ ID NO: 51
GTACCCAGAGATAGAAAGTAAAAACTAGGGCATTTAGAAAATGGAAATTA
TTATGTTCACTATTTAAGACCCATGCACAGAGCAAAGTCTTCAGAAAACC
TAGAGGCCAAGGTTCAAGGTTACCCACCTCACGTAGCCTAGCAATATTTG
CAACATCCCAATGGCCCTGTCCTTTTCTTTACTGATGGCCGTGGTGGTGC
TCAGCTACAAATCCATCTGCTCTCTGGGCTGTGATCTGCCTCAGACCCAC
AGCCTGGGTCATAGGAGGGCCTTGATACTCCTGGCACAAATGCAAAGAAT
CTCTCTTCCCTCCTGCCTGAAGGACAGGCATGACTTTGCATTCCTCCAGG
AGTTTGATGGCAACCAGTTCCAGAAGGCTCAAGCCATGTCTGTCCTCCAT
GAGATGATCCAGCAGACCTTCAATCTCTTGAGCACAAAGGACTCATCTGC
TGCTTGGGATGAGACCCTCCTAGACAAATTCTACATTGAACTTTTCCAGC
AACTGAATGACTTGGAAGCCTGTGTGATACAGGAGGCTGGGGTAGAAGAG
ACTCCCCTGATGAATGAGGACTCCATCCTGGCTGTGAGGAAATACTTCCA
AAGAATCACTCTCTATCTGACGGAGAAGAAATACAGCCCTTGTGCCTGGG
AGGTTGTCAGAGCAGAAATCATGAGATCCCTCTCTTTTTCAACAAACTTG
CAAAAAAGATTAGGGAGGAAGGATTGAAAACTGGTTCAACACGGAAATGA
GAATTC

SEQ ID NO: 52
MALSFSLLMAVVVLSYKSICSLGCDLPQTHSLGHRRALILLAQMQRISLP
SCLKDRHDFAFLQEFDGNQFQKAQAMSVLHEMIQQTFNLLSTKDSSAAWD
ETLLDKFYIELFQQLNDLEACVIQEAGVEETPLMNEDSILAVRKYFQRIT
LYLTEKKYSPCAWEVVRAEIMRSLSFSTNLQKRLGRKD*

SEQ ID NO: 53
AGCCTCAGACAGNGGTCAAAGTTTTTTTCTTCCATTNCAGGNGTCGGTGA
GGAATTAGCTTGGTACCCACGAGATAGAAAGTAAAACTAGAGCCTTTAG
AAAATGGAAATTAGTATGtTCACTATTTAAGATCCATGCACAGAGCAAGG
TCTTCAGGAAACCTGGAGGCCAAGGTTCAAGGTTACCCACCTCAGTAGCC
TAGCAATATTTGCAACATCCCAATGGCCCTGTCCTTTTCTTTACTGGTGG
CCGTGGTGGTGCTCAGCTACAAATCCATCTGCTCTCTGGGCTGTGATCTG
CCTCGAACCCACAGCCTGGGTCATAGGAGGGCCTTGATACTCCTGGCACA
AATGGGAAGAATCTCTCCTTTCTCCTGTCTGAAGGACAGACATGACTTTG
GATTCCCCCAGGAGGAGTTTGATGGCAACCAGTTCCAGAAGGCTCAAGCC
ATCTCTGTCCTCCATGAGATGATCCAGCAGACCTTCAATCTCTTCAGCAC
AAAGGACTCATCTGCTGCTTGGGAACACAGCCTCCTAGAAAAATTTTCCG
CTGAGCTTTACCAGCAACTGAATGACCTGGAAGCCTGTGTGATACAGGAG
GTTGGAGTGGAAGAGACTCCACTGACGAATGTGGACTGCATCCTGGCTGT
GAAGAAATACTTCCAAAGAATCACCCTCTATCTGATGGAGAAGAAATACA
GCCCTTGTGCCTGGGAGGTTGTCAGAGCAGAAATCATGAGATCCTTCTCT
TTTTCAACAACCTTACAAGAAAGATTAAGGAGGAAGTAATGAAAGCTGGT
TCAACACGGAAATAGAATTACT

SEQ ID NO: 54
MALSFSLLVAVVVLSYKSICSLGCDLPRTHSLGHRRALILLAQMGRISPF
SCLKDRHDFGFPQEEFDGNQFQKAQAISVLHEMIQQTFNLFSTKDSSAAW
EHSLLEKFSAELYQQLNDLEACVIQEVGVEETPLTNVDCILAVKKYFQRI
TLYLMEKKYSPCAWEVVRAEIMRSFSFSTTLQERLRRK*

SEQ ID NO: 55
CTTCANNACAAGTAAAACTAGAGCCTTTAGAAAATGGAAATTAGTATGTT
CACTATTTAAGACCCATGCACAGAGCAAAGTCTTCAGAAAACCTAGAGGC
CAAGGTTCAAGGTTACCCACCTCACGTAGCCTAGCAATATTGACAACATC
CCAATGGCCCTGTCCTTTTCTTTACTGATGGCCGTGGTGGTGCTCAGCTA
CAAATCCATCTGCTCTCTGGGCTGTGATCTTCCTCAGACCCACAGCCTGG
GTCATAGGAGGGCCTTGATACTCCTGGCACAAATGGGAAGGATCTCTCCG
TTCTCCTGTCTGAAGGACAGACATGACTTTGGATTCCCCCAGGAGGAGTT
TGATGGCAACCAGTTCCAGAAGGCTCAAGCCATGTCTGTCCTCCATGAGA
TGATCCAGCAGACCTTCAATCTCTTCAGCACAAAGGACTCATCTGCTGCT
TGGGAACAGAACCTCCTAGAAAAATTTTCCGCTGAGCTTTACCAGCAACT
GAATGACCTGAAAGCCTGTGTGATAGCAGAGCCTGGGATGGAAGACACTC
CCTTGATGAATGAGGACTCCATCCTGGCTGTGAAGAAATACTTCCAAAGA
ATCACTCTCTATCTGACGGAGAAGAAGTACAGCCCCTGTGCCTGGGAGGT

```
TGTCAGAGCAGAAATCATGAGATCCCTCTCTTTTTCAACAAACTTGCAAA
AAAGATTAAGGAGGAAGGATTGAAAACTGGTTCAACACGGNAAATGAAAA
TTCTGCAGATATCCATCACACTGGCGGCCGCTCGAGCATGCATCTAAAGG
GCCCTATTCTTAAGTGTNACCTAAATGCTAAAGCNCNCTGATCANCCTCN
ATGTGCCTTTTAATTGCCCGCCATCTGNTGTTGGCCCCTCCCCGGGCCNT
TCTTGNACCTGGAANGGNCNCTCCCATNGTCNTTNCTAAAAAAGAAAAA
TTGCCTCCCATN
```

SEQ ID NO: 56
```
MALSFSLLMAVVVLSYKSICSLGCDLPQTHSLGHRRALILLAQMGRISPF
SCLKDRHDFGFPQEEFDGNQFQKAQAMSVLHEMIQQTFNLFSTKDSSAAW
EQNLLEKFSAELYQQLNDLKACVIAEPGMEDTPLMNEDSILAVKKYFQRI
TLYLTEKKYSPCAWEVVRAEIMRSLSFSTNLQKRLRRKD*
```

SEQ ID NO: 57
```
AAGACGTTCAGAAAATGGAAGCTAGTATGTTCCCTATTTAAAACCTATGC
ACAGAGCAAGGTCtTCAGAAAACTTACAGCCCAGGGTTCAGGGTTACTCC
TCATCAACCAGCCCAGCAGCATCTTCAGGATTCCCAATGGCATTGCCCTT
TGCTTTAATGATGGCCCTGCTGGTGCTTAGCTACAAGTCAAGCTGCTCTC
TGGGCTGTAATCCGTCTCAAACCCACAACATGAATAACAGGAGGACTTTG
ATGCTCATGGCACAAATGAGGAGAATCTCTCCTTTTTCATGCCTGAAGGA
CAGAAATGACTTTGAATTTCCCCAGGAGGAGTTTGATGGCAACCAGTTCC
AGAATACTCAAGCCATCTCTGTCCTCCATGAGATGATCCAGCAGACCTTC
AATCTCTTCAGCACAAAGGACTCATCTGCTGCTTGGGATGAGACCCTCCT
AGACAAATTCTACATTGAACTTTTCCAGCAACTGAATGACCTGGAAGCCT
GTGTGATACAGGAGGCTGGGGTAGAAGAGACTCCCCTGATGAATGAGGAC
TCCATCCTGGCTGTGAAGAAATACTTCCAAAGAATCACTCTCTATCTGAT
GGAGAAGAAATACAGCCCTTGTGCCTGGGAGGTTGTCAGAGCAGAAATCA
TGAGATCCCTCTCTTTTTCAACAAACTTGCAAAAAAGATTAAGGAGGAAG
GATTGAAAACTGGTTCAACATGGAAATGATCCTCATTGACTATACATCAT
CTCACACTTTAATGAGTTCTTCCATTTCAAAGACTCATGTCNCTTATAAC
CACCACGAGTTGAGA
```

SEQ ID NO: 58
```
MALPFALMMALLVLSYKSSCSLGCNPSQTHNMNNRRTLMLMAQMRRISPF
SCLKDRNDFEFPQEEFDGNQFQNTQAISVLHEMIQQTFNLFSTKDSSAAW
DETLLDKFYIELFQQLNDLEACVIQEAGVEETPLMNEDSILAVKKYFQRI
TLYLMEKKYSPCAWEVVRAEIMRSLSFSTNLQKRLRRKD*
```

SEQ ID NO: 59
```
AGGCTAATNACAGCAAAATGGNAAGTGAGTATGTTCCCTATATAAGGCCG
TGTACAAACCAAAGTCTTCAGAGATCCTGGAGCCCAAAGTTAAGGGTCAT
CCATCTGAACCAGCTCAGCAGCATCCGCAACATCTACAATGGCCTTGACC
TTTTATTTACTGATGGCCCTAGTGGTGCTCAGCTACAAGCCATTCAGCTC
TCTGGGCTGTGATCTGCCTCAGACCCACAGCCTGGGTTACAGGAGGCCCT
TGGTGCTCCTGGCACAAATGAGAAGAATCTCTCCTTTTCTCCTGCCTGAAG
GACAGACATGACTTTGAATTACCCCAGGAGGAGTTTGATGACAAAAACTT
CCAGAAGGCTCAAGCCATCTCTGTCCTCCATGAGATAATCCAGCAGACCT
TCAACCTCTTCAACACAAAGAATTCATCTGCTGCTTTCAATGAGACCCTT
CTAGATGAATTCTACATCGAACTTGACCAGCAGCTGAATGACCTGGAGTC
CTGTGTGATGCAGGAAGTGGGGGTGACAGAGACTCACCTGATGTACGAGG
ACTCCATCCTGGCTGTGAAGAAATACTTCCGAAGAATCACTCTCTATCTG
ACAGAGAAGAAATACAGCCCTTGTGCCTGGGAGGTTGTCAGAGCAGAAAT
CATGAGATCCTTCTCTTTATCAATCAACTTGCAAAAAGATTGAAGAGTA
AGGAATAAGACCTGGTGCAACATGGAAATGATTCTTATAGACTAATATGN
CAGCTCACACTCCAAAGCAAAAT
```

SEQ ID NO: 60
```
MALTFYLLMALVVLSYKPFSSLGCDLPQTHSLGYRRPLVLLAQMRRISPF
SCLKDRHDFELPQEEFDDKNFQKAQAISVLHEIIQQTFNLFNTKNSSAAF
NETLLDEFYIELDQQLNDLESCVMQEVGVTETHLMYEDSILAVKKYFRRI
TLYLTEKKYSPCAWEVVRAEIMRSFSLSINLQKRLKSKE
```

SEQ ID NO: 61
```
GTCGAACAAAGAAAGCAAAAACAGTAGATAGAAAGTAAAACTAGGCATTT
AGAAAATGGAAATTAGTATGTTCACTATTTAAGATCCATGCACGGAGCAA
AGTCTTCAGAAAACCTAGAGGCCAAGGTTCAAGGTTACCCACCTCAAGTA
GCCTAGCAATATTTGCAACATCCCAATGGCCCTGTCCTTTTCTTTACTGA
TGGCCGTGGTGGTGCTCAGCTACAAATCCATCTGCTCTCTGGGCTGTGAT
CCTCCCCGGACCCACAGCCTGGGTCATAGGAGGGCCTTGATACTCCTGGC
ACAAATGGAAAGAATCTCTCCTTTCTCCTGTCTGAAGGACAGACATGACT
TTGGATTCCCCCAGGAGGAGTTTGATGGCAACCAGTTCCAGAAGGCTCAA
GCCATCTCTGTCCTCCATGAGATGATCCAGCAGACCTTCAATCTCTTCAG
CACAAAGGACTCATCTGCTGCTTGGGAACAGAACCTCCTAGAAAAATTTT
CCGCTGAGCTTTACCAGCAACTGAATGCCTTGGAAGCCTGTGTGATAGCA
GAGCCTGGGATGGAAGAGACTCTCTTGATGAATGAGGATTCCATCCTGGC
TGTGAAGAAATACTTCCAAAGAATCACTCTCTATCTGACGGAGAAGAAGT
ACAGCCCCTGTGCCTGGGAGGTTGTCAGAGCAGAAATCATGAGATCCCTC
TCTTTTTCAACAAACTTGCAAAAAAGATTAAGGAGGAAGGATTGAAAACT
AGTTCAACATGGAAATGATCCTCATTGACGGACATGTCATCTCACACTTT
CATGAGTTCTTCCATTTCAAAGACTCATGACTCTTATAACCACCACGAGT
TGAATCAAAATGTTCAAAAGTTTTCAGGAGTGTAAAGAAGCATCGTGTTC
GCCTGTGCAGGCACTAGTCCTTTACAGATGACCACGCTGAGAATTC
```

SEQ ID NO: 62
```
MALSFSLLMAVVVLSYKSICSLGCDPPRTHSLGHRRALILLAQMERISPF
SCLKDRHDFGFPQEEFDGNQFQKAQAISVLHEMIQQTFNLFSTKDSSAAW
EQNLLEKFSAELYQQLNALEACVIAEPGMEETLLMNEDSILAVKKYFQRI
TLYLTEKKYSPCAWEVVRAEIMRSLSFSTNLQKRLRRKD*
```

SEQ ID NO: 63
```
TNCAATACCCTAGNCAACATTGACAACATCCCAATGGCCCTGTCCTTTTC
TTTACTGATGGCCGTGGTGGTGCTCAGCTACAAATCCATCTGCTCTCTGG
```

101

-continued

```
GCTGTGATCTTCCTCAGACCCACAGCCTGGGTCATAGGAGGGCCTTGATA
CTCCTGGCACAAATGGGAAGGATCTCTCCGTTCTCCTGTCTGAAGGACAG
GCATGACTTTGCATTCCCCCAGGAGGAGTTTGATGGCAACCAGTTCCAGA
AGGCTCAAGCCATCTCTGTCCTCCATGAGATGATCCAGCAGACCTTCAAT
CTCTTCAGCACAAAGGACTCATCTGCTGCTTGGGAACAGAACCTCCTAGA
AAAATTTTCCGCTGAGCTTTACCAGCAACTGAATGACCTGAAAGCCTGTG
TGATAGCAGAGCCTGGGATGGAAGACACTCCCTTGATGAATGAGGACTCC
ATCCTGGCTGTGAAGAAATACTTCCAAAGAATCACTCTCTATCTGACGGA
GAAGAAATACAGCCCTTGTGCCTGGGAGGTTGTCAGAGCAGAAATCATGA
GATCCCTCTCTTTTTCAACAAACTTGCAAAAAAGATTAAGGAGGAAGGAT
TGAAAACTGGTTCAACATGGAAATGATCCTTCATTGACGGACATGTCATC
TCACACTTTNCATGAGTTCTTNCATTTNCAAAGACTCCTTTGAATTCTGC
AGANATCCATCNCACTGGGCGGCCGCTCGAGCATGCCNTCTANAGGGCCC
TATTCTANAGTGGCACCCTAAATGCTAANACCNCNCCTGATC
```

SEQ ID NO: 64
MALSFSLLMAVVVLSYKSICSLGCDLPQTHSLGHRRALILLAQMGRISPF
SCLKDRHDFAFPQEEFDGNQFQKAQAISVLHEMIQQTFNLFSTKDSSAAW
EQNLLEKFSAELYQQLNDLKACVIAEPGMEDTPLMNEDSILAVKKYFQRI
TLYLTEKKYSPCAWEVVRAEIMRSLSFSTNLQKRLRRKD*

SEQ ID NO: 65
```
GNCTAATNGGNAAAATGTAAATGAATATGTTCCCTATTTAAGGCTAGGCA
CAAAGCAAGGTCTTCAGAGAACCTAGAGCCTAACATTTAGGCTCACCCAT
TTCAACCAGCCTAGCAGCATCTGCAACATCTACAATGGCCTTGACCTTTG
CTTTACTGGTGGCCCTGGTGGTGCTCAGCTGCAAGTCAAGCTGCTCTCTG
GGCTGTGATCTACCTCAAACCCACAGCCTGGGTAACAGGAGGACCTTGAT
ACTCCTGGCACAAATGAGGAGAATCTCTCTTTTCTTCTGCCTGAAGGACA
GACATGACTTTGAATTTCCCCAGGAGGAGTTTGGCAACCAGTTCCAAAAG
GCTCAAACCATCCCTGTCCTCCATGAGATGATCCAGCAGACCTTCAATCT
CTTCAGCACAAAGGACTCATCTGCTGCTTGGGATGAGACCCTCCTAAACA
AATTCTACACTGAACTCTACCAGCAGCTGAATGACCTGGAAGCCTGTGTG
ATGCAGGAGATGGGGGTGACAGAGACTCCCCTGATGAACAAGAACTCCAT
```

102

-continued

```
CCTGGCCGTGAGGAAATACTTCCAAAGAATCACTCTCTATCTGAAAGAGA
AGAAATACAGTCTTTGTGCCTGGGAGGTTGTCAGAGCAGAAATTATGAGA
TCTTTTTCTTTGTCAACAAACTTGCAAGAAAGTTTAAGAAGTAAGGAATG
AAAACTGGTTCAACATGGAATTATTTTCATTGACTATACACCAGCTCAC
```

SEQ ID NO: 66
MALTFALLVALVVLSCKSSCSLGCDLPQTHSLGNRRTLILLAQMRRISLF
FCLKDRHDFEFPQEEFGNQFQKAQTIPVLHEMIQQTFNLFSTKDSSAAWD
ETLLNKFYTELYQQLNDLEACVMQEMGVTETPLMNKNSILAVRKYFQRIT
LYLKEKKYSLCAWEVVRAEIMRSFSLSTNLQESLRSKE*

SEQ ID NO: 67
```
CTGCTANTACNCCTAGNCAACATTTGCAACATCCCAATGGCCCTGTCCTT
TTCTTTACTGATGGCCGTGGTGGTGCTCAGCTACAAATCCATCTGCTCTC
TGGGCTGTGATCCTCCCCGGACCCACAGCCTGGGTCATAGGAGGGCCTTG
ATACTCCTGGCACAAATGGAAAGAATCTCTCCTTTCTCCTGTCTGAAGGA
CAGACATGACTTTGGATTCCCCAGGAGGAGTTTGATGGCAACCAGTTCC
AGAAGGCTCAAGCCATCTCTGTCCTCCATGAGATGATCCAGCAGACCTTC
AATCTCTTCAGCACAAAGGACTCATCTGCTGCTTGGGAACAGAACCTCCT
AGAAAAATTTTCCGCTGAGCTTTACCAGCAACTGAATGCCTTGGAAGCCT
GTGTGATAGCAGAGCCTGGGATGGAAGAGACTCTCTTGATGAATGAGGAT
TCCATCCTGGCTGTGAAGAAATACTTCCAAAGAATCACTCTCTATCTGAC
GGAGAAGAAGTACAGCCCCTGTGCCTGGGAGGTTGTCAGAGCAGAAATCA
TGAGATCCCTCTCTTTTTCAACAAACTTGCAAAGAAAATTAAGGAGGAAG
GATTGAAAACTGGTTCAACATGGAAATGATCCTTCATTGACGGACATGTCA
TCTCACACTTTCATGAGTTCTTCCATTTTCAAAGACTCACTTGAATTCTG
CAGATATCCATNCACACTGGNCGGCCGCTCGANCATGCATCTANAAGGGC
CCCTATTCTATAGTGTCNCCTAAATGC
```

SEQ ID NO: 68
MALSFSLLMAVVVLSYKSICSLGCDPPRTHSLGHRRALILLAQMERISPF
SCLKDRHDFGFPQEEFDGNQFQKAQAISVLHEMIQQTFNLFSTKDSSAAW
EQNLLEKFSAELYQQLNALEACVIAEPGMEETLLMNEDSILAVKKYFQRI
TLYLTEKKYSPCAWEVVRAEIMRSLSFSTNLQRKLRRKD*

*indicates termination of the protein sequence by a stop codon

---

What is claimed is:

1. An isolated interferon polypeptide, wherein the polypeptide is encoded by the isolated nucleic acid of SEQ ID NO: 65.

2. The isolated interferon polypeptide of claim 1, wherein the amino acid sequence is identical to SEQ ID NO: 66.

3. An isolated interferon polypeptide comprising an amino acid sequence set forth in SEQ ID NO: 66, or a biologically active fragment comprising a contiguous segment of at least 165 amino acids of SEQ ID NO: 66, wherein the segment is at least 165 amino acids in length.

4. A method of treating a subject suffering from an immune system-related disorder, comprising administering a therapeutically effective amount of the interferon polypeptide of any one of claims 1, 2 and 3.

5. A method for identifying a compound that enhances or inhibits the biological activity of the interferon polypeptide of any one of claims 1, 2, and 3, comprising:
   (a) treating a cell with the interferon polypeptide and a compound;
   (b) assessing the effect of the compound on the interferon polypeptide activity in a bioactivity assay and,
   (c) comparing the bioactivity assay from step (b) to a standard bioactivity assay using the interferon polypeptide in absence of the test compound.

6. The method according to claim 5, wherein the compound is selected from the group consisting of a small molecule, a synthetic organic compound, a synthetic inorganic compound, a polypeptide, a soluble polypeptide, a polypeptide-immunoglobulin fusion, a polyclonal antibody, a monoclonal antibody, an antibody fragment, a single-chain antibody, an anti-idiotypic antibody, a chimeric antibody, a humanized antibody, and a human antibody.

7. A composition comprising the interferon polypeptide of any one of claims 1, 2, and 3 and a pharmaceutically acceptable excipient.

8. A composition comprising the interferon polypeptide of claim 2.

9. The composition of claim 8, further comprising a pharmaceutically acceptable excipient.

10. A vaccine comprising the polypeptide of claim 2 as an adjuvant.

11. A preparation of an isolated polypeptide of claim 2, wherein said preparation has a specific activity of at least $1 \times 10^7$ U/mg in cytopathic effect assays in either LLC-MK2 cells using vesicular stomatitis virus or A549 cells using encephalomyocarditis virus.

12. A method of measuring a bio activity of the interferon polypeptide of claim 2, comprising:
   (a) treating a mammalian cell with the interferon polypeptide of claim 2; and
   (b) assessing the interferon polypeptide activity in a bioactivity assay.

* * * * *